(12) United States Patent
Glass et al.

(10) Patent No.: US 8,343,918 B2
(45) Date of Patent: Jan. 1, 2013

(54) STABILIZED INSULIN-LIKE GROWTH FACTOR POLYPEPTIDES

(75) Inventors: David Jonathan Glass, Cambridge, MA (US); Mara Fornaro, Basel (CH)

(73) Assignee: Novartis AG, Basel (CH)

( * ) Notice: Subject to any disclaimer, the term of this patent is extended or adjusted under 35 U.S.C. 154(b) by 882 days.

(21) Appl. No.: 12/304,068

(22) PCT Filed: Jun. 6, 2007

(86) PCT No.: PCT/US2007/070468
§ 371 (c)(1),
(2), (4) Date: Dec. 9, 2008

(87) PCT Pub. No.: WO2007/146689
PCT Pub. Date: Dec. 21, 2007

(65) Prior Publication Data
US 2010/0234290 A1    Sep. 16, 2010

Related U.S. Application Data

(60) Provisional application No. 60/897,187, filed on Jan. 24, 2007, provisional application No. 60/862,244, filed on Oct. 20, 2006, provisional application No. 60/812,349, filed on Jun. 9, 2006.

(51) Int. Cl.
*A61K 38/30* (2006.01)
*C07K 14/65* (2006.01)
*C07H 21/04* (2006.01)

(52) U.S. Cl. ......... 514/8.6; 530/324; 530/345; 536/23.5
(58) Field of Classification Search .................. None
See application file for complete search history.

(56) References Cited

U.S. PATENT DOCUMENTS

| | | | |
|---|---|---|---|
| 5,077,276 | A | 12/1991 | Ballard et al. |
| 7,355,018 | B2 | 4/2008 | Glass et al. |
| 7,396,918 | B2 | 7/2008 | Glass et al. |
| 7,632,503 | B2 | 12/2009 | Stitt et al. |
| 2004/0116335 | A1 | 6/2004 | Chen et al. |
| 2007/0135340 | A1 | 6/2007 | Rosenthal et al. |

FOREIGN PATENT DOCUMENTS

| | | |
|---|---|---|
| EP | 0235205 B1 | 10/1992 |
| WO | WO 87/01038 A1 | 2/1987 |
| WO | 89/05822 A1 | 6/1989 |
| WO | WO 95/13290 A1 | 5/1995 |
| WO | 95/32003 A1 | 11/1995 |
| WO | 97/33997 A1 | 9/1997 |
| WO | WO 97/33997 A1 | 9/1997 |
| WO | WO 01/36483 A1 | 5/2001 |
| WO | 01/85781 A2 | 11/2001 |
| WO | 03/066082 A1 | 8/2003 |
| WO | 2004/039956 A2 | 5/2004 |
| WO | 2006/056885 A2 | 6/2006 |
| WO | WO 20061066891 A2 | 6/2006 |
| WO | WO 2006/074390 A2 | 7/2006 |
| WO | 2006/097764 A1 | 9/2006 |
| WO | WO 2006/097682 A1 | 9/2006 |
| WO | WO 2007/141309 A2 | 12/2007 |
| WO | WO 2007/146689 A9 | 12/2007 |

OTHER PUBLICATIONS

Duguay et al., "Processing of Wild-type and Mutant Proinsulin-like Growth Factor-IA by Subtilisin-related Proprotein Convertases", The Journal of Biological Chemistry, 1997 vol. 272 No. 10 pp. 6663-6670.
Duguay et al., "Mutational Analysis of the Insulin-like Growth Factor I Prohormone Processing Site", The Journal of Biological Chemistry, 1995 vol. 270 No. 29 pp. 17566-17574.
Duguay et al., "Post-translational Processing of the Insulin-like Growth Factor-2 Precursor", The Journal of Biological Chemistry, 1998 vol. 273 No. 29 pp. 18443-18451.
Bryant et al., "Design and Characterisation of Long-R3-Insulin-Like Growth Factor-I Muteins Which Show Resistance to Pepsin Digestion", Growth Factors, 1996 vol. 13 No. 3 pp. 261-272.
Ulrich et al., "Insulin-like growth factor I receptor primary structure: comparison with insulin receptor suggests structural determinants that define functional specificity," EMBO J, 5(10)2503-2512 (1986).
Bagley et al., "A key functional role for the insulin-like growth factor 1 N-terminal pentapeptide," Biochem. J., 259:665-671 (1989).
Ross et al., "Insulin-like growth factor (IGF)-binding proteins inhibit the biological activities of IGF-1 and IGF-2 but not des-(1-3)-IGF-1," Biochem. J., 258:267-272 (1989).
Oh et al., "Characterization of the Affinities of Insulin-Like Growth Factor (IGF)-Binding Proteins 1-4 for IGF-I, IGF-II, IGF-I/Insulin Hybrid, and IGF-I Analogs," Endocrinology 132(3):1337-1344 (1993).
Duguay et al., "Processing of Wild-type and Mutant Proinsulin-like Growth Factor-IA by Subtilisin-related Proprotein Convertases," J. Biol. Chem. 272(10):6663-6670 (Mar. 7, 1997).
Jansson et al., "The Insulin-like Growth Factor (IGF) Binding Protein 1 Binding Epitope on IGF-I Probed by Heteronuclear NMR Spectroscopy and Mutational Analysis," J. Biol. Chem. 273(38):24701-24707 (Sep. 18, 1998).
Musaro et al., "The neuroprotective effects of a locally acting IGF-1 isoform," Experimental Gerontology 42:76-80 (2007).
Ballard et al., "Des(1-3)IGF-1: a Truncated Form of Insulin-like Growth Factor-I", Int. J. Biochem. Cell Biol., 1996 vol. 28 No. 10 pp. 1085-1087.
Ballard et al., "Natural and synthetic forms of insulin-like growth factor-1 (IGF-1) and the potent derivative, destripeptide IGF-1: Biological activities and receptor binding", Biochemical and Biophysical Research Communications, 1987 vol. 149 No. 2 pp. 398-404.
Brzozowski et al., "Structural Origins of the Functional Divergence of Human Insulin-Like Growth Factor-I and Insulin", Biochemistry, 2002 vol. 41 pp. 9389-9397.
Chen et al., "Novel biological activities of the fish pro-IGF-I E-peptides: studies on effects of fish pro-IGF-I E-peptide on morphological change, anchorage-dependent cell division, and invasiveness in tumor cells", General and Comparative Endocriminology, 2002 vol. 126 pp. 342-351.
Francis et al., "Insulin-like growth factor (IGF)-II binding to IGF-binding proteins and IGF receptors is modified by deletion of the N-terminal hexapeptide or substitution of arginine for glutamate-6 in IGF-11" Biochemistry Journal, 1993 vol. 293 pp. 713-719.
Hill et al., "Regulation of Insulin-Like Growth Factor I (IGF-I) Bioactivity in Vivo: Further Characterization of an IGF-I-Enhancing Antibody", Endocrinology, 1998 vol. 139 No. 3 pp. 1278-1287.

(Continued)

*Primary Examiner* — Marianne P Allen
(74) *Attorney, Agent, or Firm* — Frank Wu

(57) ABSTRACT

The invention relates to stabilized polypeptides having an IGF-1 or IGF-2 sequence and an E-peptide sequence, where the natural physiological cleavage of the E-peptide from the IGF is prevented.

16 Claims, 20 Drawing Sheets

OTHER PUBLICATIONS

Jansen et al., "Sequence of cDNA encoding human insulin-like growth factor I precursor", Nature, 1983 vol. 306 No. 8 pp. 609-611.

Jansen et al., "Effects of a single cleavage in insulin-like growth factors I and II on binding to receptors, carrier proteins and antibodies" Biochemistry Journal, 1990 vol. 266 pp. 513-520.

Pfeffer et al., "The Insulin-like Growth Factor (IGF)-I E-Peptides Modulate Cell Entry of the Mature IGF-I Protein", Molecular Biology of the Cell, 2009 vol. 20 pp. 3810-3817.

Rotwein et al., "Organization and Sequence of the Human Insulin-like Growth Factor I Gene", The Journal of Biological Chemistry, 1986 vol. 261 No. 11 pp. 4828-4832.

Tian et al., "Recombinant E-Peptides of Pro-IGF-I Have Mitogenic Activity", Endocrinology, 1999 vol. 140 pp. 3387-3390.

Chacon Heszele et al.; "Insulin-Like Growth Factor I: The Yin and Yang of Muscle Atrophy"; Endocrinology; 145 (11):4803-4805 (2004).

Fig. 7A

```
                                                                                                         SEQ ID NO
Majority                          GPETLCGAELVDALQFVCGDRGFYFNKPTGYGSSSRRAPQTGIVDECCFRSCDLRRLEMYCAPLKPAKSA  1
                                  -+---------+---------+---------+---------+---------+---------+--------
                                   50        60        70        80        90        100       110
                                  -+---------+---------+---------+---------+---------+---------+--------
Human IGF-1                       GPETLCGAELVDALQFVCGDRGFYFNKPTGYGSSSRRAPQTGIVDECCFRSCDLRRLEMYCAPLKPAKSA  1
Human IA EAW97695.1               GPETLCGAELVDALQFVCGDRGFYFNKPTGYGSSSRRAPQTGIVDECCFRSCDLRRLEMYCAPLKPAKSA  1
Human IB P05019                   GPETLCGAELVDALQFVCGDRGFYFNKPTGYGSSSRRAPQTGIVDECCFRSCDLRRLEMYCAPLKPAKSA  1
Pig ref NP_999421.1               GPETLCGAELVDALQFVCGDRGFYFNKPTGYGSSSRRAPQTGIVDECCFRSCDLRRLEMYCAPLKPAKSA  1
Pig CAA35527                      GPETLCGAELVDALQFVCGDRGFYFNKPTGYGSSSRRAPQTGIVDECCFRSCDLRRLEMYCAPLKPAKSA  1
Pig class1 ABG88023.1             GPETLCGAELVDALQFVCGDRGFYFNKPTGYGSSSRRAPQTGIVDECCFRSCDLRRLEMYCAPLKPAKSA  1
Pig class2 ABG88024.1             GPETLCGAELVDALQFVCGDRGFYFNKPTGYGSSSRRAPQTGIVDECCFRSCDLRRLEMYCAPLKPAKSA  1
Cow Hereford ref NP_001071296.1   GPETLCGAELVDALQFVCGDRGFYFNKPTGYGSSSRRAPQTGIVDECCFRSCDLRRLEMYCAPLKPAKSA  1
Cow CAA33746.1                    GPETLCGAELVDALQFVCGDRGFYFNKPTGYGSSSRRAPQTGIVDECCFRSCDLRRLEMYCAPLKPAKSA  1
Sheep ref NP_001009774.1          GPETLCGAELVDALQFVCGDRGFYFNKPTGYGSSSRRAPQTGIVDECCFRSCDLRRLEMYCAPLKAAKSA  85
Sheep ABB02295.1                  ---------LVDALQFVCGDRGFYFNKPTGYGSSSRRAPQTGIVDECCFRSCDLRRLEMYCAPLKAAKSA  86
Goat BAB77524.1                   GPETLCGAELVDALQFVCGDRGFYFNKPTGYGSSSRRAPQTGIVDECCFRSCDLRRLEMYCAPLKPTKSA  87
Goat P51457                       GPETLCGAELVDALQFVCGDRGFYFNKPTGYGSSSRRAPQTGIVDECCFRSCDLRRLEMYCAPLKPTKSA  87
Dog P33712                        GPETLCGAELVDALQFVCGDRGFYFNKPTGYGSSSRRAPQTGIVDECCFRSCDLRRLEMYCAPLKPAKSA  1
Dog IsoIB XP_866946.1             GPETLCGAELVDALQFVCGDRGFYFNKPTGYGSSSRRAPQTGIVDECCFRSCDLRRLEMYCAPLKPAKSA  1
Dog Iso2 XP_853117.1              GPETLCGAELVDALQFVCGDRGFYFNKPTGYGSSSRRAPQTGIVDECCFRSCDLRRLEMYCAPLKPAKSA  1
Dog Iso3 XP_866935.1              GPETLCGAELVDALQFVCGDRGFYFNKPTGYGSSSRRAPQTGIVDECCFRSCDLRRLEMYCAPLKPAKSA  1
Equine AAB47485.1                 GPETLCGAELVDALQFVCGDRGFYFNKPTGYGSSSRRAPQTGIVDECCFRSCDLRRLEMYCAPLKPAKSA  1
Rhesus macaque XP_001094129.1     GPETLCGAELVDALQFVCGDRGFYFNKPTGYGSSSRRAPQTGIVDECCFRSCDLRRLEMYCAPLKPAKSA  1
chimpanzee XP_001156459.1         GPETLCGAELVDALQFVCGDRGFYFNKPTGYGSSSRRAPQTGIVDECCFRSCDLRRLEMYCAPLKPAKSA  1
Tiger Q6GUL6                      GPETLCGAELVDALQFVCGDRGFYFNKPTGYGSSSRRAPQTGIVDECCFRSCDLRRLEMYCAPLKPAKSA  1
RedPanda Q6IVA5                   GPETLCGAELVDALQFVCGDRGFYFNKPTGYGSSSRRAPQTGIVDECCFRSCDLRRLEMYCAPLKPAKSA  1
GiantPanda Q6JLX1                 GPETLCGAELVDALQFVCGDRGFYFNKPTGYGSSSRRAPQTGIVDECCFRSCDLRRLEMYCAPLKPAKSA  88
RedDeer ABL98032.1                GPETLCGAELVDALQFVCGDRGSYFNKPTGYGSSSRRAPQTGIVDECCFRSCDLRRLEMYCAPLKPTKAA  89
Rabbit AAB48032.1                 GPETLCGAELVDALQFVCGDRGFYFNKPTGYGSSSRRAPQTGIVDECCFRSCDLRRLEMYCAPLKPAKAA  90
Rabbit Q95222                     GPETLCGAELVDALQFVCGDRGFYFNKPTGYGSSSRRAPQTGIVDECCFRSCDLRRLEMYCAPLKPAKAA  90
Guinea pig P17647                 GPETLCGAELVDALQFVCGDRGFYFNKPTGYGSSSRRAPQTGIVDECCFRSCDLRRLEMYCAPLKPAKSA  1
Rat ref NP_849197.1               GPETLCGAELVDALQFVCGPRGFYFNKPTGYGSSIRRAPQTGIVDECCFRSCDLRRLEMYCVRCKPTKSA  91
Rat CAA29436.1                    GPETLCGAELVDALQFVCGPRGFYFNKPTGYGSSIRRAPQTGIVDECCFRSCDLRRLEMYCAPLKPTKSA  92
Mouse Iso1 ref NP_034642.1        GPETLCGAELVDALQFVCGPRGFYFNKPTGYGSSIRRAPQTGIVDECCFRSCDLRRLEMYCAPLKPTKSA  93
Mouse Iso2 ref NP_908941.1        GPETLCGAELVDALQFVCGPRGFYFNKPTGYGSSIRRAPQTGIVDECCFRSCDLRRLEMYCAPLKPTKAA  93
Mouse AAL34535.1                  GPETLCGAELVDALQFVCGPRGFYFNKPTGYGSSIRRAPQTGIVDECCFRSCDLRRLEMYCAPLKPTKAA  93
Mouse IsoEb AAX61180.1            GPETLCGAELVDALQFVCGPRGFYFNKPTGYGSSIRRAPQTGIVDECCFRSCDLRRLEMYCAPLKPTKAA  93
chicken NP_001004384.1            GPETLCGAELVDALQFVCGDRGFYFSKPTGYGSSSRRLHHKGIVDECCFQSCDLRRLEMYCAPIKPPKSA  94
Turkey AAC26006.1                 GPETLCGAELVDALQFVCGDRGFYFSKPTGYGSSSRRLHHKGIVDECCFQSCDLRRLEMYCAPIKPPKSA  94
Japanesequail AAF67202.1          GPETLCGAELVDALQFVCGDRGFYFSKPTGYGSSSRRLHHKGIVDECCFQSCDLRRLEMYCAPIKPPKSA  94
Japanesequail P51462              GPETLCGAELVDALQFVCGDRGFYFSKPTGYGSSSRRLHHKGIVDECCFQSCDLRRLEMYCAPIKPPKSA  94
Goose ABF57993.1                  GPETLCGAELVDALQFVCGDRGFYFSKPTGYGSSSRRLHHKGIVDECCFQSCDLRRLEMYCAPIKPPKSA  94
Duck P33712                       GPETLCGAELVDALQFVCGDRGFYFNKPTGYGSSSRRAPQTGIVDECCFRSCDLRRLEMYCAPLKPAKSA  1
Duck ABA02291.1                   GPETLCGAELVDALQFVCGDRGFYFSKPTGYGSSSRRLHHKGIVDECCFQSCDLRRLEMYCAPIKPPKSA  94
Salmon AAA67268.1                 GPETLCGAELVDTLQFVCGERGFYFSKPTGYGPSSRRSHNRGIVDECCFQSCELRRLEMYCAPVKSGKAA  95
Salmon AAA67267.1                 GPETLCGAELVDTLQFVCGERGFYFSKPTGYGPSSRRSHNRGIVDECCFQSCELRRLEMYCAPVKSGKAA  95
Sterlet ABC54785.1                GSETLCGAELVDTLQFVCGERGFYFNKPTGYGASSRRPHHRGIVNECCFQSCDLRRLEMYCAPVKPAKAS  96
Perch CAE52916.2                  GPETLCGAELVDTLQFVCGERGFYFSKPTGYGPNARRS--RGIVDECCFQSCELRRLEMYCAPAKTSKAA  97
Trout Q02815                      GPETLCGAELVDTLQFVCGERGFYFSKPTGYGPSSRRSHNRGIVDECCFQSCELRRLEMYCAPVKSGKAA  98
Halibut CAA09267.1                GPETLCGAELVDTLQFVCGERGFYFSKPTGYGPNARRS--RGIVDECCFQSCELRRLEMYCAPAKTSKAA  97
Catfish AAQ56592.1                GPETLCGAELVDTLQFVCGDRGFYFSKPTGYGPNSRRSHNRGIVDECCFQSCELRRLEMYCAPVKSGKAP  99
Carp AAY21902.1                   GPETLCGAELVDTLQFVCGDRGFYFSKPTGYGPSSRRSHNRGIVDECCFQSCELRRLEMYCAPVKPGKTP  100
Carp AAP78926.1                   GPETLCGAELVDTLQFVCGDRGFYFSKPTGYGPSSRRSHNRGIVDECCFQSCELRRLEMYCAPVKPGKTP  100
GiantDanio ABB05519.1             GPETLCGAELVDTLQFVCGDRGFYFSKPTGYGPSSRRSHNRGIVDECCFQSCELRRLEMYCAPVKTGKTP  101
Zebrafish NP_571900.1             GPETLCGAELVDTLQFVCGDRGFYFSKPTGYGPSSRRSHNRGIVDECCFQSCELRRLEMYCAPVKTGKSP  102
Chinese sucker ABH12114.1         GPETLCGAELVDTLQFVCGDRGFYFSKPTGYGPSSRRSHNRGIVDECCFQSCELRRLEMYCAPVKPGKAP  103
SpinyBarbus ABE03747.1            GPETLCGAELVDTLQFVCGDRGFYFSKPTGYGPSSRRSHNRGIVDECCFQSCELRRLEMYCAPVKPGKTP  100
FatheadMinnow AAT02176.1          GPETLCGAELVDTLQFVCGDRGFYFNKPAGYGSNSRRSNNYGIVDECCFQSCELRRLEMYCAPVKTGKTP  104
GoldFish AAC83443.1               GPETLCGAELVDTLQFVCGDRGFYFSKPTGYGPNSRRSHNRGIVDECCFQSCELRRLEMYCAPVKPGKTP  105
Frog AAA70330.1                   GPETLCGAELVDTLQFVCGDRGFYFSKPTGYGSNNRRSHHRGIVDECCFQSCDFRRLEMYCAPAKPAKSA  106
Bream AAK16727.1                  GPETLCGAELVDTLQFVCGDRGFYFSKPTGYGPSSRRSHNRGIVDECCFQSCELRRLEMYCAPVKTGKTP  101
Frog 1a P16501                    GPETLCGAELVDTLQFVCGDRGFYFSKPTGYGSNNRRSHHRGIVDECCFQSCDFRRLEMYCAPAKQAKSA  107
RhesusMacque XP_001093911.1       GPETLCGAELVDALQFVCGDRGFYFNKPTGYGSSSRRAPQTGIVDECCFRSCDLRRLEMYCAPLKPAKSA  1
Opossum XP_001373491.1            GPETLCGAELVDALQFVCGERGFYFSKPTGYGSSSRRLHHTGIVDECCFRSCDLRRLEMYCAPIKPAKSA  108
Pig AAT47735.1                    GPETLCGAELVDALQFVCGDRGFYFNKPTGYGSSSRRAPQTGIVDECCFRSCDLRRLEMYCAPLKPAKSA  1
```

Fig. 8A

```
                                                               SEQ ID NO
Majority                            RSVRAQRHTDMPKAQKEVHLKNTSRGSTGNKNYRM 109
                                    ---------+---------+---------+-----
                                             10        20        30
                                    ---------+---------+---------+-----
Human Ea                            RSVRAQRHTDMPKTQKEVHLKNASRGSAGNKNYRM 2
Pig ref NP_999421.1                 RSVRAQRHTDMPKAQKEVHLKNTSRGSSGNKNYRM 109
Pig CAA35527                        RSVRAQRHTDMPKAQKEVHLKNTSRGSSGNKNYRM 109
Pig class1 ABG88023.1               RSVRAQRHTDMPKARKEVHLKNTSRGSSGNKNYRM 110
Pig class2 ABG88024.1               RSVRAQRHTDMPKARKEVHLKNTSRGSSGNKNYRM 110
Cow Hereford ref NP_001071296.1     RSVRAQRHTDMPKAQKEVHLKNTSRGSAGNKNYRM 111
Cow CAA33746.1                      RSVRAQRHTDMPKAQKEVHLKNTSRGSAGNKNYRM 111
Sheep ref NP_001009774.1            RSVRAQRHTDMPKAQKEVHLKNTSRGSAGNKNYRM 111
Sheep ABB02295.1                    RSVRAQRHTDMPKAQKEVHLKNTSRGSAGNKNYRM 111
Goat BAB77524.1                     RSVRAQRHTDMPKAQKEVHLKNTSRGSAGNKNYRM 111
Goat P51457                         RSVRAQRHTDMPKAQKEVHLKNTSRGSAGNKNYRM 111
Dog P33712                          RSVRAQRHTDMPKAQKEVHLKNASRGSAGNKTY   112
Dog Iso2 XP_853117.1                RSVRAQRHTDMPKAQKEVHLKNASRGSAGNKNYRM 113
Dog Iso3 XP_866935.1                RSVRAQRHTDMPKAQKEVHLKNASRGSAGNKNYRM 113
Equine AAB47485.1                   RSVRAQRHTDMPKAQKEVHLKNTSRGSAGNKNYRM 111
Rhesus macaque XP_001094129.1       RSVRAQRHTDMPKTQKEVHLKNASRGSAGNKNYRM 2
Tiger Q6GUL6                        RSVRAQRHTDMPKAQKEVHLKNASRGSAGNKNYRM 113
RedPanda Q6IVA5                     RSVRAQRHTDMPKAQKEVHLKNASRGSAGNKNYRM 113
GiantPanda Q6JLX1                   RSVRAQRHTDMPKAQKEVHLKNASRGSAGNKNYRM 113
RedDeer ABL98032.1                  RSVRAQRHTDMPKAQKEVHLKNTSRGSAGNKNYRM 111
Rabbit AAB48032.1                   RSVRAQRHTDMPKTQKEVHLKNTSRGSAGNKNYRM 114
Guinea pig P17647                   RSVRAQRHTDMPKTQKEVHLKNASRGSAGNKNYRM 2
Rat ref NP_849197.1                 RSIRAQRHTDMPKTQKEVHLKNTSRGSAGNKTYRM 115
Rat CAA29436.1                      RSIRAQRHTDMPKTQKEVHLKNTSRGSAGNKTYRM 115
Mouse AAL34535.1                    RSIRAQRHTDMPKTQKEVHLKNTSRGSAGNKTYRM 115
chicken NP_001004384.1              RSVRAQRHTDMPKAQKEVHLKNTSRGNTGNRNYRM 116
Turkey AAC26006.1                   RSVRAQRHTDMPKAQKELHLKNTSRGNTGNRNYRM 117
Japanesequail AAF67202.1            RSVRAQRHTDMPKAQKEVHLKNTSRGNTGNRNYRM 116
Japanesequail P51462                RSVRAQRHTDMPKAQKEVHLKNTSRGNTGNRNYRM 116
Goose ABF57993.1                    RSVRAQRHTDMPKAQKEVHLKNTSRGNTEN      118
Duck P33712                         RSVRAQRHTDMPKAQKEVHLKNASRGSAGNKTY   112
Salmon AAA67268.1                   RSVRAQRHTDMPRTPKEVHQKNSSRGNTGGRNYRM 119
Salmon AAA67267.1                   RSVRAQRHTDMPRTPKEVHQKNSSRGNTGGRNYRM 119
Sterlet ABC54785.1                  RSVRAQRHTDMPKAQKEVHSKNSSRGNTGNRNYRI 120
Perch CAE52916.2                    RSVRAQRHTDMPRAPKEVHQKNSSRGNTGGRNYRM 121
Trout Q02815                        RSVRAQRHTDMPRTPKEVHQKNSSRGNTGGRNYRM 119
Halibut CAA09267.1                  RSVRAQRHTDMPRAPKEVHQKNSSRGTTGGRNYRM 122
Catfish AAQ56592.1                  RSVREQRHTDTPKTPKEVHQKNSSRGNTGGRNYRM 123
Carp AAY21902.1                     RSIRAQRHTDSPKTAKEVHQKNSSRGNTGGRNYRM 124
Carp AAP78926.1                     RSVRAQRHTDSPRTAKEVHQKNSSRGNTGGRNYRI 125
GiantDanio ABB05519.1               RSLRAQRHTDIPRTAKEVHQKNSSRGNTGGRNYRM 126
Zebrafish NP_571900.1               RSLRAQRHTDIPRTPKEVHQKNSSRGNTGGRNYRM 127
Chinese sucker ABH12114.1           RSLRAQRHTDIPRTPKDVHQKNSSRGNTGGRNYRM 128
SpinyBarbus ABE03747.1              RSLRAQRHTDSPRTAKEVHQKNSSRGNTGGRNYRI 129
FatheadMinnow AAT02176.1            RSLRAQRHTDITRTAKEVHQKNSSRGITGGRNYRM 130
GoldFish AAC83443.1                 RSLRAQRHTDGTRTAKEVHQKNSSRGNTGGRNYRM 131
Frog AAA70330.1                     RSVRAQRHTDMPKAQKEVHPKNTSRGNTGSRGFRM 132
Bream AAK16727.1                    RSLRAQRHTDITRTAKEVHQKNSSRGNTGGRNYRI 133
Frog 1a P16501                      RSVRTQRHTDMPKAQKEVHPKNTSRGNTGSRGFRM 134
```

Fig. 9A

```
Majority                        ----RSVRAQRHTDMPKTQKYQPPSTNKKTKSQRRRKGGPKTHPGGEQKE--------------------------
                                ---------+---------+---------+- --------+---------+---------+---------+-----
                                         10        20        30         40        50        60        70
                                ---------+---------+---------+- --------+---------+---------+---------+-----
human Eb                        ----RSVRAQRHTDMPKTQKYQPPSTNKNTKSQRR-KGWPKTHPGGEQKEGTEASLQIRGKKKEQRREIGSRNAECRGKK
Human P05019                    ----RSVRAQRHTDMPKTQKYQPPSTNKNTKSQRR-KGWPKTHPGGEQKEGTEASLQIRGKKKEQRREIGSRNAECRGKK
Pig AAT47735.1                  ----RSVRAQRHTDMPKAQKYQPPSTNKKTKSQRRRKGS--TFEEHK
Cow India AAU93628.1            --------------------YQPPSTNKKMKSQRRRKGGPKKRPGGEQKE
Cattle AAA03497.1               HAQGSEGKPARGGGEGRPSSYQPPSTNKKMKSQRRRKGGPKKRPGGEQKE
Water Buffalo AAU93630.1        --------------------YQPPSTNKKMKSQRRRKGGPKKHPGGEQKE
Sheep AAU93626.1                --------------------YQLPSTNKKMKSQRRRKGGPKKHPGGEQKE
Dog XP_866946.1                 ----RSVRAQRHTDMPKAQKYHPPSTTKRMKSQRRRKGS--TFEECK
Rabbit Q95222                   ----RSVRAQRHTDMPKTQKYQPPSTNKKMKSQRRRKGS--TFEEHK
Chimpanzee XP_001156459.1       ----RSVRAQRHTDMPKTQKYQPPSTNKNTKSQRRRKGGPKTHPGGEQKEGTEASLQIRGKKKEQRREIGSRNAECRGKK
Rhesus monkey XP_001093911.1    ----RSVRAQRHTDMPKTQKYQPPSTNKNTKSQRRRKGGPKTHPGGEQKEGTEASLQIRGKKKEQRREIGSRNAECRGKK
Mouse NP_908941.1               ----RSIRAQRHTDMPKTQKSPSLSTNKKTKLQRRRKGEPKTHPGCEQEEVTEATRKIRGPREKRLG
Rat AAA41214.1                  ----RSIRAQRHTDMPKTQKSQPLSTHKKRKLQRRRKGESKAHPGGEQEEGAEATQKIRGDRERRPS
Mouse AAX61180.1                ----RSIRAQRHTDMPKTQKSPSLSTNKKTKLQRRRKGS--TFEEHK
```

|  | | SEQ ID NO |
|---|---|---|
|  | | 135 |
| Majority | | -- |
|  | | -- |
| Human Eb | GK | 3 |
| Human P05019 | GK | 3 |
| Pig AAT47735.1 | | 136 |
| Cow India AAU93628.1 | | 137 |
| Cattle AAA03497.1 | | 138 |
| Water Buffalo AAU93630.1 | | 139 |
| Sheep AAU93626.1 | | 140 |
| Dog XP_866946.1 | | 141 |
| Rabbit Q95222 | | 142 |
| Chimpanzee XP_001156459.1 | GK | 143 |
| Rhesus monkey XP_001093911.1 | GKWRTGGLSRQRQG | 144 |
| Mouse NP_908941.1 | | 145 |
| Rat AAA41214.1 | | 146 |
| Mouse AAX61180.1 | | 147 |

Fig. 10A

|  |  | SEQ ID NO |
|---|---|---|
| Majority | RSVRAQRHTDMPKTQKYQPPSTNKKTKSQRRRKGSTFEEH- | 148 |
|  | ---------+---------+---------+- --------+ |  |
|  | 10        20        30       40 |  |
|  | ---------+---------+---------+- --------+ |  |
| human Ec | RSVRAQRHTDMPKTQKYQPPSTNKNTKSQRR-KGSTFEERK | 4 |
| Human EAW97695.1 | RSVRAQRHTDMPKTQKYQPPSTNKNTKSQRR-KGSTFEER | 149 |
| Human AAA96152.1 | RSVRAQRHTDMPKTQKYQPPSTNKNTKSQRR-KGSTFEER | 149 |
| Pig AAT47735.1 | RSVRAQRHTDMPKAQKYQPPSTNKKTKSQRRRKGSTFEEH | 150 |
| Dog Ib XP_866946.1 | RSVRAQRHTDMPKAQKYHPPSTTKRMKSQRRRKGSTFEEC | 151 |
| Rabbit Q95222 | RSVRAQRHTDMPKTQKYQPPSTNKKMKSQRRRKGSTFEEH | 152 |
| Rhesus monkey XP_001094016.1 | RSVRAQRHTDMPKTQKYQPPSTNKNTKSQRRRKGSTFEER | 153 |
| Mouse Ib AAX61180.1 | RSIRAQRHTDMPKTQKSPSLSTNKKTKLQRRRKGSTFEEH | 154 |
| Mouse Iso1 NP_034642.1 | RSIRAQRHTDMPKTQKSPSLSTNKKTKLQRRRKGSTFEEH | 154 |
| Rat Ib A40912 | RSIRAQRHTDMPKTQKSQPLSTHKKRKLQRRRKGSTLEEH | 155 |
| Rat Ib A26859 | RSIRAQRHTDMPKTQKSQPLSTHKKRKLQRRRKGSTLEEH | 155 |

Fig. 11A

```
Majority                      AYRPSETLCGGELVDTLQFVCGDRGFYFS-----------RPAS-RVNRRS--RGIVEECCFRSCDLALLETYCATPAK
                              ---------+---------+---------+-   --   ------   +---------+---------+-----
                                       10        20        30                    40        50        60
                              ---------+---------+---------+-   --   ------   +---------+---------+-----
Human IGF-2                   AYRPSETLCGGELVDTLQFVCGDRGFYFSRP---------AS----RVSRRS--RGIVEECCFRSCDLALLETYCATPAK
Human NP_000603.1             AYRPSETLCGGELVDTLQFVCGDRGFYFSRP---------AS----RVSRRS--RGIVEECCFRSCDLALLETYCATPAK
Pig NP_999048.1               AYRPSETLCGGELVDTLQFVCGDRGFYFS-----------RPAS-RVNRRS--RGIVEECCFRSCDLALLETYCATPAK
Cattle NP_776512.2            AYRPSETLCGGELVDTLQFVCGDRGFYFS-----------RPSS-RINRRS--RGIVEECCFRSCDLALLETYCATPAK
Sheep NP_001009311.1          AYRPSETLCGGELVDTLQFVCGDRGFYFS-----------RPSS-RINRRS--RGIVEECCFRSCDLALLETYCAAPAK
Dog Iso1 XP_540785.2          AYRPSETLCGGELVDTLQFVCGDRGFYFS-----------RPAS-RVTRRSS-RGIVEECCFRSCDLALLETYCATPAK
Dog Iso2 XP_851137.1          AYRPSETLCGGELVDTLQFVCGDRGFYFSDL---------SRPAS-RVTRRSS-RGIVEECCFRSCDLALLETYCATPAK
Dog Iso3 XP_863200.1          AYRPSETLCGGELVDTLQFVCGDRGFYFSDAALLPPVGLPGRPAS-RVTRRSS-RGIVEECCFRSCDLALLETYCATPAK
RedJungleFowl XP_421026.2     AYGTAETLCGGELVDTLQFVCGDRGFYFS-----------RPVG-RNNRRIN-RGIVEECCFRSCDLALLETYCAKSVK
Rat NP_113699.1               AYRPSETLCGGELVDTLQFVCSDRGFYFS-----------RPSS-RANRRS--RGIVEECCFRSCDLALLETYCATPAK
Mouse NP_034644.1             AYGPGETLCGGELVDTLQFVCSDRGFYFS-----------RPSS-RANRRS--RGIVEECCFRSCDLALLETYCATPAK
Chimpanzee XP_001153640.1     AYRPSETLCGGELVDTLQFVCGDRGFYFSKA---------STPAAFPITRPL--RRVGQRCCRGGCPPADLRDASAFPRR
Zebrafish Iso1 XP_001338042.1 EVASAETLCGGELVDALQFVCEDRGFYFS-----------RPTSRSNSRRSQNRGIVEECCFSSCNLALLEQYCAKPAK
Zebrafish Iso2a NP_001001815.1 EVASAETLCGGELVDALQFVCEDRGFYFS-----------RPTSRSNSRRSQNRGIVEECCFSSCNLALLEQYCAKPAK
Zebrafish Iso2b NP_571508.1   NVTAGETLCGGELVDTLQFVCGEDGFYIS-----------RPN-RSNSRRPQ-RGIVEECCFRSCELHLLQQYCAKPVK Majority                      SERDVSTP--------PTVLPDNFPRYPVGKFFQYDTW-KQSAQRLRRGLPALLRARRGRMLAKELEAFREAKR-HRPLI
                              ----+---    ------+---------+-----  ----+---------+---------+---------+ -----
                                  70               80        90         100       110       120       130
                              ----+---    ------+---------+-----  ----+---------+---------+---------+ -----
Human IGF-2           SERDVSTP--------PTVLPDNFPRYPVGKFFQYDTW-KQSTQRLRRGLPALLRARRGHVLAKELEAFREAKR-HRPLI
Human NP_000603.1             SERDVSTP--------PTVLPDNFPRYPVGKFFQYDTW-KQSTQRLRRGLPALLRARRGHVLAKELEAFREAKR-HRPLI
Pig NP_999048.1               SERDVSTP--------PTVLPDNFPRYPVGKFFRYDTW-KQSAQRLRRGLPALLRARRGRTLAKELEAVREAKR-HRPLT
Cattle NP_776512.2            SERDVSAS--------TTVLPDDVTAYPVGKFFQYDIW-KQSTQRLRRGLPAFLRARRGRTLAKELEALREAKS-HRPLI
Sheep NP_001009311.1          SERDVSAS--------TTVLPDDFTAYPVGKFFQSDTW-KQSTQRLRRGLPAFLRARRGRTLAKELEALREAKS-HRPLI
Dog Iso1 XP_540785.2          SERDVSTP--------PTVLPDNFPRYPVGKFFQYDTW-KQSAQRLRRGLPALLRARRGRMLAKELEAFREAKR-HRPLI
Dog Iso2 XP_851137.1          SERDVSTP--------PTVLPDNFPRYPVGKFFQYDTW-KQSAQRLRRGLPALLRARRGRMLAKELEAFREAKR-HRPLI
Dog Iso3 XP_863200.1          SERDVSTP--------PTVLPDNFPRYPVGKFFQYDTW-KQSAQRLRRGLPALLRARRGRMLAKELEAFREAKR-HRPLI
RedJungleFowl XP_421026.2     SERDLSATSLAGL---PALNKESFQKPSHAKYSKYNVWQKKSSQRLQREVPGILRARRYRWQAEGLQAAEEEARAMHRPLI
Rat NP_113699.1               SERDVSTS--------QAVLPDDFPRYPVGKFFKFDTW-RQSAGRLRRGLPALLRARRGRMLAKELEAFREAKR-HRPLI
Mouse NP_034644.1             SERDVSTS--------QAVLPDDFPRYPVGKFFQYDTW-RQSAGRLRRGLPALLRARRGRMLAKELKEFREAKR-HRPLI
Chimpanzee XP_001153640.1     ESRHLLTS--------PFPSQDNFPRYPVGKFFQSDTW-KQSTQRLRRGLPALLRARRGHMLAKELEAFREAKR-HRPLI
Zebrafish Iso1 XP_001338042.1 SERDVSATSLQVIPVMPALKQEVPRKHVTVKYSKYDVWQRKAAQRLRRGIPAILRAKKFFRRQAERIKAQEQLLH-HRPLI
Zebrafish Iso2a NP_001001815.1 SERDVSATSLQVIPVMPALKQEVPRKHVTVKYSKYDVWQRKAAQRLRRGIPAILRAKKFFRRQAERIKAQEQLLH-HRPLI
Zebrafish Iso2b NP_571508.1   SERDVSSTSLQVFPVSQALHKDT----INVKYSKYEVWQQKAAQRLRRGVPSILLARKFRRQMEKIQDEEQTSF-HRPLM SEQ ID NO
Majority                      ALPTQDPA-HGGASPEASSNRK---  156
                              ----+---  ------+---------
                                  140         150
                              ----+---  ------+---------
Human IGF-2                   ALPTQDPA-HGGAPPEMASNRKAYR   7
Human NP_000603.1             ALPTQDPA-HGGAPPEMASNRK     157
Pig NP_999048.1               ARPTRDPAAHGGASPEASGHRK     158
Cattle NP_776512.2            ALPTQDPATHGGASSKASSD       159
Sheep NP_001009311.1          ALPTQDPATHGGASSEASSD       160
Dog Iso1 XP_540785.2          ALPTHDPATHGGASPEASGNQK     161
Dog Iso2 XP_851137.1          ALPTHDPATHGGASPEASGNQK     162
Dog Iso3 XP_863200.1          ALPTHDPATHGGASPEASGNQK     163
RedJungleFowl XP_421026.2     SLPSQRPP-APRASPEATGPQE     164
Rat NP_113699.1               VLPPKDPA-HGGASSEMSSNHQ     165
Mouse NP_034644.1             VLPPKDPA-HGGASSEMSSNHQ     166
Chimpanzee XP_001153640.1     ALPTQDPA-HGGAPPEMASNRK     167
Zebrafish Iso1 XP_001338042.1 TLPSKLPP--ILLPTENYVSHK     168
Zebrafish Iso2a NP_001001815.1 TLPSKLPP--ILLPTENYVSHK    169
Zebrafish Iso2b NP_571508.1   TLPNRQPA--IVPHVQISTSRK     169
```

Fig. 12A

```
Majority                            RDVSTP--------PTVLPDNFPRYPVGKFFQYDTW-KQSAQRLRRGLPALLRARRGRMLAKELEAFREAKR-HRPLIAL
                                    --+---   ------+---------+-----   ----+---------+---------+---------+  -------
                                         70        80        90        100       110       120       130
                                    --+---   ------+---------+------  ----+---------+---------+---------+  -------
Human IGF-2                         RDVSTP--------PTVLPDNFPRYPVGKFFQYDTW-KQSTQRLRRGLPALLRARRGHVLAKELEAFREAKR-HRPLIAL
Human NP_000603.1                   RDVSTP--------PTVLPDNFPRYPVGKFFQYDTW-KQSTQRLRRGLPALLRARRGHVLAKELEAFREAKR-HRPLIAL
Pig NP_999048.1                     RDVSTP--------PTVLPDNFPRYPVGKFFRYDTW-KQSAQRLRRGLPALLRARRGRTLAKELEAVREAKR-HRPLTAR
Cattle NP_776512.2                  RDVSAS--------TTVLPDDVTAYPVGKFFQYDIW-KQSTQRLRRGLPAFLRARRGRTLAKELEALREAKS-HRPLIAL
Sheep NP_001009311.1                RDVSAS--------TTVLPDDFTAYPVGKFFQSDTW-KQSTQRLRRGLPAFLRARRGRTLAKELEALREAKS-HRPLIAL
Dog Iso1 XP_540785.2                RDVSTP--------PTVLPDNFPRYPVGKFFQYDTW-KQSAQRLRRGLPALLRARRGRMLAKELEAFREAKR-HRPLIAL
Dog Iso2 XP_851137.1                RDVSTP--------PTVLPDNFPRYPVGKFFQYDTW-KQSAQRLRRGLPALLRARRGRMLAKELEAFREAKR-HRPLIAL
Dog Iso3 XP_863200.1                RDVSTP--------PTVLPDNFPRYPVGKFFQYDTW-KQSAQRLRRGLPALLRARRGRMLAKELEAFREAKR-HRPLIAL
RedJungleFowl XP_421026.2           RDLSATSLAGL---PALNKESFQKPSHAKYSKYNVWQKKSSQRLQREVPGILRARRYRWQAEGLQAAEEARAMHRPLISL
Rat NP_113699.1                     RDVSTS--------QAVLPDDFPRYPVGKFFKFDTW-RQSAGRLRRGLPALLRARRGRMLAKELEAFREAKR-HRPLIVL
Mouse NP_034644.1                   RDVSTS--------QAVLPDDFPRYPVGKFFQYDTW-RQSAGRLRRGLPALLRARRGRMLAKELKEFREAKR-HRPLIVL
Chimpanzee XP_001153640.1           RHLLTS--------PFPSQDNFPRYPVGKFFQYDTW-KQSTQRLRRGLPALLRARRGHMLAKELEAFREAKR-HRPLIAL
Zebrafish Iso1 XP_001338042.1       RDVSATSLQVIPVMPALKQEVPRKHVTVKYSKYDVWQRKAAQRLRRGIPAILRAKKFRRQAERIKAQEQLLH-HRPLITL
Zebrafish Iso2a NP_001001815.1      RDVSATSLQVIPVMPALKQEVPRKHVTVKYSKYDVWQRKAAQRLRRGIPAILRAKKFRRQAERIKAQEQLLH-HRPLITL
Zebrafish Iso2b NP_571508.1         RDVSSTSLQVFPVSQALHKDT----INVKYSKYEVWQQKAAQRLRRGVPSILLARKFRRQMEKIQDEEQTSF-HRPLMTL SEQ ID NO
Majority                            PTQDPA-HGGASPEASSNRK     170
                                    --+---  ------+------
                                       140        150
                                    --+---  ------+------
Human IGF-2                         PTQDPA-HGGAPPEMASNRK     6
Human NP_000603.1                   PTQDPA-HGGAPPEMASNRK     6
Pig NP_999048.1                     PTRDPAAHGGASPEASGHRK     171
Cattle NP_776512.2                  PTQDPATHGGASSKASSD       172
Sheep NP_001009311.1                PTQDPATHGGASSEASSD       173
Dog Iso1 XP_540785.2                PTHDPATHGGASPEASGNQK     174
Dog Iso2 XP_851137.1                PTHDPATHGGASPEASGNQK     174
Dog Iso3 XP_863200.1                PTHDPATHGGASPEASGNQK     174
RedJungleFowl XP_421026.2           PSQRPP-AFRASPEATGPQE     175
Rat NP_113699.1                     PPKDPA-HGGASSEMSSNHQ     176
Mouse NP_034644.1                   PPKDPA-HGGASSEMSSNHQ     177
Chimpanzee XP_001153640.1           PTQDPA-HGGAPPEMASNRK     178
Zebrafish Iso1 XP_001338042.1       PSKLPP--ILLPTENYVSHK     179
Zebrafish Iso2a NP_001001815.1      PSKLPP--ILLPTENYVSHK     179
Zebrafish Iso2b NP_571508.1         PNRQPA--IVPHVQISTSRK     180
```

STABILIZED INSULIN-LIKE GROWTH FACTOR POLYPEPTIDES

This application is a U.S. National Phase filing of International Application Serial No. PCT/US2007/070468 filed 6 Jun. 2007, and claims priority to U.S. Provisional Application Ser. Nos. 60/812,349 filed 9 Jun. 2006, 60/862,244 filed 20 Oct. 2006, and 60/897,187 filed 24 Jan. 2007, the contents of which are incorporated herein by reference in their entirety.

BACKGROUND OF THE INVENTION

Insulin-like growth factors (IGFs) are part of a complex system that cells use to communicate with their physiologic environment. This complex system (often referred to as the insulin-like growth factor axis) consists of two cell-surface receptors (IGF-1R and IGF-2R), two ligands (IGF-1 and IGF-2), a family of six high-affinity IGF-binding proteins (IGFBP 1-6), and associated IGFBP degrading enzymes (proteases). This system is important not only for the regulation of normal physiology but also for a number of pathological states (Glass, Nat Cell Biol 5:87-90, 2003).

The IGF axis has been shown to play roles in the promotion of cell proliferation and the inhibition of cell death (apoptosis). IGF-1 is mainly secreted by the liver as a result of stimulation by human growth hormone (hGH). Almost every cell in the human body is affected by IGF-1, especially cells in muscles, cartilage, bones, liver, kidney, nerves, skin and lungs. In addition to the insulin-like effects, IGF-1 can also regulate cell growth. IGF-1 and IGF-2 are regulated by a family of gene products known as the IGF-binding proteins. These proteins help to modulate IGF action in complex ways that involve both inhibiting IGF action by preventing binding to the IGF receptors as well as promoting IGF action through aiding delivery to the receptors and increasing IGF half life in the blood stream. There are at least six characterized binding proteins (IGFBP 1-6).

In its mature form, human IGF-1 (gpetlcgaelvdalqfvcgdrgfyfnkptgygsssrrapqtgivdeccfrscdlrrlem ycaplkpaksa; SEQ ID NO:1), also called somatomedin, is a small protein of 70 amino acids that has been shown to stimulate growth of a wide range of cells in culture. The mature protein is initially encoded by three known splice variant mRNAs. The open reading frame of each mRNA encodes a precursor protein containing the 70 amino acid IGF-1 and a particular E-peptide at the C-terminus, depending on the particular IGF-1 mRNA. These E-peptides have been termed the Ea (rsvraqrhtdmpktqkevhlknasrgsagnknyrm; SEQ ID NO:2), Eb (rsvraqrhtdmpktqkyqppstnknt ksqrrkgwpkthpggeqkegteaslqirgkkkeqrreigsrnaecrgkkgk; SEQ ID NO:3), and Ec (rsvraqrhtdm pktqkyqppstnkntksqrrkgstfeerk; SEQ ID NO:4) peptides and range from 35 to 87 amino acids in length and encompass a common sequence region at the N-terminus and a variable sequence region at the C-terminus. For example, the wild-type open reading frame for the IGF-1-Ea encodes a polypeptide of 105 amino acids (gpetlcgaelvdalqfvcgdrgfyfnkptgygsssrrapqtgivde ccfrscdlrrlemycaplkpaksa rsvraqrhtdmpktqkevhlknasrgsagnknyrm; SEQ ID NO:5). In physiological expression, the E-peptides are cleaved off of the precursor by endogenous proteases to yield the mature 70 amino acid IGF-1 known to be bioactive. In certain contexts, one to three of the N-terminal amino acids of IGF-1 are known to be cleaved under physiological conditions, yielding active IGF-1 having between 67-70 amino acids. IGF-2 gene expression and processing is characterized by similar attributes except that only one E-peptide (rdvstpptvlpdnfprypvgkffqydtwkqstqrlr-rglpallrarrghvlakeleafreakrhrplialptqdpahggappemasnrk; SEQ ID NO:6) for human IGF-2 has been identified for the 156 amino acid precursor (ayrpsetlcggelvdtlqfvcgdrgfyfsrpasrvsrrsrgiveeccfrscdlal-letycatpakserdvstpptvlpdnfprypvgkffqy dtwkqstqrlrrglpall-rarrghvlakeleafreakrhrplialptqdpahggappemasnrk; SEQ ID NO:7). Both IGF-1 and IGF-2 appear to be poor drug candidates, since these proteins are quickly degraded by endogenous proteases in the serum of patients. One strategy that has been contemplated is to stabilize IGF-1 as a drug by forming a complex with one of its binding proteins.

SUMMARY OF THE INVENTION

The invention is based on the discovery that a precursor IGF-1 or IGF-2 protein containing substantially its E-peptide is bioactive and stabilized in the presence of serum, resulting in an IGF-1 or IGF-2 polypeptide that is useful as a pharmaceutical. In the compositions of the invention, the normal cleavage of the E-peptide from IGF-1 is avoided, for example, by mutating or deleting either of the arginine at position 1 or the serine at position 2 of the E-peptides (corresponding to positions 71 and 72 in the wild-type precursor IGF-1). In IGF-2, the cleavage is avoided, for example, by mutating or deleting either the arginine at position 1 or the aspartic acid at position 2 of the E-peptide (corresponding to positions 68 and 69 in the wild-type precursor IGF-2). Other modifications of an IGF precursor protein can avoid or reduce this cleavage.

In addition, further modifications of the IGF-1 precursor amino acid sequence can confer additional pharmaceutical benefits. For example, the polypeptides of the invention can exhibit increased affinity for the IGF-1 receptor or decreased binding ability to an inhibitory IGF-1 or IGF-2 binding protein.

For the sake of clarity and consistency, the numbering of amino acid residues in IGF-1 or IGF-2 precursor or mature proteins throughout this application and in the claims is based on the wild-type precursor protein sequence numbering without signal peptide.

Accordingly, the invention includes a polypeptide containing a human IGF-1 precursor protein, where the cleavage of the E-peptide from IGF-1 by a protease is reduced by modification of the precursor protein. The E-peptide can be the Ea, Eb, or Ec peptide. At the N-terminus of the precursor, amino acids G1, P2, or E3 of the precursor protein can be deleted or mutated, as can R36 (e.g., R36A) and R37 (e.g., R37A).

The precursor protein can further include the N-linked glycosylation consensus sequence NXS/T, for example by insertion of amino acids 93-102 of Ea between amino acids N95 and T96 of the Eb. In general, the precursor protein can include an oligosaccharide covalently linked to an amino acid side chain of the precursor protein, such as an arginine side chain of the precursor protein.

In addition, a residue of the precursor protein can be replaced by a non-natural amino acid (e.g., one that includes an acetylene or azido group). Such non-natural amino acids can facilitate linkage of a poly(ethylene glycol) moiety to a side-chain of the precursor protein, though typical protein pegylation strategies are well known in the art.

The precursor protein can further include one or more additional E-peptides linked to the C-terminus of the precursor protein. For example, a polypeptide can include, from N-terminus to C-terminus, (1) an IGF-1 precursor protein having a first Eb peptide, where G1, P1, and E1 are deleted, either R36 or R37 or both are mutated, R71 and S72 are deleted, and the last seven C-terminal amino acids of the first Eb peptide are deleted; (2) a second Eb peptide, where R71, S72, and the last seven C-terminal amino acids of the second Eb peptide are deleted; (3) a third Eb peptide, where R71, S72, and the last seven C-terminal amino acids of the third Eb peptide are deleted; and (4) a fourth Eb peptide, where R71 and S72 are deleted.

An effective means of preventing cleavage of the E-peptide from the IGF-1 is the deletion or mutation of R71 or S72.

Similarly, the invention includes a human IGF-2 precursor protein where the cleavage of the E-peptide from IGF-2 by a protease is reduced by modification of the precursor protein. In particular, deletion or mutation of R68 or D69 can be an effective means of avoiding protease digestion of the IGF-2 precursor protein.

In addition, any E-peptide of IGF-1 can be combined with an IGF-2 and any E-peptide of IGF-2 can be combined with IGF-1 to provide the benefits described herein.

The invention further includes a method of treating a musculoskeletal disease, diabetes, neuronal cell death by administering a therapeutically effective amount of a polypeptide of the invention. Likewise, the invention includes the use of a polypeptide of the invention for the manufacture of a medicament for the treatment of a musculoskeletal disease, diabetes, neuronal cell death, or anemia.

In another embodiment, the invention includes a pegylated IGF-1 without an E-peptide but having introduced therein a non-natural amino acid as the site of pegylation. Any of the modified, pegylated IGF-1 containing a non-natural amino acid as disclosed herein, without an E-peptide, is also included in the invention.

The invention also includes veterinary methods and uses of administering an effective amount of the polypeptide of the invention to obtain a desired effect.

The veterinary uses include (i) enhancing the rate and/or extent of growth in an animal, (ii) enhancing the efficiency of their conversion of feed into body tissue, (iii) enhancing milk production in lactating animals, (iv) treating animal wasting symptoms associated with cachexia, trauma, or other consumption diseases, and (v) treating lactating animals for improvement in neonatal health.

All cited references or documents are hereby incorporated by reference.

BRIEF DESCRIPTION OF THE DRAWINGS

FIG. 1A shows the Western blot results (using antibody to IGF-1) for the wild-type and 3mut precursor containing Ea. FIG. 1B shows the Western blot results (using antibody to hIGF-1) for the wild-type and 3mut precursor containing Eb. FIG. 1C shows the Western blot results (using antibody to hIGF-1) for the wild-type and 3mut precursor containing Ec.

FIG. 2A shows the activity of IGF-1-Ea3mut. FIG. 2B shows the activity of IGF-1-Eb3mut. FIG. 2C shows the activity of IGF-1-Eab3mut, which is a 3mut construct in which Ea amino acids 93 to 102 were inserted between amino acids 95 and 96 of Eb. FIG. 2D shows the activity of IGF-1-Ec3mut.

FIGS. 3A and 3B test the receptor selectivity of IGF-1-Ea3mut against the IGF-1 receptor (FIG. 3A) and the insulin receptor (FIG. 3B). FIGS. 3C and 3D tests the receptor selectivity of IGF-1-Eb3mut against the IGF-1 receptor (FIG. 3C) and the insulin receptor (FIG. 3D). FIGS. 4A and 4B test the receptor selectivity of IGF-1-Ec3mut against the IGF-1 receptor (FIG. 4A) and the insulin receptor (FIG. 4B). FIGS. 4C and 4D tests the receptor selectivity of IGF-1-Eab3mut against the IGF-1 receptor (FIG. 4C) and the insulin receptor (FIG. 4D). "IGF1-R3" refers to the Long-R3-IGF-1 described above. The polypeptide listed as "IGF1Eab" refers to construct in which Ea amino acids 93 to 102 were inserted between amino acids 95 and 96 of Eb.

FIG. 6A shows an IGF-1-Eb precursor polypeptide with four sets of modifications: deletion of G1, P2, and E3; mutation of R37 to A; deletion of R71 and S72; and deletion of the last seven C-terminal amino acids. In addition, the polypeptide is lengthened by the addition of two more Eb peptides (but without R71 and S72 and without the last seven C-terminal amino acids) and the addition of a final Eb peptide (buth without R71 and S72) at the C-terminus of the polypeptide. This construct is often referred to as the IGF-1-Eb multimer. FIG. 6B shows an IGF-1-Eab precursor polypeptide with four sets of modifications: deletion of G1, P2, and E3; mutation of R37 to A; deletion of R71 and S72; and insertion of Ea amino acids 93 to 102 between amino acids 95 and 96 of Eb.

FIG. 7A is a sequence alignment of the human IGF-1 (SEQ ID NO:1) with corresponding animal IGF-1. All animal species analyzed and their corresponding GenBank accession numbers for the sequence are given. G1, P2, E3 is conserved in all analyzed species except Sterlet (where S2 replaces P2). R36 and R37 are conserved in all analyzed species.

FIG. 8A is a sequence alignment of the human Ea peptide (SEQ ID NO:2) with various animal Ea peptides. All animal species analyzed and their corresponding GenBank accession numbers for the sequence are given. R71 and S72 are conserved in all analyzed species.

FIG. 9A is a sequence alignment of the human Eb peptide (SEQ ID NO:3) with various animal Eb peptides. All animal species analyzed and their corresponding GenBank accession numbers for the sequence are given. R71 and S72 are conserved in all analyzed species.

FIG. 10A is a sequence alignment of the human Ec peptide (SEQ ID NO:4) with various animal Ec peptides. All animal species analyzed and their corresponding GenBank accession numbers for the sequence are given. R71 and S72 are conserved in all analyzed species.

FIG. 11A is a sequence alignment of the human IGF-2 (SEQ ID NO:7) with corresponding animal IGF-2. All animal species analyzed and their corresponding GenBank accession numbers for the sequence are given. R68 is conserved in all analyzed species; D69 is conserved except for chimpanzee, where a histidine resides in that position.

FIG. 12A is a sequence alignment of the human IGF-2 E-peptide (SEQ ID NO:6) with various animal IGF-2 E-peptides. All animal species analyzed and their corresponding GenBank accession numbers for the sequence are given. R68 is conserved in all analyzed species; D69 is conserved except for Chimpanzee, where a histidine resides in that position.

DETAILED DESCRIPTION OF THE INVENTION

Figure 1A:
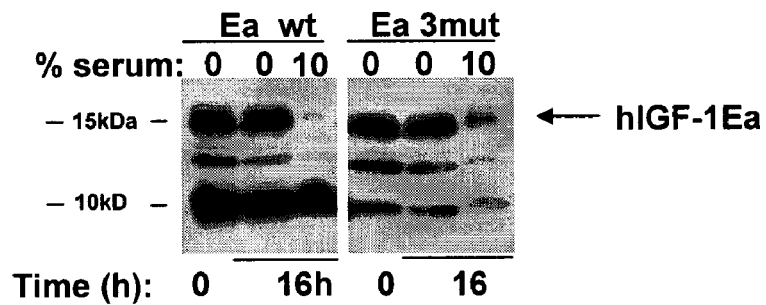
FIGS. 1A-1C are Western blots of polypeptides of the invention and wild-type IGF-1 precursor after zero or 16-hour incubation in the presence or absence of 10% human serum at 37° C. Expression vectors encoding various IGF-1 constructs were transfected into Cos 7 cells, and the conditioned culture medium obtained. The "3mut" refers to a hIGF-1-E-peptide precursor having the following three sets of modifications: deletion of G1, P2, and E3; mutation of Arg 37 to Ala (R37A); and deletion of R71 and S72.

The invention relates to new IGF-1 and IGF-2 precursor polypeptides containing substantially an E-peptide that has been modified to prevent, reduce, or avoid the typical protease cleavage responsible for releasing the active IGF-1 or IGF-2 from its E-peptides. The utility of the polypeptides of the invention is based on the surprising discovery that such precursor polypeptides are biologically active, stable and beneficial as pharmaceuticals.

Screening for Active IGF Precursor Polypeptides

The usefulness of any polypeptide of the invention can be assessed using the following assays.

Stability A polypeptide of the invention should have sufficient stability in the presence of endogenous proteases, such as in human serum, to be an effective drug. To assess stability, an expression vector encoding the polypeptide can be transfected into Cos 7 cells (ATCC) in a DMEM medium containing 10% fetal bovine serum, 100 U/ml penicillin, and 100 µg/ml streptomycin. The culture medium containing secreted polypeptides can be applied to further analysis, or in the alternative, the expression vector can encode readily available tags, such as a hexa-histidine tag, in the polypeptide to facilitate efficient purification of the expressed polypeptides in the Cos 7 cultures. However prepared, the polypeptide sample is incubated in normal human serum (Sigma) or in PBS for various times (e.g., 0, 1, 5, 10, and 16 hours), subjected to polyacrylamide gel electrophoresis, blotted onto nitrocellulose, and the relevant proteins visualized using a primary antibody against human IGF-1 or IGF-2 and a secondary antibody, e.g., conjugated to horseradish peroxidase. Any number of similar blotting and detection techniques, some using fluorescent dyes or even radionuclides, can be used. The intensity of the precursor band versus the intensity of the IGF-1 or IGF-2 band should indicate the degree to which the precursor polypeptide is cleaved under various conditions. A polypeptide of the invention that is exposed to human serum for 16 hours at 37° C. can exhibit a ratio of uncleaved precursor to cleaved mature IGF of about 1:2 to 1:0.1, e.g., about 1:1 to 1:0.5, particularly a ratio of about 1:1 or a ratio of about 1:0.5. Typically, the precursor should exhibit a ratio of at least 1:1.

AKT Phosphorylation A polypeptide of the invention should maintain the ability to signal through the IGF-1 receptor. (Both IGF-1 and IGF-2 signal through the IGF-1 receptor.) To determine this signaling ability, one can assess whether a downstream intracellular target, AKT, is phosphorylated in response to ligand binding at the cell surface. For analysis of AKT phosphorylation, C2C12 myoblasts are starved in serum-free medium and then stimulated with different ligands. Cells are lysed and cleared by centrifugation. AKT phosphorylation and total AKT levels are analyzed by ELISA using PathScan phospho AKT (Ser473) sandwich ELISA kit and PathScan AKT sandwich ELISA kit (Cell Signaling), respectively.

IGF-1 Receptor Specificity A polypeptide of the invention preferably maintains the specificity for the IGF-1 receptor and should bind to the related insulin receptor with low affinity. To assess receptor specificity, polypeptide samples are added to serum-starved NIH3T3 cells overexpressing the IGF-1 receptor or the insulin receptor, and the level of IGF-1 receptor phosphorylation or insulin receptor phosphorylation is determined by lysing the cells and subjecting the lysates to ELISA using the DuoSet IC human phosphor-IGF-1 receptor and insulin receptor ELISA kit (R&D Systems).

In Vivo Testing in Mouse Models of Hypertrophy To determine whether a polypeptide of the invention can act to increase skeletal muscle mass under a context that already leads to muscle hypertrophy, one can subject treated and untreated animals to exercise and determine whether animals receiving the polypeptide have developed larger muscles than untreated animals.

Exercise Models

One model known in the art is based on the use of a voluntary running wheel with user-variable loads (see, e.g., Konhilas et al., Am J Physiol Heart Circ Physiol 289:H455-H465, 2005). The voluntary cage wheel eliminates physical and psychological insults that are common in forced exercised models, and are therefore more appropriate for evaluating candidate drugs that are used in relatively healthy individuals for whom increases in muscle mass is desirable.

Any suitable mouse strain can be used. For example, male C57B1/6J mice can be randomly assigned to experimental (e.g., receiving IGF precursor polypeptide) and control groups. Animals are individually housed in a cage containing an exercise wheel; sedentary control animals are housed in identical cages without a wheel. The exercise wheels are described in Allen et al., J Appl Physiol 90:1900-1908, 2001. Briefly, the system consists of an 11.5 cm-diameter wheel with a 5.0 cm-wide running surface (model 6208, Petsmart, Phoenix, Ariz.) equipped with a digital magnetic counter (model BC 600, Sigma Sport, Olney, Ill.) that is activated by wheel rotation. In addition, each wheel is engineered with a resistance mechanism allowing adjustment of the load. This is accomplished by attaching stainless steel fishing line to the cage top and wrapping the wire around an immovable pulley that is secured to the cage wheel at the axis of rotation so as to not contribute to the wheel load. The wire is again secured to the cage top with a spring and screw. This design permits fine adjustments of the wheel load, which is evenly distributed throughout the rotation of the wheel. Daily exercise values for time and distance run are recorded for each exercised animal throughout the duration of the exercise period. All animals are given water and standard hard rodent chow ad libitum. Voluntary running (cage wheel exposure) can begin at an average age of about 12 weeks for all groups. Each group continues running under varying resistance, depending on experimental group, for 50 days until the animals are about 19 weeks of age. The load on the wheel is determined by hanging known weights on the wheel until the wheel was slightly displaced. All exercise groups begin with no load on the cage wheel for the first week. However, the "no-load" condition is actually 2 g, which is determined as the load necessary to maintain wheel inertia and frictional load. Considering a wheel acclimatization period of 1 week, wheel loads can be changed at one-week intervals, except for higher loads, which can be changed after 2 weeks. The range of loads can be anywhere from 2 g to up to 12 g. Exercised and sedentary control animals are euthanized by cervical dislocation under inhaled anesthesia immediately after the end of the specific exercise period. Body mass is measured, and specific muscles are rapidly excised, washed, and frozen for histological or biochemical assays at a future date.

Alternative exercise hypertrophy models are also available to the skilled artisan. See, e.g., the treadmill exercise model described in Lerman et al., J Appl Physiol 92:2245-2255, 2002.

Clenbuterol Injection Model

Clenbuterol is a $\beta_2$-adrenergic agonist with growth-promoting properties that cause a documented increase in muscle mass. The precise mechanism of clenbuterol action remains unclear, although a reduction in muscle protein degradation has been proposed. In the clinic, clenbuterol is used as an anti-asthma drug, but it appears to be mostly misused as a body-building agent to increase muscle mass in both humans and show animals.

Five mice are given a daily injection of clenbuterol (3 mg/kg, subcutaneous (s.c.)) for 3, 7, or 14 days to induce muscle hypertrophy. Mice injected with PBS serves as negative control. The animals are monitored daily (visual inspection) for any adverse reactions (i.e. unkempt coat, lethargic) to the treatment. Clenbuterol treatment has the potential to make mice more fearful or aggressive, so mice should be especially monitored for fighting if housed in groups. Mice are mobile, and can eat and drink normally. Mice are monitored daily until they are euthanized on day 3, 7, or 14, and tissue collected for further analysis.

In Vivo Testing in Muscle Atrophy Models In various skeletal muscle atrophy models, an IGF precursor polypeptide of the invention can be tested for the ability to maintain muscle mass under conditions that generally reduce muscle mass. With the example models described below, the skilled artisan can readily design and implement controlled experiments involving the administration and use of IGF precursor polypeptides to determine whether such polypeptides can increase muscle mass.

For example, C57B16/2 male mice are purchased from The Jackson Laboratories. Mice are purchased so that they are about 9 weeks at the start of each experiment. Generally mice are housed in microisolator cages with normal rodent chow. At the start of each experiment mice are weighed. At the end of each experiment, generally mice are euthanized by $CO_2$ inhalation followed by cervical dislocation, and muscle tissues harvested for further processing. Mice are weighed to provide "end body weight." Skeletal muscles that can be harvested are tibialis anterior, extensor digitorum longus, soleus, and gastrocnemius muscles. Other tissues harvested occasionally are: heart, liver, spleen, kidneys, testes, and brain. All muscles and tissues are completely dissected and weighed on a balance capable of measuring to 0.0001 g. Tissues are then snap-frozen in liquid nitrogen for later RNA and protein extraction, or snap-frozen embedded in OCT on a cork disc. Muscles frozen on a cork disc for later cryosectioning are immersed in isopentane cooled to a thick slush by liquid nitrogen. All samples are stored at −80° C.

Dexamethasone Treatment

A pharmacological method of inducing muscle wasting in mice is daily intraperitoneal injection with dexamethasone at 20 mg/kg. Dexamethasone is a synthetic member of the glucocorticoid class of hormones. It acts as an anti-inflammatory and immunosuppressant, with a potency of about 40 times that of hydrocortisone. Dexamethasone is used to treat many inflammatory and autoimmune conditions, e.g. rheumatoid arthritis. It is also given to cancer patients undergoing chemotherapy, to counteract certain side-effects of their antitumor treatment. Dexamethasone causes muscle atrophy both in mice and in human patients.

Mice are injected intraperitoneally (ip) with dexamethasone for 3, 7, or 14 days. On the terminal day subjects are euthanized using $CO_2$, and the leg muscles harvested. The animals are monitored daily (visual inspection) for any adverse reactions (i.e. unkempt coat, lethargic) to the treatment. Mice are usually mobile, and can eat and drink normally. Mice injected with PBS are the negative control.

Cast Immobilization

Physical disuse of various muscle groups results in atrophy of those muscles. Ankle joint fixation ("pinned heel" or casting) has proven to be a highly useful and reproducible way to induce physical immobilization of rat and mouse hindlimb musculature.

Mice are anesthetized with isofluorane for immobilization. The ankle and knee joints are fixed at 90 degrees with a light-weight casting material (VET-LITE) around the joints. The material is soaked in warm water and then wrapped around the limb, leaving the toes and hip joint free. The joints are maintained in at 90° positions until the casting material has dried. The contralateral leg serves as control. The mice are then allowed to recover from anesthesia and housed in normal micro isolator cages. Casting has not been observed to cause excessive stress, and animals freely move about the cage to feed and drink. The mice are however monitored daily for any adverse events affecting body weight, activity, and irritations.

Once a cast is applied to a mouse, the animal is monitored daily to make sure that the cast remains in place, as chewing can occur. The animals can move, drink, and feed after recovery of anesthesia, and they do not require special bedding, caging or other assistance.

Denervation

Generally, mice are anesthetized with isofluorane gas for denervation. Using aseptic surgical procedures (three washes of betadine with a final ethanol wash), the right sciatic nerve is isolated in the mid-thigh and a 2 to 5 mm piece cut out. The contralateral leg serves as control.

More specifically, the skin incision is closed with a suture clip, and the animals injected with a single dose of buprenorphine before being allowed to recover from the anesthesia. Three, seven, or 14 days after surgery animals are euthanized by $CO_2$ inhalation followed by cervical dislocation, and muscles (gastrocnemius complex, tibialis anterior, extensor digitorum longus, soleus) are removed for histological and biochemical analyses.

Given that the sciatic nerve is transected, the effected limb is rendered immobile to induce skeletal muscle atrophy of the muscles involved. The animal can otherwise move, drink, and feed after recovery of anesthesia and they do not require special bedding, caging or other assistance. Nonetheless, animals are monitored immediately post-surgery and through recovery (1-2 hrs). In addition, the incision sites and general animal health are monitored for 3 days post-surgery. The suture clip is removed 7 to 10 days after surgery.

Genetic Models

Genetically manipulated transgenic mice can also be used as models of muscle atrophy. For example, the so-called Mini Mice (The Jackson Laboratory, Stock No. 003258) contains a knock out mutation in the IGF-1 gene that results in abnormally decreased postnatal growth, as well as low body weight and size. For additional information, see Powell-Braxton et al., Genes Dev 7:2609-2617, 1993. In addition, the so-called Midi Mice (The Jackson Laboratory, Stock No. 003259) contains a different mutation in the IGF-1 gene that results in a hypomorph exhibiting low adult body weight and other cardiovascular phenotypes. For additional information, see Lembo et al., J Clin Invest 98:2648-2655, 1996.

Critical and Optional Mutations or Modifications in the IGF Precursors

Critical Mutations The invention is based in part on the observation that an IGF precursor polypeptide that contains substantially its E-peptide remains bioactive and stable in the presence of serum. To ensure that the E-peptide is not cleaved by endogenous proteases targeting the dibasic protease site, in general either of the two N-terminal dibasic amino acids of the E-peptide in the precursor is deleted, mutated, or otherwise masked. In the case of hIGF-1, these two amino acids are R71 and S72, while in the case of hIGF-2, these first two amino acids are R68 and D69.

A variety of modifications enables this prevention of cleavage:
(1) Deletion of one or both dibasic residues
(2) Mutate one or both dibasic residues to a non-basic amino acid, such as alanine
(3) Insert one or more non-basic amino acids between the dibasic residues
(4) Place a glycosylation site near the dibasic residues sufficient to mask the protease site
(5) Site-directed pegylation using replacement of either dibasic residue, or insertion near or between the dibasic residues, with a non-natural amino acid, as described below.

In addition, residues K68 and K65 appear to play a role in IGF-1/E-peptide cleavage; accordingly, mutations or deletions of these residues can be incorporated into any tactic directed to the dibasic amino acids as described above.

Mutations at the N-terminus of Mature IGF In certain embodiments of the invention, the IGF precursor polypeptides have deletions or mutations of the first few N-terminal amino acids. In the case of IGF-1, any of the first three N-terminal amino acids can be deleted or mutated, whereas in the case of IGF-2, any of the first six N-terminal amino acids can be deleted or mutated. It has been observed that certain N-terminal amino acids are naturally cleaved in vivo, and the introduction of these mutations or deletions minimizes the in vivo associations of the polypeptides of the invention with IGF binding proteins (IGFBPs). The interaction of IGF-1 and IGF-2 with the IGF-1 receptor is regulated by IGFBPs. All six IGFBPs have been shown to inhibit IGF action (particularly IGFBP5), but in some instances a stimulatory effect has been observed. At least 99% of the IGF in the circulation is normally bound to IGFBPs. The most abundant IGFBP in the circulation after the neonatal period is IGFBP3 which can bind both IGF-1 and IGF-2 with similar affinities. The naturally occurring truncated IGF-1 (bearing deletion of G1, P2, and E3) binds to IGFBP3 with several times lower affinity than natural IGF-1. In addition, G3 is important for IGFBP binding, and G6 plays a similar role in the IGF-2 peptide.

Accordingly, in the case of the hIGF-1 precursor, any of G1, P2, or E3 can be deleted or mutated either alone or in combination. When a mutation is desired, a mutation to alanine can be introduced. In another example, in the case of hIGF-2 precursor, any of P4, S5, and E6 can be deleted or mutated either alone or in combination. When a mutation is desired, a mutation to alanine can be introduced.

Mutations at Residues 36 and 37 IGF-1 can e cleaved by serine proteases present in human serum. Mutation of either R36 or R37 to A can prevent cleavage of IGF-1 at this predicted cleavage site between R36 and R37. In the case of hIGF-2, R38 can be mutated or deleted to prevent this deleterious cleavage.

Use of Glycosylation The in vivo half-life of the polypeptides of the invention can be improved by the addition of N-linked glycosylation sites into either the IGF or the E-peptide portions of the precursor when expressed in mammalian or other eukaryotic cells capable of N-linked glycosylation. It has been shown in vitro that human IGF-1 Ea is glycosylated at N92 and N100, as these portions of Ea fits the consensus N-linked glycosylation sequence of N-X-S/T, where X can be any amino acid and the third amino acid of the triplet is either S or T. It is also know that the adjacent amino acid context of the consensus will affect how strongly the asparagine is glycosylated. Therefore, one strategy to introduce a glycosylation site into Eb or Ec is to insert Ea amino acids around the consensus sequence into roughly the same part of Eb or Ec. A particular implementation of this strategy is illustrated in the Examples below. In any event, any other consensus N-linked glycosylation site, including surrounding context amino acids, known to the skilled artisan can be inserted into a precursor polypeptide of the invention. In addition, O-linked glycosylation of a polypeptide of the invention can be accomplished by choosing the particular host used for production of the polypeptide. For example, use of certain yeast strains for IGF-1 expression results in the addition of oligosaccharides on a serines or threonines. See, e.g., U.S. Pat. No. 5,273,966.

Addition of Poly(ethylene glycol) Conjugation to poly (ethylene glycol) (PEG; pegylation) have proven to be beneficial in prolonging the half-life of therapeutic proteins drugs. It is expected that pegylation of the IGF precursor polypeptides of the invention may result in similar pharmaceutical advantages. Methods of pegylation of IGF-1 are well known in the art. See, for example, US Patent Application Publication 2006/0154865, which describes the beneficial properties of lysine-monopegylated IGF-1. Such lysine-monopegylation can be adapted for the precursor IGF polypeptides of the invention. In addition, pegylation can be achieved in any part of a polypeptide of the invention by the introduction of a normatural amino acid. Certain normatural amino acids can be introduced by the technology described in Deiters et al., J Am Chem Soc 125:11782-11783, 2003; Wang and Schultz, Science 301:964-967, 2003; Wang et al., Science 292:498-500, 2001; Zhang et al., Science 303:371-373, 2004 or in U.S. Pat. No. 7,083,970. Briefly, some of these expression systems involve site-directed mutagenesis to introduce a nonsense codon, such as an amber TAG, into the open reading frame encoding a polypeptide of the invention. Such expression vectors are then introduced into a host that can utilize a tRNA specific for the introduced nonsense codon and charged with the normatural amino acid of choice. Particular normatural amino acids that are beneficial for purpose of conjugating moieties to the polypeptides of the invention include those with acetylene and azido side chains. The IGF precursor polypeptides containing these novel amino acids can then be pegylated at these chosen sites in the protein. In addition, such pegylated IGF molecules without the E-peptide are also useful as therapeutics.

Multimers of E-Peptides In certain pharmacological contexts, it is beneficial to increase the size of a peptide or protein drug to ensure that the drug remains on one side of the blood-brain barrier or the other. Since mature IGF molecules are relatively short peptides, even if the E-peptide remains attached, it can be beneficial to increase the size of the polypeptides of the invention. One means of doing so is to provide multimers of E-peptides at the C-terminus of the IGF precursor polypeptide, as illustrated in certain Examples described below.

C-Terminal Deletion of E-Peptides It is suspected that the free cysteine at position 81 of Eb may result in homodimerization or other effects that, when present in the polypeptides of the invention, might lead to lower activity drugs. Thus, deletion or mutation of C81 in Eb can optimize drug activity. In a particular example, deletion of the last seven amino acids of Eb (i.e., amino acids 81-87) is beneficial.

Other Mutations or Modifications Additional mutations or modifications of IGF that can be incorporated into the IGF precursor polypeptides of the invention are described in U.S. Pat. No. 5,077,276; and US Patent Application Publication Nos. 2005/0287151, 2006/0211606, and 2006/0166328.

The invention should be construed, in addition to human IGF-1 and IGF-2, to include all known and unknown non-human animal precursor IGF-1 or IGF-2 sequences containing substantially its E-peptide wherein the normal cleavage of the E-peptide is avoided or reduced according to modifications of the present invention.

The preferred type of IGF to be used depends upon the species of the subject being treated.

It is preferred that the IGF is species-matched, for example, when a cow is being treated, the preferred type of IGF is bovine IGF.

Although all forms of IGF are likely to have an effect in different subjects due to the high sequence homologies, species matching will avoid potential adverse immunological complications stemming from the induction of an immune response to an IGF from a different species.

In one embodiment of the invention, modified non-human animal precursor IGF-1 sequences are provided.

Preferred are precursor IGF-1 sequences containing substantially its E-peptide wherein the normal cleavage of the E-peptide is avoided or reduced according to modifications of the present invention from a vertebrate animal.

For example, such sequences include but are not limited to sequences from a mouse, rat, cow, pig, horse, sheep, goat, bird, dog, cat, fish and the like, from any source whether natural, synthetic, or recombinant.

In another embodiment of the invention, modified non-human animal precursor IGF-2 sequences are provided.

Preferred are precursor IGF-2 sequences containing substantially its E-peptide wherein the normal cleavage of the E-peptide is avoided or reduced according to modifications of the present invention from a vertebrate animal.

For example, such sequences include but are not limited to sequences from a mouse, rat, cow, pig, horse, sheep, goat, bird, dog, cat, fish and the like from any source, whether natural, synthetic, or recombinant.

Therapeutic Use of IGF Precursor Polypeptides

Indications The invention also includes the use of an IGF precursor polypeptide of the invention in the manufacture of a medicament for the treatment or prevention of a musculoskeletal disease. In addition, the invention includes use of IGF precursor polypeptides to increase muscle or bone mass in an individual, whether or not such an individual is at risk for or has a musculoskeletal disease.

In particular, the musculoskeletal disease can be muscle atrophy. There are many causes of muscle atrophy, including as a result of treatment with a glucocorticoid such as cortisol, dexamethasone, betamethasone, prednisone, methylprednisolone, or prednisolone. The muscle atrophy can also be a result of denervation due to nerve trauma or a result of degenerative, metabolic, or inflammatory neuropathy (e.g., Guillian-Barré syndrome, peripheral neuropathy, or exposure to environmental toxins or drugs). In addition, the muscle atrophy can be a result of an adult motor neuron disease, infantile spinal muscular atrophy, juvenile spinal muscular atrophy, autoimmune motor neuropathy with multifocal conductor block, paralysis due to stroke or spinal cord injury, skeletal immobilization due to trauma, prolonged bed rest, voluntary inactivity, involuntary inactivity, metabolic stress or nutritional insufficiency, cancer, AIDS, fasting, rhabdomyolysis, a thyroid gland disorder, diabetes, benign congenital hypotonia, central core disease, nemalene myopathy, myotubular (centronuclear) myopathy, burn injury, chronic obstructive pulmonary disease, liver disease, sepsis, renal failure, congestive heart failure, or ageing.

The musculoskeletal disease can also be a muscular dystrophy syndrome, such as Duchenne, Becker, myotonic, fascioscapulohumeral, Emery-Deifuss, oculopharyngeal, scapulohumeral, limb girdle, a congenital muscular dystrophy, or hereditary distal myopathy. The musculoskeletal disease can also be osteoporosis, a bone fracture, short stature, or dwarfism.

IGF-1 is suggested as a treatment for insulin-insensitive diabetes, since IGF-1 can also bind heterodimers of IGF-1 receptor and insulin receptor. Accordingly, the polypeptides of the invention can be used to treat diabetes.

IGF-1 is neurotrophic and increases survival of neurons. It has been suggested that IGF-1 can be used to treat instances of motor-neuron death such as seen in amyotrophic lateral sclerosis (ALS), brain atrophy, ageing, and dementia. Accordingly, the polypeptides of the invention can be used to treat conditions associated with neuronal death, such as ALS, brain atrophy, or dementia.

IGF-1 increases both white and red blood cell populations and has an additive effect to administration of erythropoietin. Accordingly, the polypeptides of the invention can be used to treat anemia.

Since IGF-1 and IGF-2 are ubiquitous and essential regulators of cell division and vertebrate growth, they may be advantageously used in a variety of veterinary methods to exogenously enhance or maintain growth in an animal. Some examples include, but are not limited to:

(i) enhancing rate and/or extent of growth in an animal, for example, enhancing muscle growth in swine, cattle, poultry and fish;
(ii) enhancing the efficiency of their conversion of feed into body tissue (lean to fat ratio), for example, in swine, cattle, sheep, poultry and fish; and
(iii) enhancing milk production in lactating animals, for example, dairy cattle, sheep, goats.

Other veterinary therapeutic applications include, but are not limited to:

(iv) treating animal wasting symptoms associated with cachexia, trauma or other consumption diseases, for example, in companion animals such as dogs, cats, and horses; and (v) treating lactating animals for improvement in neonatal health, for example, lactating sows for improvement in neonatal performance.

Methods of Administration The polypeptides of the invention can be delivered in a variety of ways, including the use of gene delivery vehicles. Methods known in the art for the therapeutic delivery of agents such as proteins or nucleic acids can be used for the therapeutic delivery of a polypeptide of the invention, e.g., cellular transfection, gene therapy, direct administration with a delivery vehicle, or pharmaceutically acceptable carrier, indirect delivery by providing recombinant cells containing a nucleic acid encoding the polypeptide.

Various delivery systems are known and can be used to administer the polypeptide of the invention, e.g., encapsulation in liposomes, microparticles, microcapsules, recombinant cells capable of expressing the protein, receptor-mediated endocytosis (see, e.g., Wu and Wu, J Biol Chem 262: 4429-4432, 1987), construction of a nucleic acid as part of a retroviral, adeno-associated viral, adenoviral, poxyiral (e.g., avipoxyiral, particularly fowlpoxyiral) or other vector, etc. Methods of introduction can be enteral or parenteral and include but are not limited to intradermal, intramuscular, intraperitoneal, intravenous, subcutaneous, pulmonary, intranasal, intraocular, epidural, and oral routes. The polypeptides can be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

In another embodiment, the active agent can be delivered in a vesicle, in particular a liposome (see Langer, Science 249: 1527-1533, 1990). In yet another embodiment, the active agent can be delivered in a controlled release system. In one embodiment, a pump may be used. In another embodiment, polymeric materials can be used (see Howard et al., J Neurosurg 71:105, 1989). In another embodiment where the active agent of the invention is a nucleic acid encoding a polypeptide of the invention, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., Proc. Natl. Acad. Sci. USA 88:1864-1868, 1991), etc. Alternatively, a nucleic acid can be introduced intracellularly and incorporated within host cell DNA for expression, by homologous recombination.

Cellular Transfection and Gene Therapy The present invention encompasses the use of nucleic acids encoding polypeptides of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell. The compositions are administered (e.g., by injection into a muscle) to a subject in an amount sufficient to elicit a therapeutic response.

In another aspect, the invention provides a method of treating a target site, i.e., a target cell or tissue, in a human or other animal including transfecting a cell with a nucleic acid encoding a polypeptide of the invention, wherein the nucleic acid includes an inducible promoter operably linked to the nucleic acid encoding the targeting fusion polypeptide. For gene therapy procedures in the treatment or prevention of human disease, see for example, Van Brunt Biotechnology 6:1149-1154, 1998.

Combination Therapies In numerous embodiments, the polypeptides of the present invention can be administered in combination with one or more additional compounds or therapies. For example, multiple polypeptides can be co-administered in conjunction with one or more therapeutic compounds. The combination therapy may encompass simultaneous or alternating administration. In addition, the combination may encompass acute or chronic administration. The polypeptides of the invention can be administered in combination with anabolic agents such as testosterone or specific androgen receptor modulators (SARMs). Additional anabolic agents include growth hormone (GH) or molecules that induce GH release. Ghrelin is particularly useful in a combination therapy for cachexia, since Ghrelin can cause an increase in appetite. In a similar vein, the polypeptides of the invention can be combined with protein supplements to increase anabolism, or combined with physical therapy or exercise to increase body weight. Any molecule that inhibits myostatin is also a candidate for combination therapy.

Pharmaceutical Compositions The present invention also provides pharmaceutical compositions comprising a IGF precursor protein of the invention and a pharmaceutically acceptable carrier. The term "pharmaceutically acceptable" means approved by a regulatory agency of the Federal or a state government or listed in the U.S. Pharmacopeia or other generally recognized pharmacopeia for use in animals or humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In some embodiments, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The polypeptides of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of a polypeptide of the invention which will be effective in the treatment of a condition or disease can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20-5000 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems. In particular, a possible dosage regimen can be about 60 to 120 µg/kg body weight, subcutaneous injection, twice daily.

Veterinary Uses

In addition to the aforementioned methods of administration in humans, there may be additional considerations for veterinary administration.

The dosage may differ when administered to a healthy animal versus those animals suffering from a disease. An assessment of the appropriate dosage can easily be made by those skilled in the art using assays known in the art, for example, the myoblast proliferation assay (Example 79) or the mammary epithelial tissue assay (Example 80) as described below. General assays to measure IGF are also known in the art, such as those in Example 81.

Those skilled in the art will recognize that some species of animal exhibit seasonal fertility influenced by the length of the photoperiod. Any embodiment of a veterinary method or use may optionally include starting the treatment method at a specific time within the animal's reproductive cycle in order to achieve the desired effect. Those skilled in the art will know that reproductive status and cycle can easily be determined, and, if desired, synchronized by the use of an appropriate regimen.

When used for veterinary indications, in addition to methods previously mentioned for human use, the IGF-1 or IGF-2 peptide of the present invention can also be used as an oral drench, or a supplement to oral or solid feeds for animals.

The invention is further described but not limited by the following Examples.

EXAMPLES

Example 1

A DNA expression vector encoding the hIGF-1-Ea precursor polypeptide containing the following modifications was constructed: deletion of G1, deletion of P2, and deletion of E3; mutation of R37 to A; and deletion of R71 and deletion of S72. These mutations are sometimes referred to as "3mut" throughout the present disclosure. This results in the following secreted protein sequence:

(SEQ ID NO: 8)
tlcgaelvdalqfvcgdrgfyfnkptgygsssraapqtgivdeccfr scdlrrlemycaplkpaksavraqrhtdmpktqkevhlknasrgsag nknyrm Cos 7 cells (available from ATCC) were maintained in DMEM containing 10% fetal bovine serum, 100 U/ml penicillin, and 100 µg/ml streptomycin and plated at a density of $1 \times 10^6$ cells per 10-cm plate. These cell cultures were transfected with 8 µg of expression plasmid using Fugene (Roche) according to manufacturer's instructions. Twenty-four hours post-transfection, cells were washed once and cultured in serum-free medium for 48 hours. Supernatants were collected and stored at −80° C.

In order to assess polypeptide stability in human serum, supernatants collected from the Cos 7 cells transfected with wild-type (wt) hIGF-1Ea, and hIGF-1Ea3mut were incubated for 16 hours at 37° C. either in the absence or presence of 10% human serum (Sigma). Samples were separated by 18% SDS-PAGE, and immunoblotting was performed using goat polyclonal antibody to human IGF-1. The results in FIG. 1A indicate that, while the wt hIGF-1Ea was substantially degraded after incubation with serum for 16 hours, the hIGF-1Ea3mut was stabilized. Densitometry indicated that the ratio of uncleaved to cleaved IGF-1 was about 1:6.2, while the ratio for hIGF-1Ea3mut was about 1:0.68, showing that these mutations result in a stabilized polypeptide.

Figure 2A:
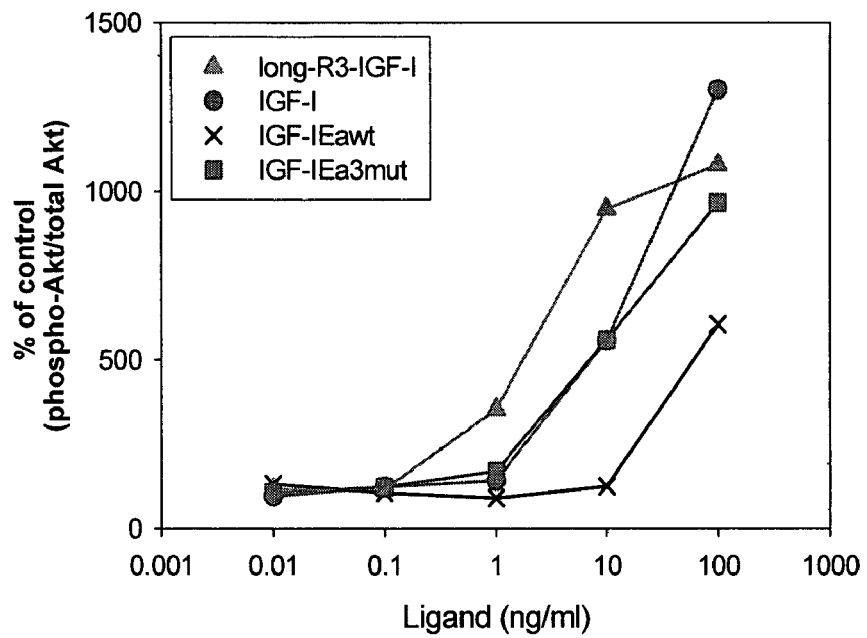
FIGS. 2A-2D are line graphs showing the biological activity of various IGF-1 polypeptides ("ligands"). Biological activity was measured by stimulation of C2C12 myoblasts with Cos 7-expressed polypeptides. The stimulated C2C12 cells were then assayed for the relative amounts of total AKT and phosphorylated AKT. Long-R3-IGF-1 is a commercially available reagent (Sigma Product No. 1-1271) that consists of the mature human IGF-1 amino acid sequence, with an E3R mutation and an additional 13 amino acid N-terminal extension peptide.

To confirm that the hIGF-1Ea3mut was able to signal through the IGF-1R, AKT phosphorylation of cells in contact with the polypeptide was measured. C2C12 were purchased from ATCC and maintained in Dulbecco's modified Eagle's medium (DMEM) with high glucose (Invitrogen) containing 10% fetal bovine serum (AMIMED), 100 U/ml penicillin (Invitrogen), 100 µg/ml streptomycin (Invitrogen) and 2 mM glutamine (Invitrogen). For analysis of AKT phosphorylation, the C2C12 cells were plated at a density of $0.15 \times 10^6$ cells per well of a 6-well plate and were cultured in growth medium for 72 hours. Cells were starved for four hours in serum-free medium and then stimulated with different ligands at 37° C. for 30 minutes. Cells were lysed with PhosphoSafe buffer (Cell Signaling) containing various protease inhibitors and cleared by centrifugation at 14,000×g for 15 minutes at 4° C. AKT phosphorylation and total AKT levels were analyzed by ELISA using PathScan phospho AKT (Ser473) sandwich ELISA kit and PathScan AKT sandwich ELISA kit (Cell Signaling), respectively. The AKT phosphorylation results are summarized in FIG. 2A, which indicate that the hIGF-1Ea3mut was able to activate the IGF-1R cellular pathway to a similar extent as the long-R3-IGF-1 positive control reagent and the recombinant IGF-1. In addition, the data in FIG. 5 directly shows that hIGF-1Ea3mut led to AKT phosphorylation.

Figure 3A:
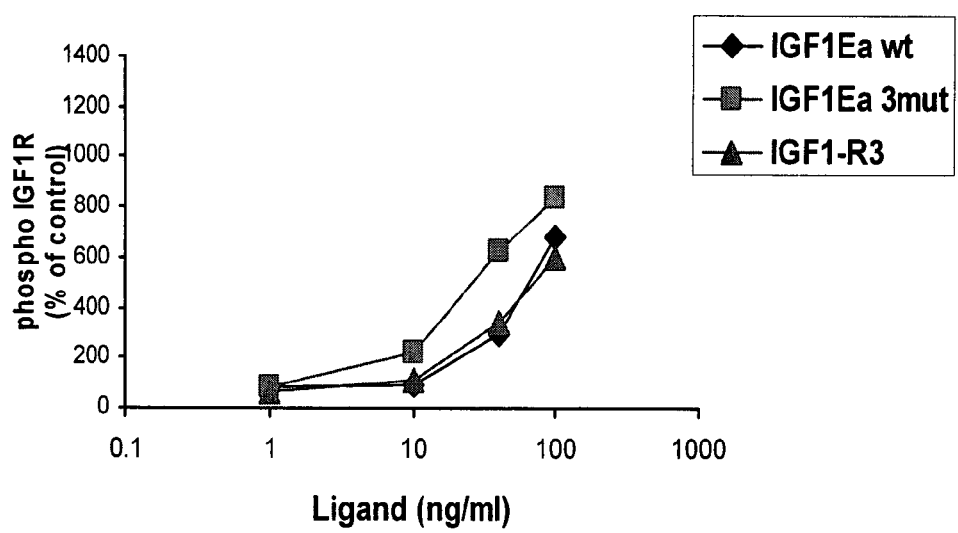
FIGS. 3A-3D and 4A-4D are line graphs showing whether IGF-1 precursor polypeptides of the invention maintain selectivity to the appropriate receptor by assaying for receptor phosphorylation in response to ligand binding.
Figure 3B:
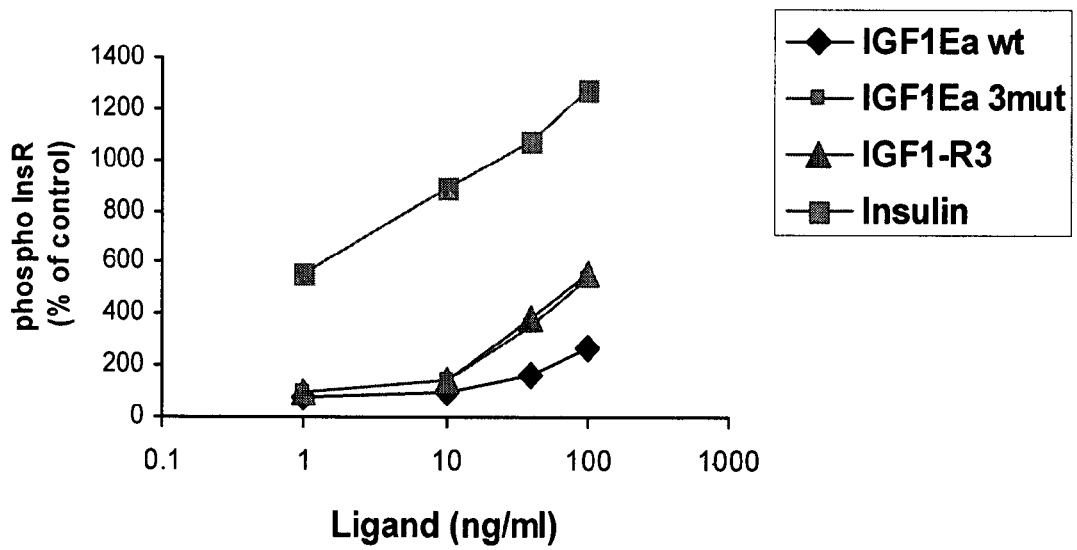

Next, to ensure that the receptor specificity of the hIGF-1Ea3mut remained with the IGF-1R, various ligands were added to cultures of NIH3T3 overexpressing either IGF-1R or insulin receptor (InsR). These cells were cultured under the same conditions as described above for Cos 7 cells. For analysis of IGF-1R and InsR phosphorylation, NIH3T3-IGF1R and NIH3T3-InsR cells were plated at a density of 0.2×10⁶ cells per well of a 6-well plate and were cultured in growth medium for 24 hours. Cells were starved for 18 hours in serum-free medium and then stimulated with different ligands at 37° C. for 10 minutes. Cells were lysed as described above for the AKT experiment, and IGF-1R and InsR phosphorylation levels were analyzed by ELISA using DuoSet IC human phosphor-IGF1R and -InsR ELISA kit (R&D Systems). The results summarized in FIGS. 3A and 3B indicate that this IGF-1 precursor polypeptide retains specificity for the IGF-1 receptor and should bind to the related insulin receptor with low affinity.

Example 2

Figure 1B:
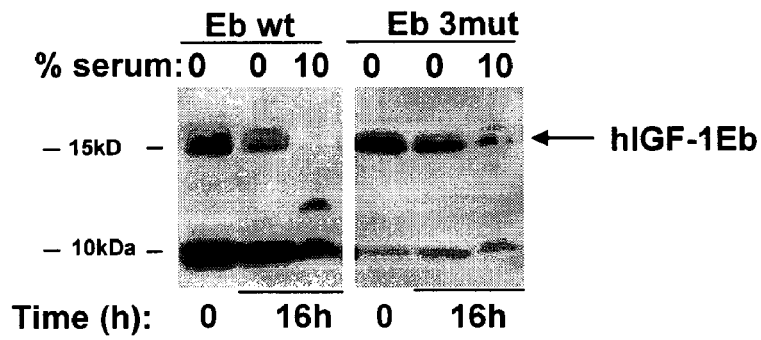
Figure 2B:
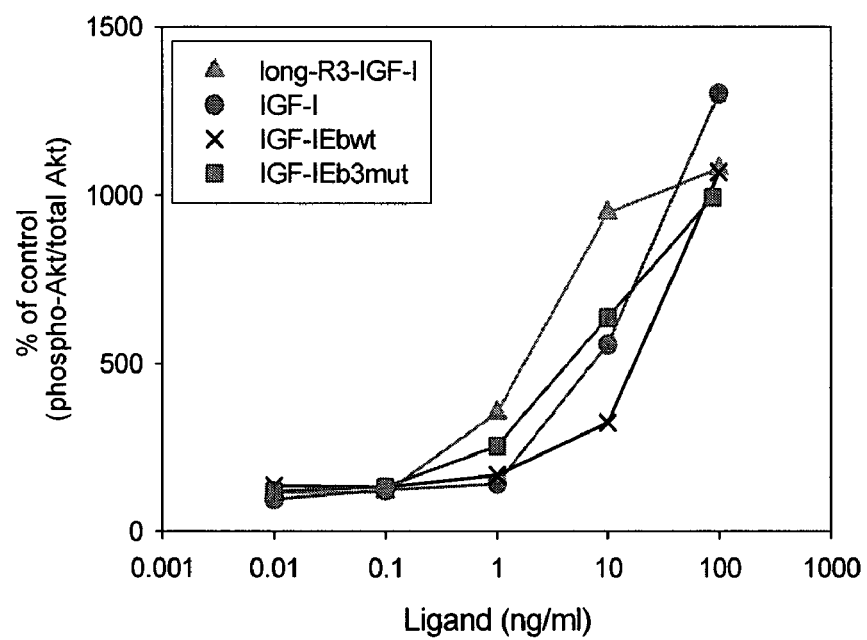
Figure 3C:
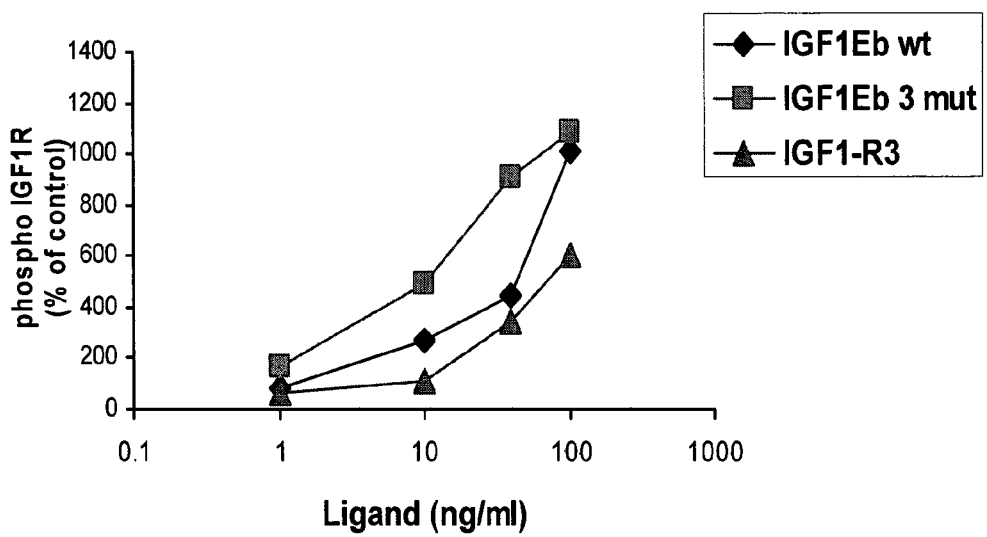
Figure 3D:
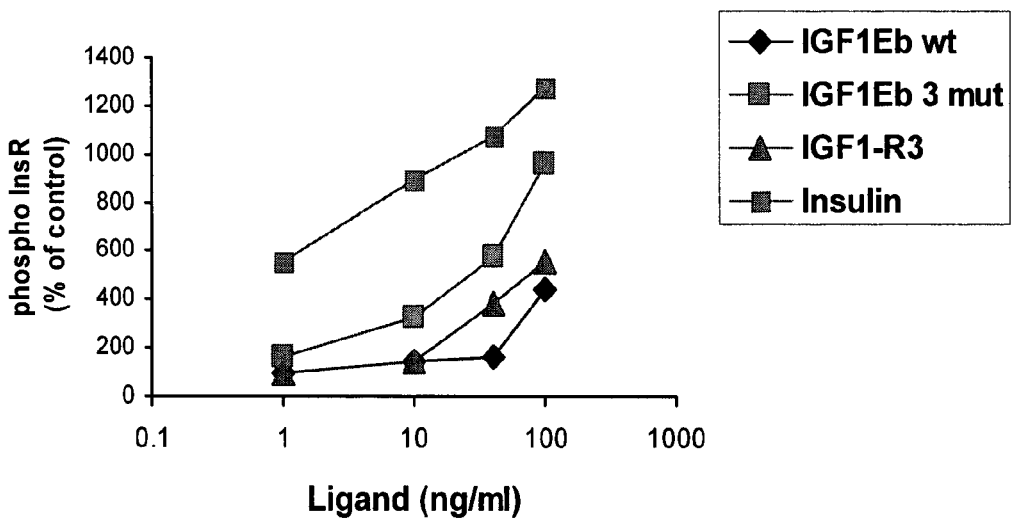

A DNA expression vector encoding the hIGF-1-Eb precursor polypeptide containing the following mutations was constructed: deletion of G1, deletion of P2, and deletion of E3; mutation of R37 to A; and deletion of R71 and deletion of S72 (i.e., the "3mut"). This results in the following secreted protein sequence:

(SEQ ID NO: 9)
tlcgaelvdalqfvcgdrgfyfnkptgygsssarapqtgivdeccfr scdlrrlemycaplkpaksavraqrhtdmpktqkyqppstnkntksq rrkgwpkthpggeqkegteaslqirgkkkeqrreigsrnaecrgkk gk The polypeptide was assayed in accordance with the procedures described in Example 1 above. FIG. 1B and use of densitometry indicated that the ratio of uncleaved to cleaved IGF-1 was about 1:9, while the ratio for hIGF-1Eb3mut was about 1:1, showing that these modifications result in a stabilized polypeptide. FIG. 2B indicates that the hIGF-1Eb3mut was able to activate the IGF-1R cellular pathway to a similar extent as the long-R3-IGF-1 positive control reagent and the recombinant IGF-1. In addition, the data in FIG. 5 directly shows that hIGF-1Eb3mut led to AKT phosphorylation. The results summarized in FIGS. 3C and 3D indicate that this IGF-1 precursor polypeptide retains specificity for the IGF-1 receptor and should bind to the related insulin receptor with low affinity.

Example 3

Figure 1C:
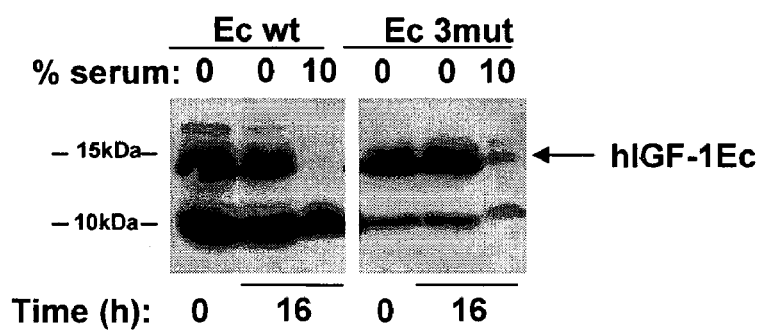
Figure 2C:
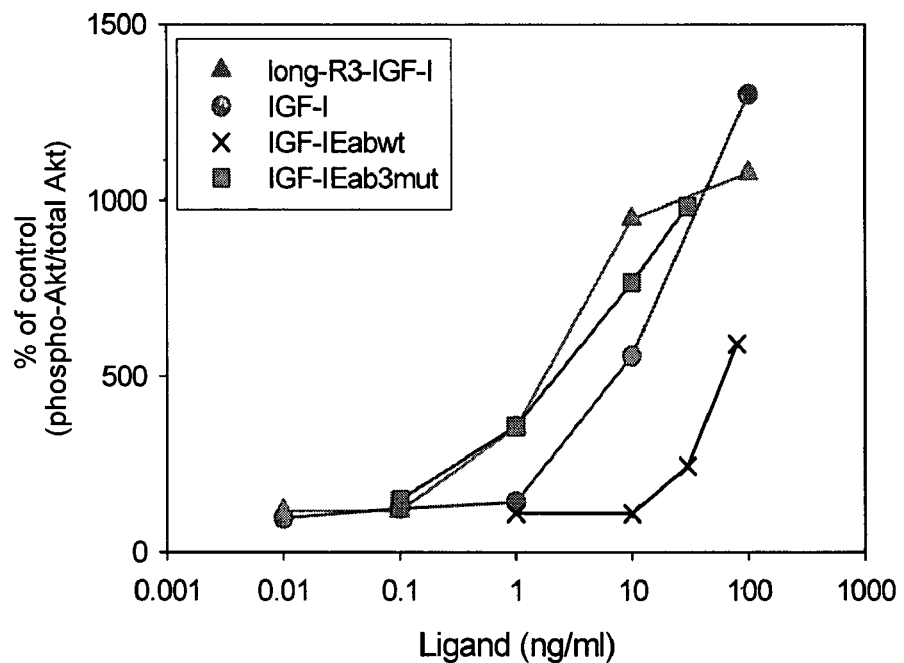
Figure 2D:
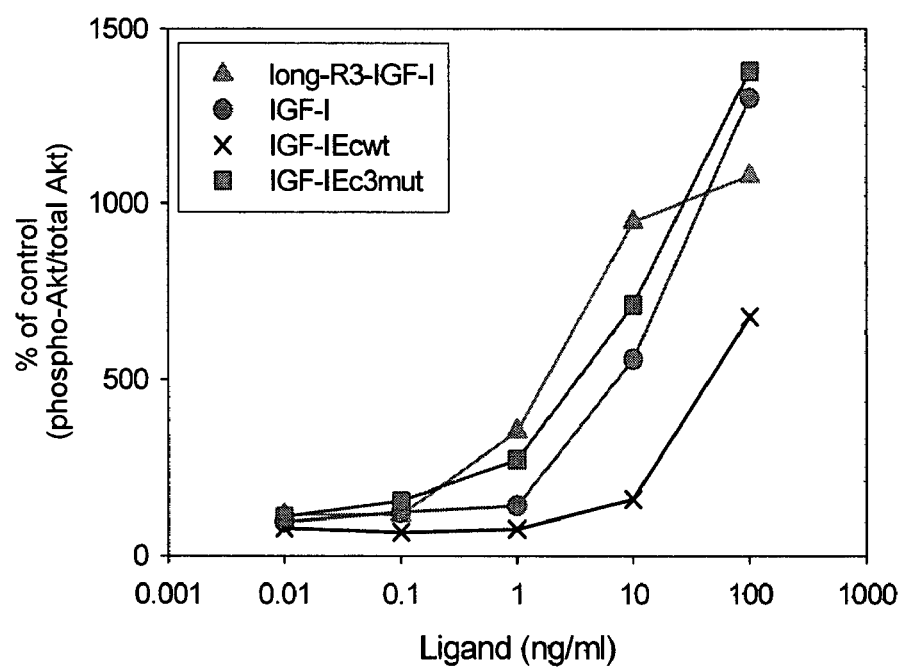
Figure 4A:
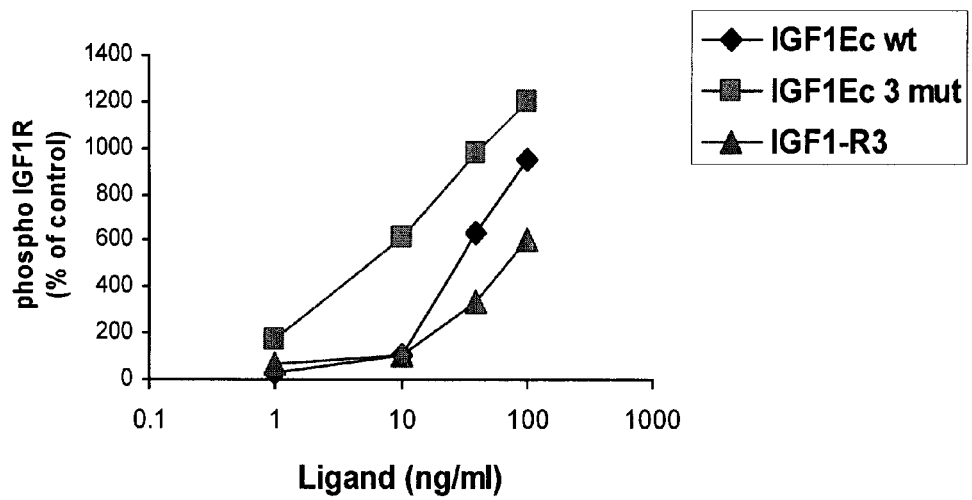
Figure 4B:
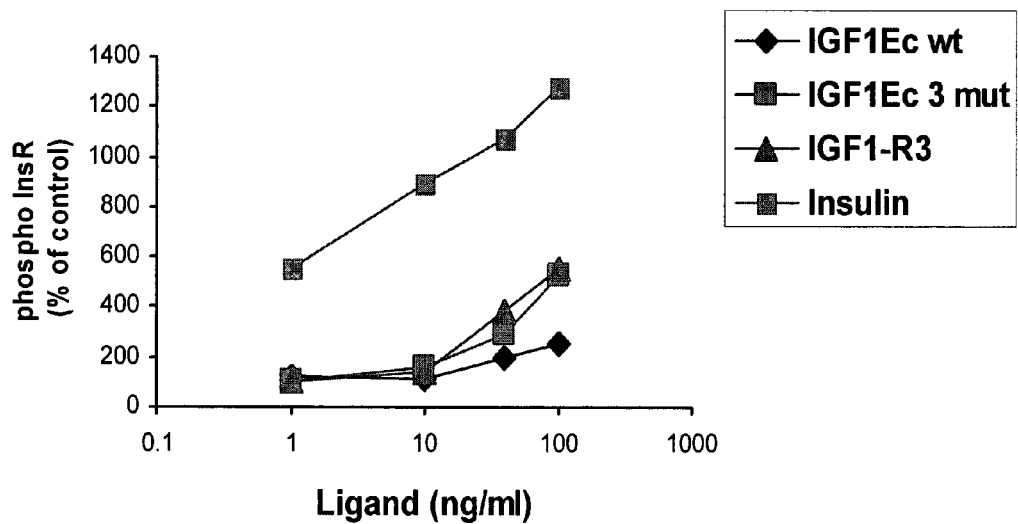

A DNA expression vector encoding the hIGF-1-Ec precursor polypeptide containing the following mutations was constructed: deletion of G1, deletion of P2, and deletion of E3; mutation of R37 to A; and deletion of R71 and deletion of S72 (i.e., the "3mut"). This results in the following secreted protein sequence:

(SEQ ID NO: 10)
tlcgaelvdalqfvcgdrgfyfnkptgygsssrapqtgivdeccfrscdl rrlemycaplkpaksavraqrhtdmpktqkyqppstnkntksqrrkgstf eerk The polypeptide was assayed in accordance with the procedures described in Example 1 above. FIG. 1C and use of densitometry indicated that the ratio of uncleaved to cleaved IGF-1 was about 1:5, while the ratio for hIGF-1Ec3mut was about 1:0.96, showing that these modifications result in a stabilized polypeptide. FIG. 2D indicates that the hIGF-1Ec3mut was able to activate the IGF-1R cellular pathway to a similar extent as the long-R3-IGF-1 positive control reagent and the recombinant IGF-1. In addition, the data in FIG. 5 directly shows that hIGF-1Ec3mut led to AKT phosphorylation. The results summarized in FIGS. 4A and 4B indicate that this IGF-1 precursor polypeptide retains specificity for the IGF-1 receptor and should bind to the related insulin receptor with low affinity.

Example 4

Figure 4C:
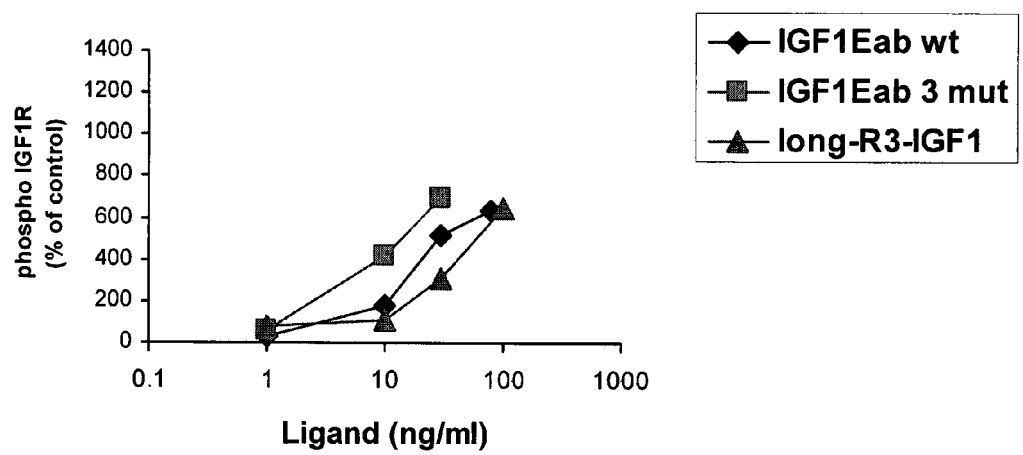
Figure 4D:
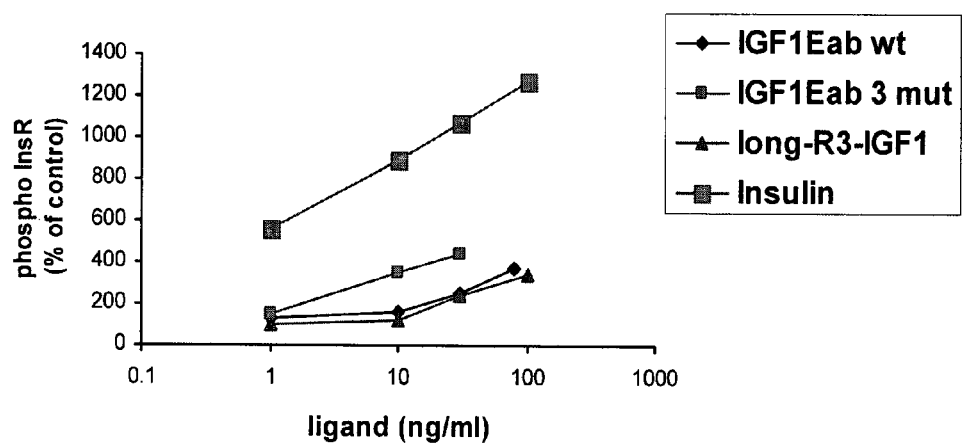

A DNA expression vector encoding the hIGF-1-Eab chimeric precursor polypeptide containing the following modifications to the hIGF-1-Eb peptide was constructed: deletion of G1, deletion of P2, and deletion of E3; mutation of R37 to A; deletion of R71 and deletion of S72 (i.e., the "3mut"); and insertion of Ea amino acids 93 to 102 between amino acids 95 and 96 of Eb. The insertion creates a putative N-linked glycosylation signal at N92. This results in the following secreted protein sequence:

(SEQ ID NO: 11)
tlcgaelvdalqfvcgdrgfyfnkptgygsssraapqtgivdeccfrscd lrrlemycaplkpaksavraqrhtdmpktqkyqppstnknasrgsagnkn tksqrrkgwpkthpggeqkegteaslgirgkkkeqrreigsrnaecrgkk gk The polypeptide was assayed in accordance with some of the procedures described in Example 1 above. FIG. 2C indicates that the hIGF-1Eab3mut was able to activate the IGF-1R cellular pathway to a similar extent as the long-R3-IGF-1 positive control reagent and the recombinant IGF-1. The results summarized in FIGS. 4C and 4D indicate that this IGF-1 precursor polypeptide retains specificity for the IGF-1 receptor and does not activate the insulin receptor.

Example 5

Figure 6A:
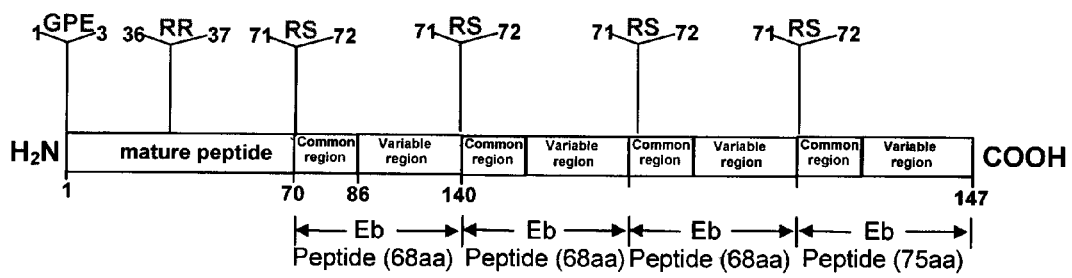
FIGS. 6A and 6B are schematic representations of two of the polypeptides of the invention.

A DNA expression vector encoding the hIGF-1-Eb multimer precursor polypeptide containing the following mutations was constructed: deletion of G1, deletion of P2, deletion of E3, deletion of R36, deletion of R37, deletion of R71, deletion of S72, deletion of the last seven C-terminal amino acids of Eb; and insertion to the C-terminus of this precursor of two additional Eb peptides both without the R71 and S72 and last seven C-terminal amino acids and a fourth and final Eb peptide without the R71 and S72. FIG. 6A shows a schematic drawing of this construct. This results in the following secreted protein sequence:

```
                                    (SEQ ID NO: 12)
tlcgaelvdalqfvcgdrgfyfnkptgygsssapqtgivdeccfrsc dlrrlemycaplkpaksavraqrhtdmpktqkyqppstnkntksqrr kgwpkthpggeqkegteaslqirgkkkeqrreigsrnaersvraqrh tdmpktqkyqppstnkntksqrrkgwpkthpggeqkegteaslqirg kkkeqrreigsrnaersvraqrhtdmpktqkyqppstnkntksqrrk gwpkthpggeqkegteaslqirgkkkeqrreigsrnaersvraqrht dmpktqkyqppstnkntksqrrkgwpkthpggeqkegteaslqirgk kkeqrreigsrnaecrgkkgk
```

Figure 5:
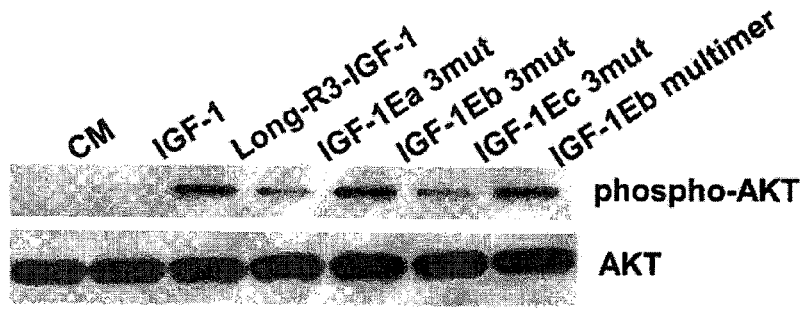
FIG. 5 is a Western blot showing relative AKT phosphorylation upon stimulation of C2C12 myotubes (as a result of 3 to 4 days of differentiation of C2C12 myocytes) by different ligands. The IGF-1Eb multimer refers to the construct schematically shown in FIG. 6A.

This polypeptide was subjected to an AKT phosphorylation assay as described in Example 1. FIG. 5 indicates that this hIGF-1-Eb multimer was able to signal through the IGF-1R pathway.

Example 6

Figure 6B:
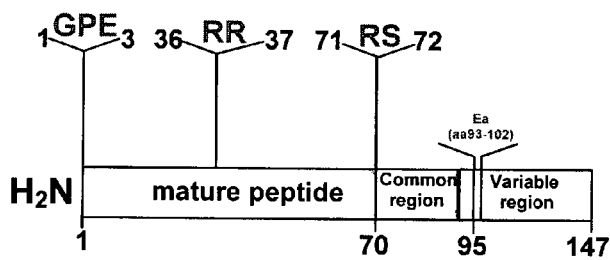
Figure 7B:
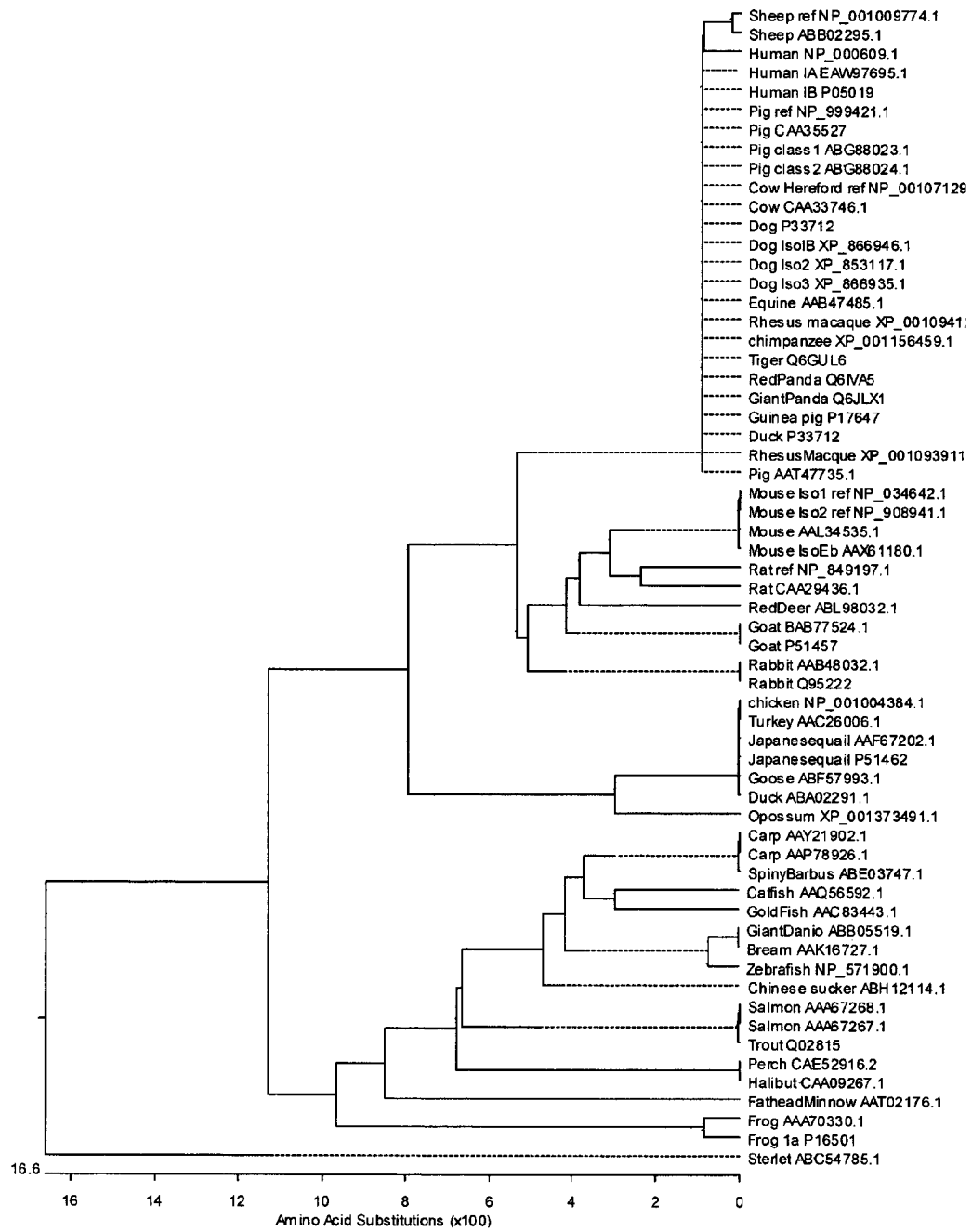
FIG. 7B is a graph showing the phylogeny of the analyzed amino acid sequences compared to human IGF-1 (SEQ ID NO:1). Below the tree is a scale indicating the number of "Amino Acid Substitutions" per 100 residues for protein sequences. The Kimura distance formula is used to calculate distance values, derived from the number of non-gap mismatches and corrected for silent substitutions. The values computed are the mean number of differences per site and fall between zero and 1. Zero represents complete identity and 1 represents no identity. The phylogenetic tree scale uses these values multiplied by 100.
Figure 8B:
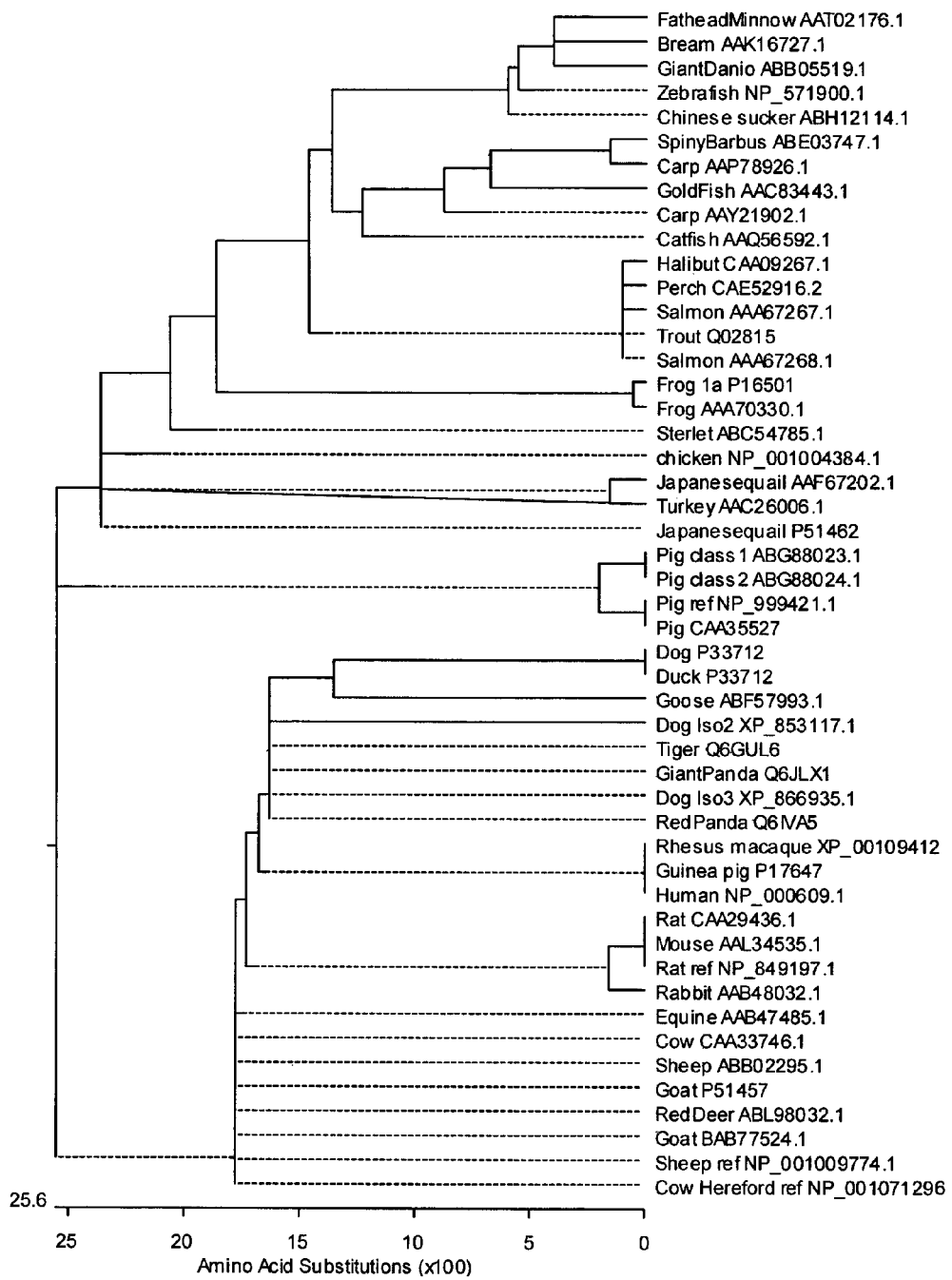
FIG. 8B is a graph showing the phylogeny of the analyzed amino acid sequences compared to human IGF-1 Ea peptide (SEQ ID NO:2).
Figure 9B:
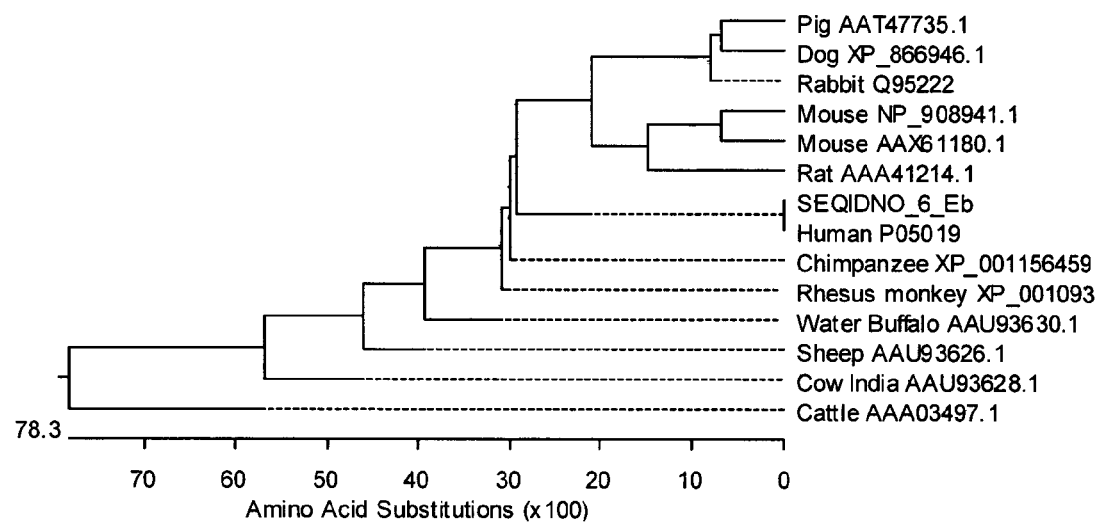
FIG. 9B is a graph showing the phylogeny of the analysed amino acid sequences compared to human IGF-1 Eb peptide (SEQ ID NO:3).
Figure 10B:
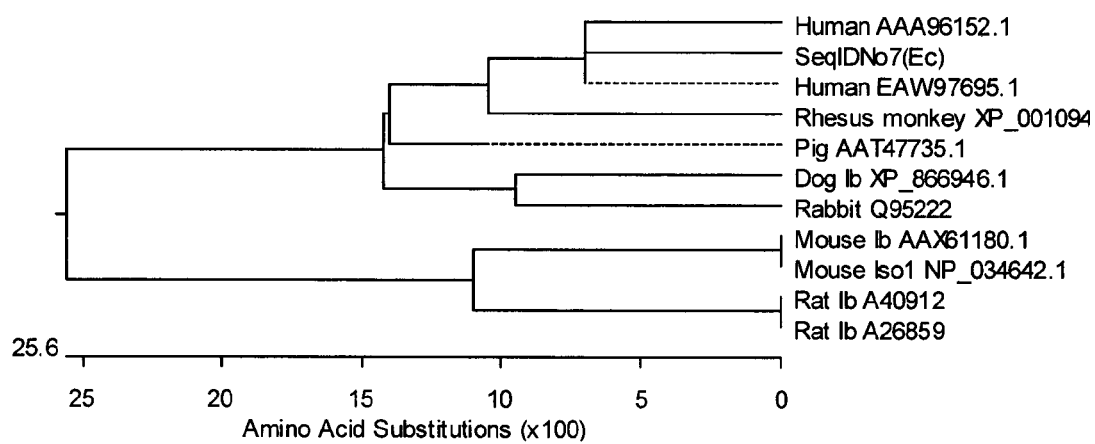
FIG. 10B is a graph showing the phylogeny of the analyzed amino acid sequences compared to human IGF-1 Ec peptide (SEQ ID NO:4).
Figure 11B:
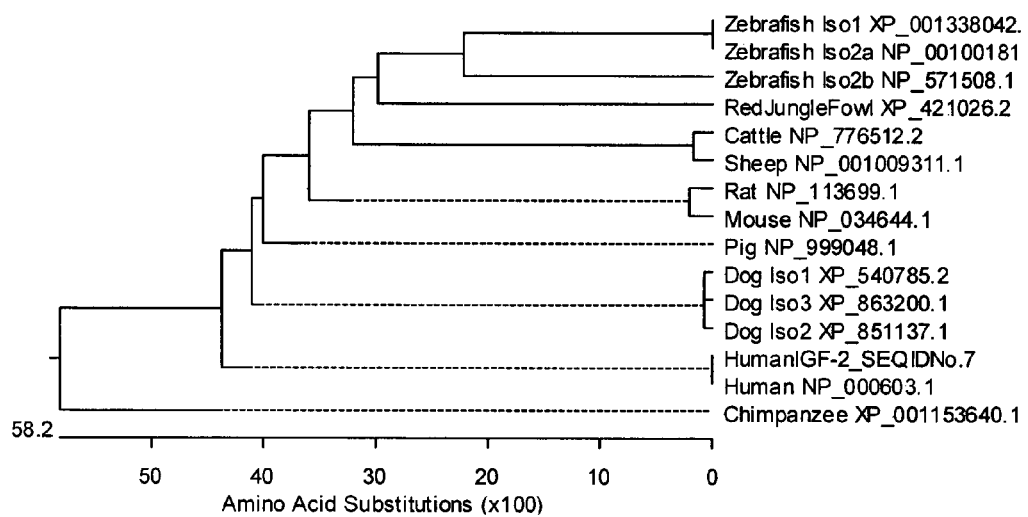
FIG. 11B is a graph showing the phylogeny of the analyzed amino acid sequences compared to human IGF-2 (SEQ ID NO:7).
Figure 12B:
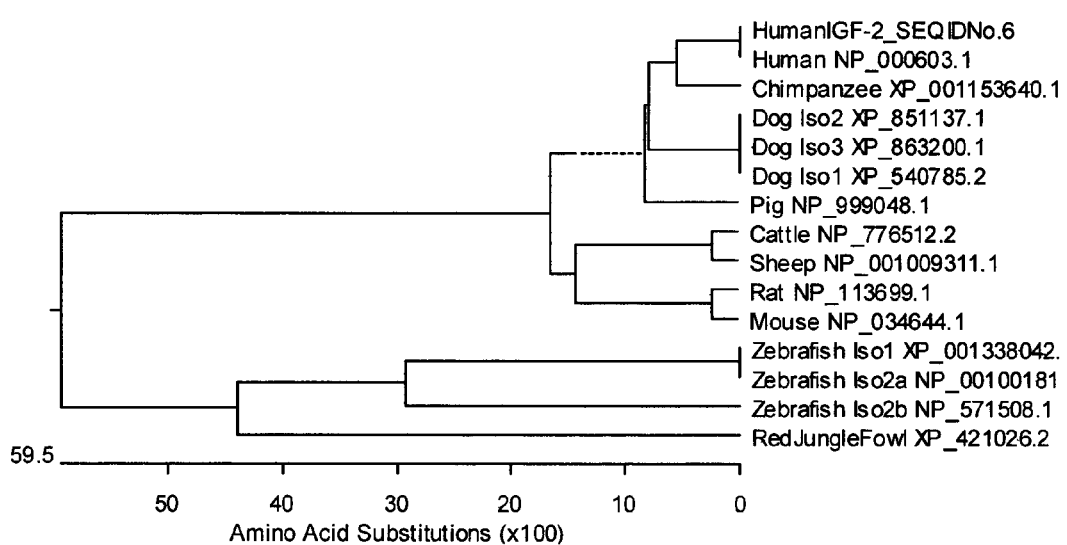
FIG. 12B is a graph showing the phylogeny of the analyzed amino acid sequences compared to human IGF-2 E peptide (SEQ ID NO:6).

A hIGF-1-Eb precursor polypeptide of the invention as shown schematically in FIG. 6B can be expressed. This construct contains the following modifications: deletion of G1, deletion of P2, deletion of E3, deletion of R36, deletion of R37, deletion of R71, deletion of S72; and the insertion of Ea amino acids 93-102 between amino acids 95 and 96 of Eb, thereby creating an N-linked glycosylation site at position N92 and N100. This results in the following secreted protein sequence:

```
                                    (SEQ ID NO: 13)
tlcgaelvdalqfvcgdrgfyfnkptgygsssapqtgivdeccfrscdlr rlemycaplkpaksavraqrhtdmpktqkyqppstnknasrgsagnkntk sqrrkgwpkthpggeqkegteaslqirgkkkeqrreigsrnaecrgkkgk
```

Example 7

A hIGF-2-E precursor polypeptide of the invention having the following modifications can be expressed: deletion of P4, deletion of S5, and deletion of E6; mutation of R38 to A; and deletion of R68 and deletion of D69. This results in the following secreted protein sequence:

```
                                    (SEQ ID NO: 14)
ayrtlcggelvdtlqfvcgdrgfyfsrpasrvsrasrgiveeccfrscdl alletycatpaksevstpptvlpdnfprypvgkffqydtwkqstqrlrrg lpallrarrghvlakeleafreakrhrplialptqdpahggappemasnr k
```

Example 8

A hIGF-1-Ea precursor polypeptide of the invention having the following mutations can be expressed: deletion of G1 and deletion of P2; mutation of E3 to X where X is a nor-matural amino acid that is pegylated; mutation of R37 to A; and deletion of R71 and deletion of S72. This results in the following secreted protein sequence:

```
                                    (SEQ ID NO: 15)
Xtlcgaelvdalqfvcgdrgfyfnkptgygsssraapqtgivdeccfrsc dlrrlemycaplkpaksavraqrhtdmpktqkevhlknasrgsagnknyr m
```

Examples 9-78

Δ=Deletion 9) hIGF-1-Ea: ΔG1, ΔP2, ΔE3; R36A; ΔR71

```
                                    (SEQ ID NO: 16)
tlcgaelvdalqfvcgdrgfyfnkptgygsssarapqtgivdeccfrscd lrrlemycaplkpaksasvraqrhtdmpktqkevhlknasrgsagnknyr m
```

10) hIGF-1-Ea: ΔG1, ΔP2, ΔE3; R36A; ΔS72

```
                                    (SEQ ID NO: 17)
tlcgaelvdalqfvcgdrgfyfnkptgygsssarapqtgivdeccfrscd lrrlemycaplkpaksarvraqrhtdmpktqkevhlknasrgsagnknyr m
```

10) hIGF-1-Ea: ΔG1, ΔP2, ΔE3; R36A; ΔR71, ΔS72

```
                                    (SEQ ID NO: 18)
tlcgaelvdalqfvcgdrgfyfnkptgygsssarapqtgivdeccfrscd lrrlemycaplkpaksavraqrhtdmpktqkevhlknasrgsagnknyrm
```

11) hIGF-1-Ea: ΔG1, ΔP2, ΔE3; R37A; ΔR71

```
                                    (SEQ ID NO: 19)
tlcgaelvdalqfvcgdrgfyfnkptgygsssraapqtgivdeccfrscd lrrlemycaplkpaksasvraqrhtdmpktqkevhlknasrgsagnknyr m
```

12) hIGF-1-Ea: ΔG1, ΔP2, ΔE3; R37A; ΔS72

```
                                    (SEQ ID NO: 20)
tlcgaelvdalqfvcgdrgfyfnkptgygsssraapqtgivdeccfrscd lrrlemycaplkpaksarvraqrhtdmpktqkevhlknasrgsagnknyr m
```

13) hIGF-1-Ea: ΔG1, ΔP2, ΔE3, ΔR37; ΔR71

(SEQ ID NO: 21)
tlcgaelvdalqfvcgdrgfyfnkptgygsssrapqtgivdeccfrscdl
rrlemycaplkpaksasvraqrhtdmpktqkevhlknasrgsagnknyrm 14) hIGF-1-Ea: ΔG1, ΔP2, ΔE3, ΔR37; ΔS72

(SEQ ID NO: 22)
tlcgaelvdalqfvcgdrgfyfnkptgygsssrapqtgivdeccfrscdl
rrlemycaplkpaksarvraqrhtdmpktqkevhlknasrgsagnknyrm 15) hIGF-1-Ea: ΔG1, ΔP2, ΔE3; ΔR37; ΔR71, ΔS72

(SEQ ID NO: 23)
tlcgaelvdalqfvcgdrgfyfnkptgygsssrapqtgivdeccfrscdl
rrlemycaplkpaksavraqrhtdmpktqkevhlknasrgsagnknyrm 16) hIGF-1-Eb: ΔG1, ΔP2, ΔE3; R36A; ΔR71

(SEQ ID NO: 24)
tlcgaelvdalqfvcgdrgfyfnkptgygsssarapqtgivdeccfrscd
lrrlemycaplkpaksasvraqrhtdmpktqkyqppstnkntksqrrkgw
pkthpggeqkegteaslqirgkkkeqrreigsrnaecrgkkgk 17) hIGF-1-Eb: ΔG1, ΔP2, ΔE3; R36A; ΔS72

(SEQ ID NO: 25)
tlcgaelvdalqfvcgdrgfyfnkptgygsssarapqtgivdeccfrscd
lrrlemycaplkpaksarvraqrhtdmpktqkyqppstnkntksqrrkgw
pkthpggeqkegteaslqirgkkkeqrreigsrnaecrgkkgk 18) hIGF-1-Eb: ΔG1, ΔP2, ΔE3; R37A; ΔR71

(SEQ ID NO: 26)
tlcgaelvdalqfvcgdrgfyfnkptgygsssraapqtgivdeccfrscd
lrrlemycaplkpaksasvraqrhtdmpktqkyqppstnkntksqrrkgw
pkthpggeqkegteaslqirgkkkeqrreigsrnaecrgkkgk 19) hIGF-1-Eb: ΔG1, ΔP2, ΔE3; R37A; ΔS72

(SEQ ID NO: 27)
tlcgaelvdalqfvcgdrgfyfnkptgygsssraapqtgivdeccfrscd
lrrlemycaplkpaksarvraqrhtdmpktqkyqppstnkntksqrrkgw
pkthpggeqkegteaslqirgkkkeqrreigsrnaecrgkkgk 20) hIGF-1-Eb: ΔG1, ΔP2, ΔE3; R37A; ΔR71, ΔS72

(SEQ ID NO: 28)
tlcgaelvdalqfvcgdrgfyfnkptgygsssraapqtgivdeccfrscd
lrrlemycaplkpaksavraqrhtdmpktqkyqppstnkntksqrrkgwp
kthpggeqkegteaslqirgkkkeqrreigsrnaecrgkkgk 21) hIGF-1-Eb: ΔG1, ΔP2, ΔE3, ΔR37; ΔR71

(SEQ ID NO: 29)
tlcgaelvdalqfvcgdrgfyfnkptgygsssrapqtgivdeccfrscdl
rrlemycaplkpaksasvraqrhtdmpktqkyqppstnkntkarrkgwpk
thpggeqkegteaslqirgkkkeqrreigsrnaecrgkkgk 22) hIGF-1-Eb: ΔG1, ΔP2, ΔE3, ΔR37; ΔS72

(SEQ ID NO: 30)
tlcgaelvdalqfvcgdrgfyfnkptgygsssrapqtgivdeccfrscdl
rrlemycaplkpaksarvraqrhtdmpktqkyqppstnkntksqrrkgwp
kthpggegkegteaslqirgkkkeqrreigsrnaecrgkkgk 23) hIGF-1-Eb: ΔG1, ΔP2, ΔE3, ΔR37; ΔR71, ΔS72

(SEQ ID NO: 31)
tlcgaelvdalqfvcgdrgfyfnkptgygsssrapqtgivdeccfrscdl
rrlemycaplkpaksavraqrhtdmpktqkyqppstnkntksqrrkgwpk
thpggegkegteaslqirgkkkeqrreigsrnaecrgkkgk 24) hIGF-1-Ec: ΔG1, ΔP2, ΔE3; R36A; ΔR71

(SEQ ID NO: 32)
tlcgaelvdalqfvcgdrgfyfnkptgygsssarapqtgivdeccfrscd
lrrlemycaplkpaksasvraqrhtdmpktqkyqppstnkntksqrrkgs
tfeerk 25) hIGF-1-Ec: ΔG1, ΔP2, ΔE3; R36A; ΔS72

(SEQ ID NO: 33)
tlcgaelvdalqfvcgdrgfyfnkptgygsssarapqtgivdeccfrscd
lrrlemycaplkpaksarvraqrhtdmpktqkyqppstnkntksqrrkgs
tfeerk 26) hIGF-1-Ec: ΔG1, ΔP2, ΔE3; R36A; ΔR71, ΔS72

(SEQ ID NO: 34)
tlcgaelvdalqfvcgdrgfyfnkptgygsssarapqtgivdeccfrscd lrrlemycaplkpaksavracyhtdmpktqkyqppstnkntkscrrkgst feerk 27) hIGF-1-Ec: ΔG1, ΔP2, ΔE2; R37A; ΔR71

(SEQ ID NO: 35)
tlcgaelvdalqfvcgdrgfyfnkptgygsssraapqtgivdeccfrsed lrrlemycaplkpaksasvraqrhtdmpktqkyqppstnkntksqrrkgs tfeerk 28) hIGF-1-Ec: ΔG1, ΔP2, ΔE3; R37A; ΔS72

(SEQ ID NO: 36)
tlcgaelvdalqfvcgdrgfyfnkptgygsssraapqtgivdeccfrscd lrrlemycaplkpaksarvraqrhtdmpktqkyqppstnkntksqrrkgs tfeerk 29) hIGF-1-Ec: ΔG1, ΔP2, ΔE3; R37A; ΔR71, ΔS72

(SEQ ID NO: 37)
tlcgaelvdalqfvcgdrgfyfnkptgygsssraapqtgivdeccfrscd lrrlemycaplkpaksavraqrhtdmpktqkyqppstnkntksqrrkgst feerk 30) hIGF-1-Ec: ΔG1, ΔP2, ΔE3, ΔR37, ΔR71

(SEQ ID NO: 38)
tlcgaelvdalqfvcgdrgfyfnkptgygsssrapqtgivdeccfrscdl rrlemycaplkpaksasvraqrhtdmpktqkyqppstnkntksqrrkgst feerk 31) hIGF-1-Ec: ΔG1, ΔP2, ΔE3, ΔR37, ΔS72

(SEQ ID NO: 39)
tlcgaelvdalqfvcgdrgfyfnkptgygsssrapqtgivdeccfrscdl rrlemycaplkpaksarvraghtdmpktqkyqppstnkntksqrrkgstf eerk 32) hIGF-1-Eab: ΔG1, ΔP2, ΔE3; R36A; ΔR71; insertion of Ea aa 93-102 between aa 95 and 96 of Eb (i.e., "Eab")

(SEQ ID NO: 40)
tlcgaelvdalqfvcgdrgfyfnkptgygsssarapqtgivdeccfrscd lrrlemycaplkpaksasvracrhtdmpktqkyqppstnknasrgsagnk ntkscffkgwpkthpggegkegteaslqirgkkeqrreigsrnaecrgk kgk 33) hIGF-1-Eab: ΔG1, ΔP2, ΔE3; R37A; ΔR71

(SEQ ID NO: 41)
tlcgaelvdalqfvcgdrgfyfnkptgygsssraapqtgivdeccfrscd lrrlemycaplkpaksasvraqrhtdmpktqkyqppstnknasrgsagnk ntksqrrkgwpkthpggeqkegteaslqirgkkeqrreigsrnaecrgk kgk 34) hIGF-1-Eab: ΔG1, ΔP2, ΔE3, ΔR37, ΔR71

(SEQ ID NO: 42)
tlcgaelvdalqfvcgdrgfyfnkptgygsssrapqtgivdeccfrscdl rrlemycaplkpaksasvraghtdmpktqkyqppstnknasrgsagnknt kscinkgwpkthpggegkegteaslqirgkkeqrreigsrnaecrgkkg k 35) hIGF-1-Eab: ΔG1, ΔP2, ΔE3; R36A; ΔS72

(SEQ ID NO: 43)
tlcgaelvdalqfvcgdrgfyfnkptgygsssarapqtgivdeccfrscd lrrlemycaplkpaksarvraqrhtdmpktqkyqppstnknasrgsagnk ntksqffkgwpkthpggeqkegteaslqirgkkeqrreigsrnaecrgk kgk 36) hIGF-1-Eab: ΔG1, ΔP2, ΔE3; R37A; ΔS72

(SEQ ID NO: 44)
tlcgaelvdalqfvcgdrgfyfnkptgygsssraapqtgivdeccfrscd lrrlemycaplkpaksarvraqrhtdmpktqkyqppstnknasrgsagnk ntksqrrkgwpkthpggeqkegteaslqirgkkeqrreigsrnaecrgk kgk 37) hIGF-1-Eab: ΔG1, ΔP2, ΔE3, ΔR37, ΔS72

(SEQ ID NO: 45)
tlcgaelvdalqfvcgdrgfyfnkptgygsssrapqtgivdeccfrscdl
rrlemycaplkpaksarvraqrhtdmpktqkyqppstnknasrgsagnkn
tksqrrkgwpkthpggeqkegteaslqirgkkeqrreigsrnaecrgkk
gk 38) hIGF-1-Eab: ΔG1, ΔP2, ΔE3; R36A; ΔR71, ΔS72

(SEQ ID NO: 46)
tlcgaelvdalqfvegdrgfyfnkptgygsssarapqtgivdeccfrscd
lrrlemycaplkpaksavraqrhtdmpktqkyqppstnknasrgsagnkn
tksqrrkgwpkthpggeqkegteaslqirgkkeqrreigsrnaecrgkk
gk 39) hIGF-1-Eab: ΔG1, ΔP2, ΔE3, ΔR37, ΔR71, ΔS72

(SEQ ID NO: 47)
tlcgaelvdalqvcgdrgfyfnkptgygsssrapqtgivdeccfrsecdl
rrlemycaplkpaksavraqrhtdmpktqkmpstnknasrgsagnkntks
qrrkgwpkthpggeqkegteaslqirgkkeqrreigsrnaecrgkkgk 40) hIGF-1-Ea: ΔP2, ΔE3; R37A; ΔR71, ΔS72

(SEQ ID NO: 48)
gtlcgaelvdalqfvcgdrgfyfnkptgygsssraapqtgivdeccfrsc
dlrrlemycaplkpaksavraqrhtdmpktqkevhlknasrgsagnknyr
m 41) hIGF-1-Eb: ΔP2, ΔE3; R37A; ΔR71, ΔS72

(SEQ ID NO: 49)
gtlcgaelvdalqfvcgdrgfyfnkptgygsssraapqtgivdeccfrsc
dlrrlemycaplkpaksavraqrhtdmpktqkyqppstnkntksqrrkgw
pkthpggeqkegteaslqirgkkeqrreigsrnaecrgkkgk 42) hIGF-1-Eb multimer: (ΔG1, ΔP2, ΔE3; R37A)-3xEb(ΔR71, ΔS72, ΔC-term 7 aa)-Eb(ΔR71, ΔS72)

(SEQ ID NO: 50)
tlcgaelvdalqfvcgdrgfyfnkptgygsssraapqtgivdeccfrscd
lrrlemycaplkpaksavraqrhtdmpktqkyqppstnkntksqrrkgwp
kthpggeqkegteaslqirgkkeqrreigsrnaevraqrhtdmpktqky
qppstnkntksqrrkgwpkthpggeqkegteaslqirgkkeqrreigsr
naevraqrhtdmpktqkyqppstnkntksqrrkgwpkthpggeqkegtea
slqirgkkeqrreigsrnaevraqrhtdmpktqkyqppstnkntkswrk
gwpkthpggeqkegteaslqirgkkeqrreigsrnaecrgkkgk 43) hIGF-1-Eb multimer: (ΔP2, ΔE3; R37A)-3xEb(ΔR71, ΔS72, ΔC-term 7 aa)-Eb(ΔR71, ΔS72)

(SEQ ID NO: 51)
gtlcgaelvdalqfvcgdrgfyfnkptgygsssraapqtgivdeccfrsc
dlrrlemycaplkpaksavraqrhtdmplaqkyqppstnkntksqrrkgw
pkthpggeqkegteaslqirgkkeqrreigsrnaevraqrhtdmpktqk
yqppstnkntksqrrkgwpkthpggeqkegteaslqirgkkeqrreigs
rnaevraqrhtdmpktqkyqppstnkntksqrrkgwpkthpggeqkegte
aslqirgkkeqrreigsrnaevraqrhtdmpktqkyqppstnkntksqr
rkgwpkthpggeqkegteaslqirgkkeqrreigsrnaecrgkkgk 44) hIGF-1-Ec: ΔP2, ΔE3; R37A; ΔR71, ΔS72

(SEQ ID NO: 52)
gtlcgaelvdalqfvcgdrgfyfnkptgygsssraapqtgivdeccfrsc
dlrrlemycaplkpaksavraqrhtdmplaqkyqppstnkntksqrrgs
tfeerk 45) hIGF-1-Ea: ΔE3; R37A; ΔR71, ΔS72

(SEQ ID NO: 53)
gptlcgaelvdalqfvcgdrgfyfnkptgygsssraapqtgivdeccfrs
cdlrrlemycaplkpaksavraqrhtdmpktqkevhlknasrgsagnkny
rm 46) hIGF-1-Eb: ΔE3; R37A; ΔR71, ΔS72

(SEQ ID NO: 54)
gptlcgaelvdalqfvcgdrgfyfnkptgygsssraapqtgivdeccfrs
cdlrrlemycaplkpaksavraqrhtdmpktqkyqppstnkntksqrrkg
wpkthpggeqkegteaslqirgkkeqrreigsrnaecrgkkgk 47) hIGF-1-Eb multimer: (ΔG1, ΔP2, ΔE3; R37A)-3xEb(ΔR71, ΔS72, ΔC-term 7 aa)-Eb(ΔR71, ΔS72)

(SEQ ID NO: 55)
tlcgaelvdalqfvcgdrgfyfnkptgygsssraapqtgivdeccfrscd lrrlemycaplkpaksavraqrhtdmpktqkyqppstnkntksqrrkgwp
kthpggeqkegteaslqirgkkkeqrreigsrnaevraqrhtdmpktqky
qppstnkntksqrrkgwpkthpggeqkegteaslqirgkkkeqrreigsr
naevraqrhtdmpktqkyqppstnkntksqrrkgwpkthpggeqkegtea
slqirgkkkeqrreigsrnaevraqrhtdmpktqkyqppstnkntksqrr
kgwpkthpggeqkegteaslqirgkkkeqrreigsrnaecrgkkgk

48) hIGF-1-Eb multimer: (ΔE3; R37A)-3xEb(ΔR71, ΔS72, ΔC-term 7 aa)-Eb(ΔR71, ΔS72)

(SEQ ID NO: 56)
gptlcgaelvdalqfvcgdrgfyfnkptgygsssraapqtgivdeccfrs
cdlrrlemycaplkpaksavracyhtdmpktqkyqppstnkntksqrrkg
wpkthpggegkegteaslqirgkkkeqrreigsrnaevraqrhtdmpktq
kyqppstnkraksqrrkgwpkthpggeqkegteaslqirgkkkeqrreig
srnaevraqrhtdmpktqkyqppstnkntksqrrkgwpkthpggegkegt
easlqirgkkkeqrreigsrnaevraqrhtdmpktqkyqppstnkntksq
rrkgwpkthpggeqkegteaslqirgkkkeqrreigsrnaecrgkkgk

49) hIGF-1-Ec: ΔE3; R37A; ΔR71, ΔS72

(SEQ ID NO: 57)
gptlcgaelvdalqfvcgdrgfyfnkptgygsssraapqtgivdeccfrs
cdlrrlemycaplkpaksavraqrhtdmpktqkyqppstnkntkscpkgs
tfeerk

50) hIGF-1-Ea: ΔE3; R37A; ΔR71, ΔS72

(SEQ ID NO: 58)
gptlcgaelvdalqfvcgdrgfyfnkptgygsssraapqtgivdeccfrs
cdlrrlemycaplkpaksavraqrhtdmpktqkevhlknasrgsagnkny
rm

51) hIGF-1-Eb: ΔE3; R37A; ΔR71, ΔS72

(SEQ ID NO: 59)
gptlcgaelvdalqfvcgdrgfyfnkptgygsssraapqtgivdeccfrs
cdlrrlemycaplkpaksavraqrhtdmpktqkyqppstnkntksqrrkg
wpkthpggeqkegteaslqirgkkkeqrreigsrnaecrgkkgk

52) hIGF-1-Ec: ΔE3; R37A; ΔR71, ΔS72

(SEQ ID NO: 60)
gptlcgaelvdalqfvcgdrgfyfnkptgygsssraapqtgivdeccfrs
cdlrrlemycaplkpaksavraqrhtdmpktqkyqppstnkntksqrrkg
stfeerk

53) hIGF-1-Eab: ΔE3; R37A; ΔR71, ΔS72

(SEQ ID NO: 61)
gptlcgaelvdalqfvcgdrgfyfnkptgygsssraapqtgivdeccfrs
cdlrrlemycaplkpaksavraqrhtdmpktqkyqppstnknasrgsagn
kntksqrrkgwpkthpggeqkegteaslqirgkkkeqrreigsrnaecrg
kkgk

54) hIGF-1-Eb multimer: (ΔE3; R37A)-3xEb(ΔR71, ΔS72, ΔC-term 7 aa)-Eb(ΔR71, ΔS72)

(SEQ ID NO: 62)
gptlcgaelvdalqfvcgdrgfyfnkptgygsssraapqtgivdeccfrs
cdlrrlemycaplkpaksavraqrhtdmpktqkyqppstnkntksqrrkg
wpkthpggeqkegteaslqirgkkkeqrreigsrnaevraqrhtdmpktq
kyqppstnkntksqrrkgwpkthpggeqkegteaslqirgkkkeqrreig
srnaevraqrhtdmpktqkyqppstnkntksqrrkgwpkthpggegkegt
easlqirgkkkeqrreigsrnaevraqrhtdmpktqkyqppstnkntksq
rrkgwpkthpggeqkegteaslqirgkkkeqrreigsrnaecrgkkgk

55) hIGF-1-Ea: E3A; R37A; ΔR71, ΔS72

(SEQ ID NO: 63)
gpatlcgaelvdalqfvcgdrgfyfnkptgygsssraapqtgivdeccfr
scdlrrlemycaplkpaksavraqrhtdmpktqkevhlknasrgsagnkn
yrm

56) hIGF-1-Eb: E3A; R37A; ΔR71, ΔS72

(SEQ ID NO: 64)
gpatlcgaelvdalqfvcgdrgfyfnkptgygsssraapqtgivdeccfr
scdlrrlemycaplkpaksavraqrhtdmpktqkyqppstnkntksqrrk
gwpkthpggeqkegteaslqirgkkkeqrreigsrnaecrgkkgk

57) hIGF-1-Ec: E3A; R37A; ΔR71, ΔS72

(SEQ ID NO: 65)
gpatlcgaelvdalqfvcgdrgfyfnkptgygsssraapqtgivdeccfr
scdlrrlemycaplkpaksavraqrhtdmpktqkyqppstnkntksqrrk
gstfeerk 58) hIGF-1-Eab: E3A; R37A; ΔR71, ΔS72

(SEQ ID NO: 66)
gpatlcgaelvdalqfvcgdrgfyfnkptgygsssraapqtgivdeccfr
scdlrrlemycaplkpaksavraqrhtdmpktqkyqppstnknasrgsag
nkntksqrrkgwpkthpggegkegteaslqirgkkkeqrreigsrnaecr
gkkgk 59) hIGF-1-Eb multimer: (E3A; R37A)-3xEb(ΔR71, ΔS72, ΔC-term 7 aa)-Eb(ΔR71, ΔS72)

(SEQ ID NO: 67)
gpatlcgaelvdalqfvcgdrgfyfnkptgygsssraapqtgivdeccfr
scdlrrlemycaplkpaksavraqrhtdmpktqkyqppstnknktsqrrk
gwpkthpggeqkegteaslqirgkkkeqrreigsrnaevraqrhtdmpkt
qkyqppstnknktsqrrkgwpkthpggeqkegteaslqirgkkkeqrrei
gsrnaevraqrhtdmpktqkyqppstnknktsqrrkgwpkthpggeqkeg
teaslqirgkkkeqrreigsrnaevraqrhtdmpktqkyqppstnknkts
qrrkgwpkthpggeqkegteaslqirgkkkeqrreigsrnaecrgkkgk 60) hIGF-1-Ea: ΔP2, ΔE3; R37A; ΔR71, ΔS72

(SEQ ID NO: 68)
gtlcgaelvdalqfvcgdrgfyfnkptgygsssraapqtgivdeccfrsc
dlrrlemycaplkpaksavraqrhtdmpktqkevhlknasrgsagnknyr
m 61) hIGF-1-Eb: ΔP2, ΔE3; R37A; ΔR71, ΔS72

(SEQ ID NO: 69)
gtlcgaelvdalqfvcgdrgfyfnkptgygsssraapqtgivdeccfrsc
dlrrlemycaplkpaksavraqrhtdmpktqkyqppstnknktsqrrkgw
pkthpggeqkegteaslqirgkkkeqrreigsrnaecrgkkgk 62) hIGF-1-Ec: ΔP2, ΔE3; R37A; ΔR71, ΔS72

(SEQ ID NO: 181)
gtlcgaelvdalqfvcgdrgfyfnkptgygsssraapqtgivdeccfrsc
dlrrlemycaplkpaksavraqrhtdmpktqkyqppstnknktsqrrkgs
tfeerk 63) hIGF-1-Eab: ΔP2, ΔE3; R37A; ΔR71, ΔS72

(SEQ ID NO: 70)
gtlcgaelvdalqfvcgdrgfyfnkptgygsssraapqtgivdeccfrsc
dlrrlemycaplkpaksavraqrhtdmpktqkyqppstnknasrgsagnk
ntksqrrkgwpkthpggeqkegteaslqirgkkkeqrreigsrnaecrgk
kgk 64) hIGF-1-Eb multimer: (ΔP2, ΔE3; R37A)-3xEb (ΔR71, ΔS72, ΔC-term 7 aa)-Eb(ΔR71, ΔS72)

(SEQ ID NO: 71)
gtlcgaelvdalqfvcgdrgfyfnkptgygsssraapqtgivdeccfrsc
dlrrlemycaplkpaksavraqrhtdmpktqkyqppstnknktsqrrkgw
pkthpggeqkegteaslqirgkkkeqrreigsrnaevraqrhtdmpktqk
yqppstnknktsqrrkgwpkthpggeqkegteaslqirgkkkeqrreigs
rnaevraqrhtdmpktqkyqppstnknktsqrrkgwpkthpggeqkegte
aslqirgkkkeqrreigsrnaevraqrhtdmpktqkyqppstnknktsqr
rkgwpkthpggeqkegteaslqirgkkkeqrreigsrnaecrgkkgk 65) hIGF-1-Eb: ΔG1, ΔP2; E3X; R37A; ΔR71, ΔS72

(SEQ ID NO: 72)
Xtlcgaelvdalqfvcgdrgfyfnkptgygsssraapqtgivdeccfrsc
dlrrlemycaplkpaksavraqrhtdmpktqkyqppstnknktsqrrkgw
pkthpggeqkegteaslqirgkkkeqrreigsrnaecrgkkgk 66) hIGF-1-Ec: ΔG1, ΔP2; E3X; R37A; ΔR71, ΔS72

(SEQ ID NO: 73)
Xtlcgaelvdalqfvcgdrgfyfnkptgygsssraapqtgivdeccf
rscdlrrlemycaplkpaksavraqrhtdmpktqkyqppstnknkts
qrrkgstfeerk 67) hIGF-1-Eab: ΔG1, ΔP2; E3X; R37A; ΔR71, ΔS72

(SEQ ID NO: 74)
Xtlcgaelvdalqfvcgdrgfyfnkptgygsssraapqtgivdeccf
rscdlrrlemycaplkpaksavraqrhtdmpktqkyqppstnknasr
gsagnkntksqrrkgwpkthpggeqkegteaslqirgkkkeqrreig
srnaecrgkkgk 68) hIGF-1-Eb multimer: (ΔG1, ΔP2; E3X; R37A)-3xEb(ΔR71, ΔS72, ΔC-term 7 aa)-Eb(ΔR71, ΔS72)

(SEQ ID NO: 75)
Xtlcgaelvdalqfvcgdrgfyfnkptgygsssraapqtgivdeccf
rscdlrrlemycaplkpaksavraqrhtdmpktqkyqppstnkntks
qrrkgwpkthpggeqkegteaslqirgkkkeqrreigsrnaevraqr
htdmpktqkyqppstnkntksqrrkgwpkthpggeqkegteaslqir
gkkkeqrreigsrnaevraqrhtdmpktqkyqppstnkntksqrrkg
wpkthpggeqkegteaslqirgkkkeqrreigsrnaevraqrhtdmp
ktqkyqppstnkntksqrrkgwpkthpggeqkegteaslqirgkkke
qrreigsrnaecrgkkgk 69) hIGF-1-Ea: ΔG1, ΔP2, ΔE3; R37A; ΔR71; S72X (SEQ ID NO: 76)
tlcgaelvdalqfvcgdrgfyfnkptgygsssraapqtgivdeccfr
scdlrrlemycaplkpaksaXvraqrhtdmpktqkevhlknasrgsa
gnknyrm 70) hIGF-1-Eb: ΔG1, ΔP2, ΔE3; R37A; ΔR71; S72X (SEQ ID NO: 77)
tlcgaelvdalqfvcgdrgfyfnkptgygsssraapqtgivdeccfr
scdlrrlemycaplkpaksaXvraqrhtdmpktqkyqppstnkntks
qrrkgwpkthpggeqkegteaslqirgkkkeqrreigsrnaecrgkk
gk 71) hIGF-1-Ec: ΔG1, ΔP2, ΔE3; R37A; ΔR71; S72X (SEQ ID NO: 78)
tlcgaelvdalqfvcgdrgfyfnkptgygsssraapqtgivdeccfr
scdlrrlemycaplkpaksaXvraqrhtdmpktqkyqppstnkntks
qrrkgstfeerk 72) hIGF-1-Eab: ΔG1, ΔP2, ΔE3; R37A; ΔR71; S72X (SEQ ID NO: 79)
tlcgaelvdalqfvcgdrgfyfnkptgygsssraapqtgivdeccfr
scdlrrlemycaplkpaksaXvraqrhtdmpktqkyqppstnknasr
gsagnkntksqrrkgwpkthpggeqkegteaslqirgkkkeqrreig
srnaecrgkkgk 73) hIGF-1-Eb multimer: (ΔG1, ΔP2, ΔE3; R37A)-Eb(ΔR71; S72X; ΔC-term 7 aa)-2xEb(ΔR71, ΔS72, ΔC-term 7 aa)-Eb(ΔR71, ΔS72)

(SEQ ID NO: 80)
tlcgaelvdalqfvcgdrgfyfnkptgygsssraapqtgivdeccfr
scdlrrlemycaplkpakXsavraqrhtdmpktqkyqppstnkntks
qrrkgwpkthpggeqkegteaslqirgkkkeqrreigsrnaevraqr
htdmpktqkyqppstnkntksqrrkgwpkthpggeqkegteaslqir
gkkkeqrreigsrnaevraqrhtdmpktqkyqppstnkntksqrrkg
wpkthpggeqkegteaslqirgkkkeqrreigsrnaevraqrhtdmp
ktqkyqppstnkntksqrrkgwpkthpggeqkegteaslqirgkkke
qrreigsrnaecrgkkgk 74) hIGF-1-Ea: ΔG1, ΔP2, ΔE3; R37A; ΔR71, ΔS72; N92X (SEQ ID NO: 81)
tlcgaelvdalqfvcgdrgfyfnkptgygsssraapqtgivdeccfr
scdlrrlemycaplkpaksavraqrhtdmpktqkevhlkXasrgsag
nknyrm 75) hIGF-1-Eb: ΔG1, ΔP2, ΔE3; R37A; ΔR71, ΔS72; C142X (SEQ ID NO: 82)
tlcgaelvdalqfvcgdrgfyfnkptgygsssraapqtgivdeccfr
scdlrrlemycaplkpaksavraqrhtdmpktqkyqppstnkntksq
rrkgwpkthpggeqkegteaslqirgkkkeqrreigsrnaeXrgkk
gk 76) hIGF-1-Eab: ΔG1, ΔP2, ΔE3; R37A; ΔR71, ΔS72; C151X (SEQ ID NO: 83)
tlcgaelvdalqfvcgdrgfyfnkptgygsssraapqtgivdeccfr
scdlrrlemycaplkpaksavraqrhtdmpktqkyqppstnknasrg
sagnkntksqrrkgwpkthpggeqkegteaslqirgkkkeqrreigs
rnaeXrgkkgk 78) hIGF-1-Eb multimer (ΔG1, ΔP2, ΔE3; R37A)-3xEb(ΔR71, ΔS72, ΔC-term 7 aa)-Eb(ΔR71, ΔS72; C71X)

(SEQ ID NO: 84)
tlcgaelvdalqfvcgdrgfyfnkptgygsssraapqtgivdeccfr

-continued scdlemycaplkpaksavraqrhtdmpktqkyqppstnkntksqrrk gwpkthpggeqkegteaslqirgkkkeqrreigsrnaevraqrhtdm pktqkyqppstnkntksqrrkgwpkthpggeqkegteaslqirgkkk eqrreigsrnaevraqrhtdmpktqkyqppstnkntksqrrkgwpkt hpggeqkegteaslqirgkkkeqrreigsrnaevraqrhtdmpktqk yqppstnkntksqrrkgwpkthpggeqkegteaslqirgkkkeqrre igsrnaeXrgkkgk Example 79

Myoblast Proliferation Assay

The myoblast proliferation assay provides a reliable in vitro indicator of IGF activity and is used as a model for factors affecting embryonic myoblasts and adult satellite cells. Factors active in this system behave similarly in primary cultures of myoblasts. The enhancement of myoblast proliferation in vitro by a peptide of this invention indicates its activity in causing increased myoblast proliferation and, therefore, an increase in ultimate myofiber number in utero. In addition, similar enhancement of myoblast proliferation indicates that peptides of this invention can be used to enhance adult muscle hypertrophy, e.g. via stimulation of satellite muscle cell proliferation.

Example 80

Mammary Epithelial Tissue Assay

In lactating animals, the amount of mammary epithelial tissue is a limiting factor in milk production, as these are the cells which produce and secrete milk. Employing in vitro systems, epithelial cells obtained from mammary glands of animals can be stimulated by the modified IGF-1 or IGF-2 of the present invention to proliferate and produce increased quantities of milk constituents. It can further be demonstrated that mammary epithelial cells stimulated to proliferate in one such in vitro cell system can be reimplanted in cleared mammary fat pads and be stimulated to proliferate and/or produce milk in lactating female animals.

Example 81

Measurement of IGF-1 or IGF-2 in Blood or Other Body Fluids

The effective amount of the peptide administered parenterally per dose can be measured by a dose-response curve. For example, modified IGF peptides of the invention can be measured in the blood or body fluids of the subject to be treated to determine the dosing. Alternatively, one can administer increasing amounts of the peptide to the subject and check the serum levels of the subject for modified IGF-1 and IGF-2. The amount of peptide to be employed can be calculated on a molar basis based on these serum levels of modified IGF-1 or IGF-2.

One method for determining appropriate dosing of the peptide entails measuring an IGF peptide of the invention in a biological fluid such as a body or blood fluid. Measuring such levels can be done by any means, including RIA and ELISA. After measuring IGF levels, the fluid is contacted with the peptide using single or multiple doses. After this contacting step, the IGF levels are re-measured in the fluid. If the fluid IGF levels have fallen by an amount sufficient to produce the desired efficacy for which the molecule is to be administered, then the dose of the molecule can be adjusted to produce maximal efficacy. This method may be carried out in vitro or in vivo. Preferably, this method is carried out in vivo, i.e., after the fluid is extracted from a subject and the IGF levels measured, the peptide herein is administered to the mammal using single or multiple doses (that is, the contacting step is achieved by administration to an animal), and then the IGF levels are re-measured from fluid extracted from the animal.

Another method for determining dosing is to use antibodies to the peptide or another detection method for the peptide in the LIFA format.

Example 82

In Vivo Pharmacokinetics of hIGF-1-Ec 3mut

Adult male mice (n=3/group) received an intravenous (i.v.) bolus injection of rhIGF-1 at 1 mg/kg, and hIGF-1-Ec 3mut (described in Example 3) at 1.55 mg/kg. Serial blood specimens were collected at 5, 15, 30 and 60 minutes after administration of test material. Serum concentrations of rhIGF-1 and hIGF-1-Ec 3mut were determined by ELISA. This assay is specific for hIGF-1.

Equimolar doses of rhIGF-1 and hIGF-1-Ec 3mut were administered i.v. in mice. The results show significantly higher levels of the hIGF-1-Ec 3mut protein as compared to rhIGF-1 at all examined time points, indicating that the hIGF-1-Ec 3mut is metabolically more stable than the 70 amino acid-long IGF-1.

| time (min) | IGF-1-Ec 3mut (nM) | IGF-1 (nM) |
|---|---|---|
| 5 | 201.4 | 54.7 |
| 15 | 65.3 | 14.3 |
| 30 | 12 | 2.4 |
| 60 | 0.76 | 0.2 |

SEQUENCE LISTING

<160> NUMBER OF SEQ ID NOS: 181

<210> SEQ ID NO 1
<211> LENGTH: 70
<212> TYPE: PRT
<213> ORGANISM: Homo sapiens
<220> FEATURE:
<221> NAME/KEY: PEPTIDE

```
<222> LOCATION: (1)...(70)
<223> OTHER INFORMATION: Human IGF-1 also called Somatomedin

<400> SEQUENCE: 1

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
50                  55                  60

Lys Pro Ala Lys Ser Ala
65                  70

<210> SEQ ID NO 2
<211> LENGTH: 35
<212> TYPE: PRT
<213> ORGANISM: Homo sapiens
<220> FEATURE:
<221> NAME/KEY: PEPTIDE
<222> LOCATION: (1)...(35)
<223> OTHER INFORMATION: IGF-1 mRNA E-peptide (Ea)

<400> SEQUENCE: 2

Arg Ser Val Arg Ala Gln Arg His Thr Asp Met Pro Lys Thr Gln Lys
 1               5                  10                  15

Glu Val His Leu Lys Asn Ala Ser Arg Gly Ser Ala Gly Asn Lys Asn
                20                  25                  30

Tyr Arg Met
        35

<210> SEQ ID NO 3
<211> LENGTH: 77
<212> TYPE: PRT
<213> ORGANISM: Homo sapiens
<220> FEATURE:
<221> NAME/KEY: PEPTIDE
<222> LOCATION: (1)...(77)
<223> OTHER INFORMATION: IGF-1 mRNA E-peptide (Eb)

<400> SEQUENCE: 3

Arg Ser Val Arg Ala Gln Arg His Thr Asp Met Pro Lys Thr Gln Lys
 1               5                  10                  15

Tyr Gln Pro Pro Ser Thr Asn Lys Asn Thr Lys Ser Gln Arg Arg Lys
                20                  25                  30

Gly Trp Pro Lys Thr His Pro Gly Gly Glu Gln Lys Glu Gly Thr Glu
            35                  40                  45

Ala Ser Leu Gln Ile Arg Gly Lys Lys Lys Glu Gln Arg Arg Glu Ile
50                  55                  60

Gly Ser Arg Asn Ala Glu Cys Arg Gly Lys Lys Gly Lys
65                  70                  75

<210> SEQ ID NO 4
<211> LENGTH: 40
<212> TYPE: PRT
<213> ORGANISM: Homo sapiens
<220> FEATURE:
<221> NAME/KEY: PEPTIDE
<222> LOCATION: (1)...(40)
<223> OTHER INFORMATION: IGF-1 mRNA E-peptide (Ec)

<400> SEQUENCE: 4
```

Arg Ser Val Arg Ala Gln Arg His Thr Asp Met Pro Lys Thr Gln Lys
1               5                   10                  15

Tyr Gln Pro Pro Ser Thr Asn Lys Asn Thr Lys Ser Gln Arg Arg Lys
            20                  25                  30

Gly Ser Thr Phe Glu Glu Arg Lys
        35                  40

<210> SEQ ID NO 5
<211> LENGTH: 105
<212> TYPE: PRT
<213> ORGANISM: Homo sapiens
<220> FEATURE:
<221> NAME/KEY: PEPTIDE
<222> LOCATION: (1)...(105)
<223> OTHER INFORMATION: Wild type IGF-1 e-peptide (Ea)

<400> SEQUENCE: 5

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala Gly Asn Lys Asn Tyr Arg Met
            100                 105

<210> SEQ ID NO 6
<211> LENGTH: 89
<212> TYPE: PRT
<213> ORGANISM: Homo sapiens
<220> FEATURE:
<221> NAME/KEY: PEPTIDE
<222> LOCATION: (1)...(89)
<223> OTHER INFORMATION: E-peptide Human IGF-2

<400> SEQUENCE: 6

Arg Asp Val Ser Thr Pro Pro Thr Val Leu Pro Asp Asn Phe Pro Arg
1               5                   10                  15

Tyr Pro Val Gly Lys Phe Phe Gln Tyr Asp Thr Trp Lys Gln Ser Thr
            20                  25                  30

Gln Arg Leu Arg Arg Gly Leu Pro Ala Leu Leu Arg Ala Arg Arg Gly
        35                  40                  45

His Val Leu Ala Lys Glu Leu Glu Ala Phe Arg Glu Ala Lys Arg His
50                  55                  60

Arg Pro Leu Ile Ala Leu Pro Thr Gln Asp Pro Ala His Gly Gly Ala
65                  70                  75                  80

Pro Pro Glu Met Ala Ser Asn Arg Lys
                85

<210> SEQ ID NO 7
<211> LENGTH: 156
<212> TYPE: PRT
<213> ORGANISM: Homo sapiens
<220> FEATURE:
<221> NAME/KEY: PEPTIDE
<222> LOCATION: (1)...(156)

<223> OTHER INFORMATION: IGF-2 precursor to E-peptide in Sequence 6

<400> SEQUENCE: 7

```
Ala Tyr Arg Pro Ser Glu Thr Leu Cys Gly Gly Glu Leu Val Asp Thr
  1               5                  10                  15
Leu Gln Phe Val Cys Gly Asp Arg Gly Phe Tyr Phe Ser Arg Pro Ala
                 20                  25                  30
Ser Arg Val Ser Arg Arg Ser Arg Gly Ile Val Glu Glu Cys Cys Phe
             35                  40                  45
Arg Ser Cys Asp Leu Ala Leu Leu Glu Thr Tyr Cys Ala Thr Pro Ala
 50                  55                  60
Lys Ser Glu Arg Asp Val Ser Thr Pro Pro Thr Val Leu Pro Asp Asn
 65                  70                  75                  80
Phe Pro Arg Tyr Pro Val Gly Lys Phe Phe Gln Tyr Asp Thr Trp Lys
                 85                  90                  95
Gln Ser Thr Gln Arg Leu Arg Arg Gly Leu Pro Ala Leu Leu Arg Ala
                100                 105                 110
Arg Arg Gly His Val Leu Ala Lys Glu Leu Glu Ala Phe Arg Glu Ala
            115                 120                 125
Lys Arg His Arg Pro Leu Ile Ala Leu Pro Thr Gln Asp Pro Ala His
130                 135                 140
Gly Gly Ala Pro Pro Glu Met Ala Ser Asn Arg Lys
145                 150                 155
```

<210> SEQ ID NO 8
<211> LENGTH: 100
<212> TYPE: PRT
<213> ORGANISM: Homo sapiens
<220> FEATURE:
<221> NAME/KEY: PEPTIDE
<222> LOCATION: (1)...(100)
<223> OTHER INFORMATION: 3MUT HIGF-1 Ea

<400> SEQUENCE: 8

```
Thr Leu Cys Gly Ala Glu Leu Val Asp Ala Leu Gln Phe Val Cys Gly
  1               5                  10                  15
Asp Arg Gly Phe Tyr Phe Asn Lys Pro Thr Gly Tyr Gly Ser Ser Ser
                 20                  25                  30
Arg Ala Ala Pro Gln Thr Gly Ile Val Asp Glu Cys Cys Phe Arg Ser
             35                  40                  45
Cys Asp Leu Arg Arg Leu Glu Met Tyr Cys Ala Pro Leu Lys Pro Ala
 50                  55                  60
Lys Ser Ala Val Arg Ala Gln Arg His Thr Asp Met Pro Lys Thr Gln
 65                  70                  75                  80
Lys Glu Val His Leu Lys Asn Ala Ser Arg Gly Ser Ala Gly Asn Lys
                 85                  90                  95
Asn Tyr Arg Met
            100
```

<210> SEQ ID NO 9
<211> LENGTH: 142
<212> TYPE: PRT
<213> ORGANISM: Homo sapiens
<220> FEATURE:
<221> NAME/KEY: PEPTIDE
<222> LOCATION: (1)...(142)
<223> OTHER INFORMATION: 3MUT HIGF-1-EB Precursor

<400> SEQUENCE: 9

Thr Leu Cys Gly Ala Glu Leu Val Asp Ala Leu Gln Phe Val Cys Gly

```
                     1               5                  10                 15
Asp Arg Gly Phe Tyr Phe Asn Lys Pro Thr Gly Tyr Gly Ser Ser Ser
             20                  25                  30

Ala Arg Ala Pro Gln Thr Gly Ile Val Asp Glu Cys Cys Phe Arg Ser
             35                  40                  45

Cys Asp Leu Arg Arg Leu Glu Met Tyr Cys Ala Pro Leu Lys Pro Ala
         50                  55                  60

Lys Ser Ala Val Arg Ala Gln Arg His Thr Asp Met Pro Lys Thr Gln
     65                  70                  75                  80

Lys Tyr Gln Pro Pro Ser Thr Asn Lys Asn Thr Lys Ser Gln Arg Arg
                 85                  90                  95

Lys Gly Trp Pro Lys Thr His Pro Gly Gly Glu Gln Lys Glu Gly Thr
             100                 105                 110

Glu Ala Ser Leu Gln Ile Arg Gly Lys Lys Glu Gln Arg Arg Glu
             115                 120                 125

Ile Gly Ser Arg Asn Ala Glu Cys Arg Gly Lys Lys Gly Lys
         130                 135                 140

<210> SEQ ID NO 10
<211> LENGTH: 104
<212> TYPE: PRT
<213> ORGANISM: Homo sapiens
<220> FEATURE:
<221> NAME/KEY: PEPTIDE
<222> LOCATION: (1)...(104)
<223> OTHER INFORMATION: 3 MUT HIGF-1 (Ec) Precursor

<400> SEQUENCE: 10

Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
             20                  25                  30

Arg Ala Pro Gln Thr Gly Ile Val Asp Glu Cys Cys Phe Arg Ser Cys
         35                  40                  45

Asp Leu Arg Arg Leu Glu Met Tyr Cys Ala Pro Leu Lys Pro Ala Lys
     50                  55                  60

Ser Ala Val Arg Ala Gln Arg His Thr Asp Met Pro Lys Thr Gln Lys
 65                  70                  75                  80

Tyr Gln Pro Pro Ser Thr Asn Lys Asn Thr Lys Ser Gln Arg Arg Lys
                 85                  90                  95

Gly Ser Thr Phe Glu Glu Arg Lys
             100

<210> SEQ ID NO 11
<211> LENGTH: 152
<212> TYPE: PRT
<213> ORGANISM: Homo sapiens
<220> FEATURE:
<221> NAME/KEY: PEPTIDE
<222> LOCATION: (1)...(152)
<223> OTHER INFORMATION: HIGF-1-EAB CHIMERIC PRECURSOR CREATES A
      PUTATIVE N-LINKED GLYCOSYLATION SIGNAL AT 92 BY DELETION
<221> NAME/KEY: CARBOHYD
<222> LOCATION: 92

<400> SEQUENCE: 11

Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
             20                  25                  30
```

```
Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala Val Arg Ala Gln Arg His Thr Asp Met Pro Lys Thr Gln
 65                  70                  75                  80

Lys Tyr Gln Pro Pro Ser Thr Asn Lys Asn Ala Ser Arg Gly Ser Ala
                 85                  90                  95

Gly Asn Lys Asn Thr Lys Ser Gln Arg Arg Lys Gly Trp Pro Lys Thr
                100                 105                 110

His Pro Gly Gly Glu Gln Lys Glu Gly Thr Glu Ala Ser Leu Gln Ile
            115                 120                 125

Arg Gly Lys Lys Lys Glu Gln Arg Arg Glu Ile Gly Ser Arg Asn Ala
130                 135                 140

Glu Cys Arg Gly Lys Lys Gly Lys
145                 150
```

<210> SEQ ID NO 12
<211> LENGTH: 350
<212> TYPE: PRT
<213> ORGANISM: Homo sapiens
<220> FEATURE:
<221> NAME/KEY: PEPTIDE
<222> LOCATION: (1)...(350)
<223> OTHER INFORMATION: HIGF-1-EB MULTIMER

<400> SEQUENCE: 12

```
Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
             20                  25                  30

Ala Pro Gln Thr Gly Ile Val Asp Glu Cys Cys Phe Arg Ser Cys Asp
         35                  40                  45

Leu Arg Arg Leu Glu Met Tyr Cys Ala Pro Leu Lys Pro Ala Lys Ser
 50                  55                  60

Ala Val Arg Ala Gln Arg His Thr Asp Met Pro Lys Thr Gln Lys Tyr
 65                  70                  75                  80

Gln Pro Pro Ser Thr Asn Lys Asn Thr Lys Ser Gln Arg Arg Lys Gly
                 85                  90                  95

Trp Pro Lys Thr His Pro Gly Gly Glu Gln Lys Glu Gly Thr Glu Ala
                100                 105                 110

Ser Leu Gln Ile Arg Gly Lys Lys Lys Glu Gln Arg Arg Glu Ile Gly
            115                 120                 125

Ser Arg Asn Ala Glu Arg Ser Val Arg Ala Gln Arg His Thr Asp Met
130                 135                 140

Pro Lys Thr Gln Lys Tyr Gln Pro Pro Ser Thr Asn Lys Asn Thr Lys
145                 150                 155                 160

Ser Gln Arg Arg Lys Gly Trp Pro Lys Thr His Pro Gly Gly Glu Gln
                165                 170                 175

Lys Glu Gly Thr Glu Ala Ser Leu Gln Ile Arg Gly Lys Lys Lys Glu
            180                 185                 190

Gln Arg Arg Glu Ile Gly Ser Arg Asn Ala Glu Arg Ser Val Arg Ala
        195                 200                 205

Gln Arg His Thr Asp Met Pro Lys Thr Gln Lys Tyr Gln Pro Pro Ser
210                 215                 220

Thr Asn Lys Asn Thr Lys Ser Gln Arg Arg Lys Gly Trp Pro Lys Thr
225                 230                 235                 240
```

```
His Pro Gly Gly Glu Gln Lys Glu Gly Thr Glu Ala Ser Leu Gln Ile
                245                 250                 255

Arg Gly Lys Lys Lys Glu Gln Arg Arg Glu Ile Gly Ser Arg Asn Ala
                260                 265                 270

Glu Arg Ser Val Arg Ala Gln Arg His Thr Asp Met Pro Lys Thr Gln
                275                 280                 285

Lys Tyr Gln Pro Pro Ser Thr Asn Lys Asn Thr Lys Ser Gln Arg Arg
                290                 295                 300

Lys Gly Trp Pro Lys Thr His Pro Gly Gly Glu Gln Lys Glu Gly Thr
305                 310                 315                 320

Glu Ala Ser Leu Gln Ile Arg Gly Lys Lys Lys Glu Gln Arg Arg Glu
                325                 330                 335

Ile Gly Ser Arg Asn Ala Glu Cys Arg Gly Lys Lys Gly Lys
                340                 345                 350

<210> SEQ ID NO 13
<211> LENGTH: 150
<212> TYPE: PRT
<213> ORGANISM: Homo sapiens
<220> FEATURE:
<221> NAME/KEY: PEPTIDE
<222> LOCATION: (1)...(150)
<223> OTHER INFORMATION: HIGF-1-EB: N-LINKED GLYCOSYLATION SITE AT
      POSITION N92 AND N100
<221> NAME/KEY: CARBOHYD
<222> LOCATION: 92
<221> NAME/KEY: CARBOHYD
<222> LOCATION: 100

<400> SEQUENCE: 13

Thr Leu Cys Gly Ala Glu Leu Val Asp Ala Leu Gln Phe Val Cys Gly
 1                5                  10                  15

Asp Arg Gly Phe Tyr Phe Asn Lys Pro Thr Gly Tyr Gly Ser Ser Ser
                20                  25                  30

Ala Pro Gln Thr Gly Ile Val Asp Glu Cys Cys Phe Arg Ser Cys Asp
                35                  40                  45

Leu Arg Arg Leu Glu Met Tyr Cys Ala Pro Leu Lys Pro Ala Lys Ser
     50                  55                  60

Ala Val Arg Ala Gln Arg His Thr Asp Met Pro Lys Thr Gln Lys Tyr
65                  70                  75                  80

Gln Pro Pro Ser Thr Asn Lys Asn Ala Ser Arg Gly Ser Ala Gly Asn
                85                  90                  95

Lys Asn Thr Lys Ser Gln Arg Arg Lys Gly Trp Pro Lys Thr His Pro
                100                 105                 110

Gly Gly Glu Gln Lys Glu Gly Thr Glu Ala Ser Leu Gln Ile Arg Gly
                115                 120                 125

Lys Lys Lys Glu Gln Arg Arg Glu Ile Gly Ser Arg Asn Ala Glu Cys
                130                 135                 140

Arg Gly Lys Lys Gly Lys
145                 150

<210> SEQ ID NO 14
<211> LENGTH: 151
<212> TYPE: PRT
<213> ORGANISM: Homo sapiens
<220> FEATURE:
<221> NAME/KEY: PEPTIDE
<222> LOCATION: (1)...(151)
<223> OTHER INFORMATION: HIGF-2-E PRECURSOR DELETION OF P4, DELETION OF
      S5, AND DELETION OF E6; MUTATION OF R38 TO A; AND
      DELETION OF R68 AND DELETION OF D69
```

-continued

```
<400> SEQUENCE: 14

Ala Tyr Arg Thr Leu Cys Gly Gly Glu Leu Val Asp Thr Leu Gln Phe
 1               5                  10                  15

Val Cys Gly Asp Arg Gly Phe Tyr Phe Ser Arg Pro Ala Ser Arg Val
                20                  25                  30

Ser Arg Ala Ser Arg Gly Ile Val Glu Glu Cys Cys Phe Arg Ser Cys
            35                  40                  45

Asp Leu Ala Leu Leu Glu Thr Tyr Cys Ala Thr Pro Ala Lys Ser Glu
50                  55                  60

Val Ser Thr Pro Pro Thr Val Leu Pro Asp Asn Phe Pro Arg Tyr Pro
65                  70                  75                  80

Val Gly Lys Phe Phe Gln Tyr Asp Thr Trp Lys Gln Ser Thr Gln Arg
                85                  90                  95

Leu Arg Arg Gly Leu Pro Ala Leu Leu Arg Ala Arg Arg Gly His Val
            100                 105                 110

Leu Ala Lys Glu Leu Glu Ala Phe Arg Glu Ala Lys Arg His Arg Pro
        115                 120                 125

Leu Ile Ala Leu Pro Thr Gln Asp Pro Ala His Gly Gly Ala Pro Pro
    130                 135                 140

Glu Met Ala Ser Asn Arg Lys
145                 150

<210> SEQ ID NO 15
<211> LENGTH: 101
<212> TYPE: PRT
<213> ORGANISM: Homo sapiens
<220> FEATURE:
<221> NAME/KEY: PEPTIDE
<222> LOCATION: (1)...(101)
<223> OTHER INFORMATION: HIGF-1-EA
<221> NAME/KEY: VARIANT
<222> LOCATION: 1
<223> OTHER INFORMATION: Xaa is non-natural amino acid that is pegylated

<400> SEQUENCE: 15

Xaa Thr Leu Cys Gly Ala Glu Leu Val Asp Ala Leu Gln Phe Val Cys
 1               5                  10                  15

Gly Asp Arg Gly Phe Tyr Phe Asn Lys Pro Thr Gly Tyr Gly Ser Ser
                20                  25                  30

Ser Arg Ala Ala Pro Gln Thr Gly Ile Val Asp Glu Cys Cys Phe Arg
            35                  40                  45

Ser Cys Asp Leu Arg Arg Leu Glu Met Tyr Cys Ala Pro Leu Lys Pro
50                  55                  60

Ala Lys Ser Ala Val Arg Ala Gln Arg His Thr Asp Met Pro Lys Thr
65                  70                  75                  80

Gln Lys Glu Val His Leu Lys Asn Ala Ser Arg Gly Ser Ala Gly Asn
                85                  90                  95

Lys Asn Tyr Arg Met
            100

<210> SEQ ID NO 16
<211> LENGTH: 101
<212> TYPE: PRT
<213> ORGANISM: Homo sapiens
<220> FEATURE:
<221> NAME/KEY: PEPTIDE
<222> LOCATION: (1)...(101)
<223> OTHER INFORMATION: HIGF-1-EA: Deletions at G1, at P2, at E3; R36A;
      at R71
```

```
<400> SEQUENCE: 16

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
             20                  25                  30

Ala Arg Ala Pro Gln Thr Gly Ile Val Asp Glu Cys Cys Phe Arg Ser
         35                  40                  45

Cys Asp Leu Arg Arg Leu Glu Met Tyr Cys Ala Pro Leu Lys Pro Ala
 50                  55                  60

Lys Ser Ala Ser Val Arg Ala Gln Arg His Thr Asp Met Pro Lys Thr
65                  70                  75                  80

Gln Lys Glu Val His Leu Lys Asn Ala Ser Arg Gly Ser Ala Gly Asn
                 85                  90                  95

Lys Asn Tyr Arg Met
             100

<210> SEQ ID NO 17
<211> LENGTH: 101
<212> TYPE: PRT
<213> ORGANISM: Homo sapiens
<220> FEATURE:
<221> NAME/KEY: PEPTIDE
<222> LOCATION: (1)...(101)
<223> OTHER INFORMATION: HIGF-1-EA: deletions at G1, P2, E3; R36A; S72

<400> SEQUENCE: 17

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
             20                  25                  30

Ala Arg Ala Pro Gln Thr Gly Ile Val Asp Glu Cys Cys Phe Arg Ser
         35                  40                  45

Cys Asp Leu Arg Arg Leu Glu Met Tyr Cys Ala Pro Leu Lys Pro Ala
 50                  55                  60

Lys Ser Ala Arg Val Arg Ala Gln Arg His Thr Asp Met Pro Lys Thr
65                  70                  75                  80

Gln Lys Glu Val His Leu Lys Asn Ala Ser Arg Gly Ser Ala Gly Asn
                 85                  90                  95

Lys Asn Tyr Arg Met
             100

<210> SEQ ID NO 18
<211> LENGTH: 100
<212> TYPE: PRT
<213> ORGANISM: Homo sapiens
<220> FEATURE:
<221> NAME/KEY: PEPTIDE
<222> LOCATION: (1)...(100)
<223> OTHER INFORMATION: HIGF-1-EA: deletions at G1, P2, E3; R36A; R71,
      S72

<400> SEQUENCE: 18

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
             20                  25                  30

Ala Arg Ala Pro Gln Thr Gly Ile Val Asp Glu Cys Cys Phe Arg Ser
         35                  40                  45

Cys Asp Leu Arg Arg Leu Glu Met Tyr Cys Ala Pro Leu Lys Pro Ala
 50                  55                  60
```

-continued

Lys Ser Ala Val Arg Ala Gln Arg His Thr Asp Met Pro Lys Thr Gln
 65                  70                  75                  80

Lys Glu Val His Leu Lys Asn Ala Ser Arg Gly Ser Ala Gly Asn Lys
                 85                  90                  95

Asn Tyr Arg Met
            100

<210> SEQ ID NO 19
<211> LENGTH: 101
<212> TYPE: PRT
<213> ORGANISM: Homo sapiens
<220> FEATURE:
<221> NAME/KEY: PEPTIDE
<222> LOCATION: (1)...(0)
<223> OTHER INFORMATION: HIGF-1-EA: deletions at G1, P2, E3; R37A; R71

<400> SEQUENCE: 19

Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
                 20                  25                  30

Arg Ala Ala Pro Gln Thr Gly Ile Val Asp Glu Cys Cys Phe Arg Ser
             35                  40                  45

Cys Asp Leu Arg Arg Leu Glu Met Tyr Cys Ala Pro Leu Lys Pro Ala
 50                  55                  60

Lys Ser Ala Ser Val Arg Ala Gln Arg His Thr Asp Met Pro Lys Thr
 65                  70                  75                  80

Gln Lys Glu Val His Leu Lys Asn Ala Ser Arg Gly Ser Ala Gly Asn
                 85                  90                  95

Lys Asn Tyr Arg Met
            100

<210> SEQ ID NO 20
<211> LENGTH: 101
<212> TYPE: PRT
<213> ORGANISM: Homo sapiens
<220> FEATURE:
<221> NAME/KEY: PEPTIDE
<222> LOCATION: (1)...(101)
<223> OTHER INFORMATION: HIGF-1-EA:  deletions at G1, P2, E3; R37A; S72

<400> SEQUENCE: 20

Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
                 20                  25                  30

Arg Ala Ala Pro Gln Thr Gly Ile Val Asp Glu Cys Cys Phe Arg Ser
             35                  40                  45

Cys Asp Leu Arg Arg Leu Glu Met Tyr Cys Ala Pro Leu Lys Pro Ala
 50                  55                  60

Lys Ser Ala Arg Val Arg Ala Gln Arg His Thr Asp Met Pro Lys Thr
 65                  70                  75                  80

Gln Lys Glu Val His Leu Lys Asn Ala Ser Arg Gly Ser Ala Gly Asn
                 85                  90                  95

Lys Asn Tyr Arg Met
            100

<210> SEQ ID NO 21
<211> LENGTH: 100
<212> TYPE: PRT

```
<213> ORGANISM: Homo sapiens
<220> FEATURE:
<221> NAME/KEY: PEPTIDE
<222> LOCATION: (1)...(100)
<223> OTHER INFORMATION: HIGF-1-EA:  deletions G1, P2, E3, R37; R71

<400> SEQUENCE: 21

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
                20                  25                  30

Arg Ala Pro Gln Thr Gly Ile Val Asp Glu Cys Cys Phe Arg Ser Cys
            35                  40                  45

Asp Leu Arg Arg Leu Glu Met Tyr Cys Ala Pro Leu Lys Pro Ala Lys
        50                  55                  60

Ser Ala Ser Val Arg Ala Gln Arg His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 22
<211> LENGTH: 100
<212> TYPE: PRT
<213> ORGANISM: Homo sapiens
<220> FEATURE:
<221> NAME/KEY: PEPTIDE
<222> LOCATION: (1)...(100)
<223> OTHER INFORMATION: HIGF-1-EA:  deletions at G1, P2, E3, R37; S72

<400> SEQUENCE: 22

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
                20                  25                  30

Arg Ala Pro Gln Thr Gly Ile Val Asp Glu Cys Cys Phe Arg Ser Cys
            35                  40                  45

Asp Leu Arg Arg Leu Glu Met Tyr Cys Ala Pro Leu Lys Pro Ala Lys
        50                  55                  60

Ser Ala Arg Val Arg Ala Gln Arg His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Arg Met
            100

<210> SEQ ID NO 23
<211> LENGTH: 99
<212> TYPE: PRT
<213> ORGANISM: Homo sapiens
<220> FEATURE:
<221> NAME/KEY: PEPTIDE
<222> LOCATION: (1)...(99)
<223> OTHER INFORMATION: HIGF-1-EA:  deletions at G1, P2, E3; R37; R71,
      S72

<400> SEQUENCE: 23

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
                20                  25                  30
```

```
Arg Ala Pro Gln Thr Gly Ile Val Asp Glu Cys Cys Phe Arg Ser Cys
            35                  40                  45

Asp Leu Arg Arg Leu Glu Met Tyr Cys Ala Pro Leu Lys Pro Ala Lys
 50                  55                  60

Ser Ala Val Arg Ala Gln Arg His Thr Asp Met Pro Lys Thr Gln Lys
 65                  70                  75                  80

Glu Val His Leu Lys Asn Ala Ser Arg Gly Ser Ala Gly Asn Lys Asn
                 85                  90                  95

Tyr Arg Met

<210> SEQ ID NO 24
<211> LENGTH: 143
<212> TYPE: PRT
<213> ORGANISM: Homo sapiens
<220> FEATURE:
<221> NAME/KEY: PEPTIDE
<222> LOCATION: (1)...(143)
<223> OTHER INFORMATION: HIGF-1-EB:  deletions G1, P2, E3; R36A; R71

<400> SEQUENCE: 24

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Ala Arg Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala Ser Val Arg Ala Gln Arg His Thr Asp Met Pro Lys Thr
 65                  70                  75                  80

Gln Lys Tyr Gln Pro Pro Ser Thr Asn Lys Asn Thr Lys Ser Gln Arg
                 85                  90                  95

Arg Lys Gly Trp Pro Lys Thr His Pro Gly Gly Glu Gln Lys Glu Gly
            100                 105                 110

Thr Glu Ala Ser Leu Gln Ile Arg Gly Lys Lys Lys Glu Gln Arg Arg
        115                 120                 125

Glu Ile Gly Ser Arg Asn Ala Glu Cys Arg Gly Lys Lys Gly Lys
    130                 135                 140

<210> SEQ ID NO 25
<211> LENGTH: 143
<212> TYPE: PRT
<213> ORGANISM: Homo sapiens
<220> FEATURE:
<221> NAME/KEY: PEPTIDE
<222> LOCATION: (1)...(143)
<223> OTHER INFORMATION: HIGF-1-EB:  deletions at G1, P2, E3; R36A; S72

<400> SEQUENCE: 25

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Ala Arg Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala Arg Val Arg Ala Gln Arg His Thr Asp Met Pro Lys Thr
 65                  70                  75                  80
```

Gln Lys Tyr Gln Pro Pro Ser Thr Asn Lys Asn Thr Lys Ser Gln Arg
                85                  90                  95

Arg Lys Gly Trp Pro Lys Thr His Pro Gly Gly Glu Gln Lys Glu Gly
            100                 105                 110

Thr Glu Ala Ser Leu Gln Ile Arg Gly Lys Lys Lys Glu Gln Arg Arg
            115                 120                 125

Glu Ile Gly Ser Arg Asn Ala Glu Cys Arg Gly Lys Lys Gly Lys
            130                 135                 140

<210> SEQ ID NO 26
<211> LENGTH: 143
<212> TYPE: PRT
<213> ORGANISM: Homo sapiens
<220> FEATURE:
<221> NAME/KEY: PEPTIDE
<222> LOCATION: (1)...(143)
<223> OTHER INFORMATION: HIGF-1-EB: deletions at G1, P2, E3; R37A; R71

<400> SEQUENCE: 26

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
            35                  40                  45

Cys Asp Leu Arg Arg Leu Glu Met Tyr Cys Ala Pro Leu Lys Pro Ala
        50                  55                  60

Lys Ser Ala Ser Val Arg Ala Gln Arg His Thr Asp Met Pro Lys Thr
65                  70                  75                  80

Gln Lys Tyr Gln Pro Pro Ser Thr Asn Lys Asn Thr Lys Ser Gln Arg
                85                  90                  95

Arg Lys Gly Trp Pro Lys Thr His Pro Gly Gly Glu Gln Lys Glu Gly
            100                 105                 110

Thr Glu Ala Ser Leu Gln Ile Arg Gly Lys Lys Lys Glu Gln Arg Arg
            115                 120                 125

Glu Ile Gly Ser Arg Asn Ala Glu Cys Arg Gly Lys Lys Gly Lys
            130                 135                 140

<210> SEQ ID NO 27
<211> LENGTH: 143
<212> TYPE: PRT
<213> ORGANISM: Homo sapiens
<220> FEATURE:
<221> NAME/KEY: PEPTIDE
<222> LOCATION: (1)...(143)
<223> OTHER INFORMATION: HIGF-1-EB: deletions at G1, P2, E3; R37A; S72

<400> SEQUENCE: 27

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
            35                  40                  45

Cys Asp Leu Arg Arg Leu Glu Met Tyr Cys Ala Pro Leu Lys Pro Ala
        50                  55                  60

Lys Ser Ala Arg Val Arg Ala Gln Arg His Thr Asp Met Pro Lys Thr
65                  70                  75                  80

Gln Lys Tyr Gln Pro Pro Ser Thr Asn Lys Asn Thr Lys Ser Gln Arg

```
                    85                  90                  95

Arg Lys Gly Trp Pro Lys Thr His Pro Gly Gly Glu Gln Lys Glu Gly
            100                 105                 110

Thr Glu Ala Ser Leu Gln Ile Arg Gly Lys Lys Glu Gln Arg Arg
            115                 120                 125

Glu Ile Gly Ser Arg Asn Ala Glu Cys Arg Gly Lys Lys Gly Lys
            130                 135                 140

<210> SEQ ID NO 28
<211> LENGTH: 142
<212> TYPE: PRT
<213> ORGANISM: Homo sapiens
<220> FEATURE:
<221> NAME/KEY: PEPTIDE
<222> LOCATION: (1)...(143)
<223> OTHER INFORMATION: HIGF-1-EB: deletions at G1, P2, E3; R37A; R71,
      S72

<400> SEQUENCE: 28

Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
             20                  25                  30

Arg Ala Ala Pro Gln Thr Gly Ile Val Asp Glu Cys Cys Phe Arg Ser
             35                  40                  45

Cys Asp Leu Arg Arg Leu Glu Met Tyr Cys Ala Pro Leu Lys Pro Ala
        50                  55                  60

Lys Ser Ala Val Arg Ala Gln Arg His Thr Asp Met Pro Lys Thr Gln
 65                  70                  75                  80

Lys Tyr Gln Pro Pro Ser Thr Asn Lys Asn Thr Lys Ser Gln Arg Arg
                 85                  90                  95

Lys Gly Trp Pro Lys Thr His Pro Gly Gly Glu Gln Lys Glu Gly Thr
            100                 105                 110

Glu Ala Ser Leu Gln Ile Arg Gly Lys Lys Glu Gln Arg Arg Glu
            115                 120                 125

Ile Gly Ser Arg Asn Ala Glu Cys Arg Gly Lys Lys Gly Lys
            130                 135                 140

<210> SEQ ID NO 29
<211> LENGTH: 142
<212> TYPE: PRT
<213> ORGANISM: Homo sapiens
<220> FEATURE:
<221> NAME/KEY: PEPTIDE
<222> LOCATION: (1)...(142)
<223> OTHER INFORMATION: HIGF-1-EB: deletions at G1, P2, E3, R37; R71

<400> SEQUENCE: 29

Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
             20                  25                  30

Arg Ala Pro Gln Thr Gly Ile Val Asp Glu Cys Cys Phe Arg Ser Cys
             35                  40                  45

Asp Leu Arg Arg Leu Glu Met Tyr Cys Ala Pro Leu Lys Pro Ala Lys
        50                  55                  60

Ser Ala Ser Val Arg Ala Gln Arg His Thr Asp Met Pro Lys Thr Gln
 65                  70                  75                  80

Lys Tyr Gln Pro Pro Ser Thr Asn Lys Asn Thr Lys Ser Gln Arg Arg
                 85                  90                  95
```

```
Lys Gly Trp Pro Lys Thr His Pro Gly Gly Glu Gln Lys Glu Gly Thr
            100                 105                 110

Glu Ala Ser Leu Gln Ile Arg Gly Lys Lys Glu Gln Arg Arg Glu
        115                 120                 125

Ile Gly Ser Arg Asn Ala Glu Cys Arg Gly Lys Lys Gly Lys
    130                 135                 140

<210> SEQ ID NO 30
<211> LENGTH: 142
<212> TYPE: PRT
<213> ORGANISM: Homo sapiens
<220> FEATURE:
<221> NAME/KEY: PEPTIDE
<222> LOCATION: (1)...(142)
<223> OTHER INFORMATION: HIGF-1-EB:  deletions at G1, P2, E3, R37; S72

<400> SEQUENCE: 30

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Ala Pro Gln Thr Gly Ile Val Asp Glu Cys Cys Phe Arg Ser Cys
        35                  40                  45

Asp Leu Arg Arg Leu Glu Met Tyr Cys Ala Pro Leu Lys Pro Ala Lys
    50                  55                  60

Ser Ala Arg Val Arg Ala Gln Arg His Thr Asp Met Pro Lys Thr Gln
65                  70                  75                  80

Lys Tyr Gln Pro Pro Ser Thr Asn Lys Asn Thr Lys Ser Gln Arg Arg
                85                  90                  95

Lys Gly Trp Pro Lys Thr His Pro Gly Gly Glu Gln Lys Glu Gly Thr
            100                 105                 110

Glu Ala Ser Leu Gln Ile Arg Gly Lys Lys Glu Gln Arg Arg Glu
        115                 120                 125

Ile Gly Ser Arg Asn Ala Glu Cys Arg Gly Lys Lys Gly Lys
    130                 135                 140

<210> SEQ ID NO 31
<211> LENGTH: 141
<212> TYPE: PRT
<213> ORGANISM: Homo sapiens
<220> FEATURE:
<221> NAME/KEY: PEPTIDE
<222> LOCATION: (1)...(141)
<223> OTHER INFORMATION: HIGF-1-EB:  deletions at G1, P2, E3, R37; R71,
      S72

<400> SEQUENCE: 31

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Ala Pro Gln Thr Gly Ile Val Asp Glu Cys Cys Phe Arg Ser Cys
        35                  40                  45

Asp Leu Arg Arg Leu Glu Met Tyr Cys Ala Pro Leu Lys Pro Ala Lys
    50                  55                  60

Ser Ala Val Arg Ala Gln Arg His Thr Asp Met Pro Lys Thr Gln Lys
65                  70                  75                  80

Tyr Gln Pro Pro Ser Thr Asn Lys Asn Thr Lys Ser Gln Arg Arg Lys
                85                  90                  95
```

```
Gly Trp Pro Lys Thr His Pro Gly Glu Gln Lys Glu Gly Thr Glu
            100                 105                 110

Ala Ser Leu Gln Ile Arg Gly Lys Lys Glu Gln Arg Arg Glu Ile
        115                 120                 125

Gly Ser Arg Asn Ala Glu Cys Arg Gly Lys Lys Gly Lys
    130                 135                 140

<210> SEQ ID NO 32
<211> LENGTH: 106
<212> TYPE: PRT
<213> ORGANISM: Homo sapiens
<220> FEATURE:
<221> NAME/KEY: PEPTIDE
<222> LOCATION: (1)...(106)
<223> OTHER INFORMATION: HIGF-1-EC:  deletions at G1, P2, E3; R36A; R71

<400> SEQUENCE: 32

Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
                 20                  25                  30

Ala Arg Ala Pro Gln Thr Gly Ile Val Asp Glu Cys Cys Phe Arg Ser
             35                  40                  45

Cys Asp Leu Arg Arg Leu Glu Met Tyr Cys Ala Pro Leu Lys Pro Ala
 50                  55                  60

Lys Ser Ala Ser Val Arg Ala Gln Arg His Thr Asp Met Pro Lys Thr
 65                  70                  75                  80

Gln Lys Tyr Gln Pro Pro Ser Thr Asn Lys Asn Thr Lys Ser Gln Arg
                 85                  90                  95

Arg Lys Gly Ser Thr Phe Glu Glu Arg Lys
                100                 105

<210> SEQ ID NO 33
<211> LENGTH: 106
<212> TYPE: PRT
<213> ORGANISM: Homo sapiens
<220> FEATURE:
<221> NAME/KEY: PEPTIDE
<222> LOCATION: (1)...(0)
<223> OTHER INFORMATION: HIGF-1-EC:  deletions at G1, P2, E3; R36A; S72

<400> SEQUENCE: 33

Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
                 20                  25                  30

Ala Arg Ala Pro Gln Thr Gly Ile Val Asp Glu Cys Cys Phe Arg Ser
             35                  40                  45

Cys Asp Leu Arg Arg Leu Glu Met Tyr Cys Ala Pro Leu Lys Pro Ala
 50                  55                  60

Lys Ser Ala Arg Val Arg Ala Gln Arg His Thr Asp Met Pro Lys Thr
 65                  70                  75                  80

Gln Lys Tyr Gln Pro Pro Ser Thr Asn Lys Asn Thr Lys Ser Gln Arg
                 85                  90                  95

Arg Lys Gly Ser Thr Phe Glu Glu Arg Lys
                100                 105

<210> SEQ ID NO 34
<211> LENGTH: 105
<212> TYPE: PRT
<213> ORGANISM: Homo sapiens
```

```
<220> FEATURE:
<221> NAME/KEY: DNA_BIND
<222> LOCATION: (1)...(105)
<223> OTHER INFORMATION: HIGF-1-EC: deletions at G1, P2, E3; R36A; R71,
      S72

<400> SEQUENCE: 34

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Ala Arg Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala Val Arg Ala Gln Arg His Thr Asp Met Pro Lys Thr Gln
 65                  70                  75                  80

Lys Tyr Gln Pro Pro Ser Thr Asn Lys Asn Thr Lys Ser Gln Arg Arg
                85                  90                  95

Lys Gly Ser Thr Phe Glu Glu Arg Lys
            100                 105

<210> SEQ ID NO 35
<211> LENGTH: 106
<212> TYPE: PRT
<213> ORGANISM: Homo sapiens
<220> FEATURE:
<221> NAME/KEY: PEPTIDE
<222> LOCATION: (1)...(105)
<223> OTHER INFORMATION: HIGF-1-EC:  deletions at G1, P2, E2; R37A; R71

<400> SEQUENCE: 35

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala Ser Val Arg Ala Gln Arg His Thr Asp Met Pro Lys Thr
 65                  70                  75                  80

Gln Lys Tyr Gln Pro Pro Ser Thr Asn Lys Asn Thr Lys Ser Gln Arg
                85                  90                  95

Arg Lys Gly Ser Thr Phe Glu Glu Arg Lys
            100                 105

<210> SEQ ID NO 36
<211> LENGTH: 106
<212> TYPE: PRT
<213> ORGANISM: Homo sapiens
<220> FEATURE:
<221> NAME/KEY: PEPTIDE
<222> LOCATION: (1)...(106)
<223> OTHER INFORMATION: HIGF-1-EC:  deletions at G1, P2, E3; R37A; S72

<400> SEQUENCE: 36

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30
```

```
Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala Arg Val Arg Ala Gln Arg His Thr Asp Met Pro Lys Thr
 65                  70                  75                  80

Gln Lys Tyr Gln Pro Pro Ser Thr Asn Lys Asn Thr Lys Ser Gln Arg
                 85                  90                  95

Arg Lys Gly Ser Thr Phe Glu Glu Arg Lys
             100                 105

<210> SEQ ID NO 37
<211> LENGTH: 105
<212> TYPE: PRT
<213> ORGANISM: Homo sapiens
<220> FEATURE:
<221> NAME/KEY: PEPTIDE
<222> LOCATION: (1)...(105)
<223> OTHER INFORMATION: HIGF-1-EC:  deletions at G1, P2, E3; R37A; R71,
      S72

<400> SEQUENCE: 37

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
             20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala Val Arg Ala Gln Arg His Thr Asp Met Pro Lys Thr Gln
 65                  70                  75                  80

Lys Tyr Gln Pro Pro Ser Thr Asn Lys Asn Thr Lys Ser Gln Arg Arg
                 85                  90                  95

Lys Gly Ser Thr Phe Glu Glu Arg Lys
             100                 105

<210> SEQ ID NO 38
<211> LENGTH: 105
<212> TYPE: PRT
<213> ORGANISM: Homo sapiens
<220> FEATURE:
<221> NAME/KEY: PEPTIDE
<222> LOCATION: (1)...(105)
<223> OTHER INFORMATION: HIGF-1-EC:  deletions at G1, P2, E3, R37, R71

<400> SEQUENCE: 38

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
             20                  25                  30

Arg Ala Pro Gln Thr Gly Ile Val Asp Glu Cys Cys Phe Arg Ser Cys
        35                  40                  45

Asp Leu Arg Arg Leu Glu Met Tyr Cys Ala Pro Leu Lys Pro Ala Lys
 50                  55                  60

Ser Ala Ser Val Arg Ala Gln Arg His Thr Asp Met Pro Lys Thr Gln
 65                  70                  75                  80

Lys Tyr Gln Pro Pro Ser Thr Asn Lys Asn Thr Lys Ser Gln Arg Arg
                 85                  90                  95

Lys Gly Ser Thr Phe Glu Glu Arg Lys
```

```
<210> SEQ ID NO 39
<211> LENGTH: 105
<212> TYPE: PRT
<213> ORGANISM: Homo sapiens
<220> FEATURE:
<221> NAME/KEY: PEPTIDE
<222> LOCATION: (1)...(105)
<223> OTHER INFORMATION: HIGF-1-EC:  deletions at G1, P2, E3, R37, S72

<400> SEQUENCE: 39

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
                20                  25                  30

Arg Ala Pro Gln Thr Gly Ile Val Asp Glu Cys Cys Phe Arg Ser Cys
            35                  40                  45

Asp Leu Arg Arg Leu Glu Met Tyr Cys Ala Pro Leu Lys Pro Ala Lys
50                  55                  60

Ser Ala Arg Val Arg Ala Gln Arg His Thr Asp Met Pro Lys Thr Gln
65                  70                  75                  80

Lys Tyr Gln Pro Pro Ser Thr Asn Lys Asn Thr Lys Ser Gln Arg Arg
                85                  90                  95

Lys Gly Ser Thr Phe Glu Glu Arg Lys
            100                 105

<210> SEQ ID NO 40
<211> LENGTH: 153
<212> TYPE: PRT
<213> ORGANISM: Homo sapiens
<220> FEATURE:
<221> NAME/KEY: PEPTIDE
<222> LOCATION: (1)...(153)
<223> OTHER INFORMATION: HIGF-1-EAB:  deletions at G1, P2, E3; R36A;
      R71;INSERTION OF EA AA 93-102 BETWEEN AA 95 AND 96
      OF EB (I.E., "EAB")

<400> SEQUENCE: 40

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
                20                  25                  30

Ala Arg Ala Pro Gln Thr Gly Ile Val Asp Glu Cys Cys Phe Arg Ser
            35                  40                  45

Cys Asp Leu Arg Arg Leu Glu Met Tyr Cys Ala Pro Leu Lys Pro Ala
50                  55                  60

Lys Ser Ala Ser Val Arg Ala Gln Arg His Thr Asp Met Pro Lys Thr
65                  70                  75                  80

Gln Lys Tyr Gln Pro Pro Ser Thr Asn Lys Asn Ala Ser Arg Gly Ser
                85                  90                  95

Ala Gly Asn Lys Asn Thr Lys Ser Gln Arg Arg Lys Gly Trp Pro Lys
            100                 105                 110

Thr His Pro Gly Gly Glu Gln Lys Glu Gly Thr Glu Ala Ser Leu Gln
        115                 120                 125

Ile Arg Gly Lys Lys Glu Gln Arg Glu Ile Gly Ser Arg Asn
    130                 135                 140

Ala Glu Cys Arg Gly Lys Lys Gly Lys
145                 150
```

```
<210> SEQ ID NO 41
<211> LENGTH: 153
<212> TYPE: PRT
<213> ORGANISM: Homo sapiens
<220> FEATURE:
<221> NAME/KEY: PEPTIDE
<222> LOCATION: (1)...(153)
<223> OTHER INFORMATION: HIGF-1-EAB:  deletions at G1, P2, E3; R37A; R71

<400> SEQUENCE: 41

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Ser Val Arg Ala Gln Arg His Thr Asp Met Pro Lys Thr
65                  70                  75                  80

Gln Lys Tyr Gln Pro Pro Ser Thr Asn Lys Asn Ala Ser Arg Gly Ser
                85                  90                  95

Ala Gly Asn Lys Asn Thr Lys Ser Gln Arg Arg Lys Gly Trp Pro Lys
            100                 105                 110

Thr His Pro Gly Gly Glu Gln Lys Glu Gly Thr Glu Ala Ser Leu Gln
        115                 120                 125

Ile Arg Gly Lys Lys Lys Glu Gln Arg Arg Glu Ile Gly Ser Arg Asn
    130                 135                 140

Ala Glu Cys Arg Gly Lys Lys Gly Lys
145                 150

<210> SEQ ID NO 42
<211> LENGTH: 152
<212> TYPE: PRT
<213> ORGANISM: Homo sapiens
<220> FEATURE:
<221> NAME/KEY: PEPTIDE
<222> LOCATION: (1)...(152)
<223> OTHER INFORMATION: HIGF-1-EAB:  deletions at G1, P2, E3, R37, R71

<400> SEQUENCE: 42

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Ala Pro Gln Thr Gly Ile Val Asp Glu Cys Cys Phe Arg Ser Cys
        35                  40                  45

Asp Leu Arg Arg Leu Glu Met Tyr Cys Ala Pro Leu Lys Pro Ala Lys
    50                  55                  60

Ser Ala Ser Val Arg Ala Gln Arg His Thr Asp Met Pro Lys Thr Gln
65                  70                  75                  80

Lys Tyr Gln Pro Pro Ser Thr Asn Lys Asn Ala Ser Arg Gly Ser Ala
                85                  90                  95

Gly Asn Lys Asn Thr Lys Ser Gln Arg Arg Lys Gly Trp Pro Lys Thr
            100                 105                 110

His Pro Gly Gly Glu Gln Lys Glu Gly Thr Glu Ala Ser Leu Gln Ile
        115                 120                 125

Arg Gly Lys Lys Lys Glu Gln Arg Arg Glu Ile Gly Ser Arg Asn Ala
    130                 135                 140
```

```
Glu Cys Arg Gly Lys Lys Gly Lys
145                 150
```

```
<210> SEQ ID NO 43
<211> LENGTH: 153
<212> TYPE: PRT
<213> ORGANISM: Homo sapiens
<220> FEATURE:
<221> NAME/KEY: PEPTIDE
<222> LOCATION: (1)...(153)
<223> OTHER INFORMATION: HIGF-1-EAB:  deletions at G1, P2, E3; R36A; S72

<400> SEQUENCE: 43

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Ala Arg Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala Arg Val Arg Ala Gln Arg His Thr Asp Met Pro Lys Thr
65                   70                  75                  80

Gln Lys Tyr Gln Pro Pro Ser Thr Asn Lys Asn Ala Ser Arg Gly Ser
                85                  90                  95

Ala Gly Asn Lys Asn Thr Lys Ser Gln Arg Arg Lys Gly Trp Pro Lys
            100                 105                 110

Thr His Pro Gly Gly Glu Gln Lys Glu Gly Thr Glu Ala Ser Leu Gln
        115                 120                 125

Ile Arg Gly Lys Lys Lys Glu Gln Arg Arg Glu Ile Gly Ser Arg Asn
130                 135                 140

Ala Glu Cys Arg Gly Lys Lys Gly Lys
145                 150
```

```
<210> SEQ ID NO 44
<211> LENGTH: 153
<212> TYPE: PRT
<213> ORGANISM: Homo sapiens
<220> FEATURE:
<221> NAME/KEY: PEPTIDE
<222> LOCATION: (1)...(153)
<223> OTHER INFORMATION: HIGF-1-EAB:  G1, P2, E3; R37A; S72

<400> SEQUENCE: 44

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala Arg Val Arg Ala Gln Arg His Thr Asp Met Pro Lys Thr
65                   70                  75                  80

Gln Lys Tyr Gln Pro Pro Ser Thr Asn Lys Asn Ala Ser Arg Gly Ser
                85                  90                  95

Ala Gly Asn Lys Asn Thr Lys Ser Gln Arg Arg Lys Gly Trp Pro Lys
            100                 105                 110

Thr His Pro Gly Gly Glu Gln Lys Glu Gly Thr Glu Ala Ser Leu Gln
        115                 120                 125
```

Ile Arg Gly Lys Lys Lys Glu Gln Arg Glu Ile Gly Ser Arg Asn
130                 135                 140

Ala Glu Cys Arg Gly Lys Lys Gly Lys
145                 150

<210> SEQ ID NO 45
<211> LENGTH: 152
<212> TYPE: PRT
<213> ORGANISM: Homo sapiens
<220> FEATURE:
<221> NAME/KEY: PEPTIDE
<222> LOCATION: (1)...(152)
<223> OTHER INFORMATION: HIGF-1-EAB:  G1, P2, E3, R37, S72

<400> SEQUENCE: 45

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Arg Ala Pro Gln Thr Gly Ile Val Asp Glu Cys Cys Phe Arg Ser Cys
            35                  40                  45

Asp Leu Arg Arg Leu Glu Met Tyr Cys Ala Pro Leu Lys Pro Ala Lys
50                  55                  60

Ser Ala Arg Val Arg Ala Gln Arg His Thr Asp Met Pro Lys Thr Gln
65                  70                  75                  80

Lys Tyr Gln Pro Pro Ser Thr Asn Lys Asn Ala Ser Arg Gly Ser Ala
                85                  90                  95

Gly Asn Lys Asn Thr Lys Ser Gln Arg Arg Lys Gly Trp Pro Lys Thr
            100                 105                 110

His Pro Gly Gly Glu Gln Lys Glu Gly Thr Glu Ala Ser Leu Gln Ile
        115                 120                 125

Arg Gly Lys Lys Lys Glu Gln Arg Arg Glu Ile Gly Ser Arg Asn Ala
130                 135                 140

Glu Cys Arg Gly Lys Lys Gly Lys
145                 150

<210> SEQ ID NO 46
<211> LENGTH: 152
<212> TYPE: PRT
<213> ORGANISM: Homo sapiens
<220> FEATURE:
<221> NAME/KEY: PEPTIDE
<222> LOCATION: (1)...(152)
<223> OTHER INFORMATION: HIGF-1-EAB:  G1, P2, E3; R36A; R71, S72

<400> SEQUENCE: 46

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Ala Arg Ala Pro Gln Thr Gly Ile Val Asp Glu Cys Cys Phe Arg Ser
            35                  40                  45

Cys Asp Leu Arg Arg Leu Glu Met Tyr Cys Ala Pro Leu Lys Pro Ala
50                  55                  60

Lys Ser Ala Val Arg Ala Gln Arg His Thr Asp Met Pro Lys Thr Gln
65                  70                  75                  80

Lys Tyr Gln Pro Pro Ser Thr Asn Lys Asn Ala Ser Arg Gly Ser Ala
                85                  90                  95

Gly Asn Lys Asn Thr Lys Ser Gln Arg Arg Lys Gly Trp Pro Lys Thr

```
                        100                 105                 110

His Pro Gly Gly Glu Gln Lys Glu Gly Thr Glu Ala Ser Leu Gln Ile
        115                 120                 125

Arg Gly Lys Lys Lys Glu Gln Arg Arg Glu Ile Gly Ser Arg Asn Ala
    130                 135                 140

Glu Cys Arg Gly Lys Lys Gly Lys
145                 150

<210> SEQ ID NO 47
<211> LENGTH: 151
<212> TYPE: PRT
<213> ORGANISM: Homo sapiens
<220> FEATURE:
<221> NAME/KEY: PEPTIDE
<222> LOCATION: (1)...(151)
<223> OTHER INFORMATION: HIGF-1-EAB:  G1, P2, E3, R37, R71, S72

<400> SEQUENCE: 47

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Ala Pro Gln Thr Gly Ile Val Asp Glu Cys Cys Phe Arg Ser Cys
        35                  40                  45

Asp Leu Arg Arg Leu Glu Met Tyr Cys Ala Pro Leu Lys Pro Ala Lys
    50                  55                  60

Ser Ala Val Arg Ala Gln Arg His Thr Asp Met Pro Lys Thr Gln Lys
65                  70                  75                  80

Tyr Gln Pro Pro Ser Thr Asn Lys Asn Ala Ser Arg Gly Ser Ala Gly
                85                  90                  95

Asn Lys Asn Thr Lys Ser Gln Arg Arg Lys Gly Trp Pro Lys Thr His
            100                 105                 110

Pro Gly Gly Glu Gln Lys Glu Gly Thr Glu Ala Ser Leu Gln Ile Arg
        115                 120                 125

Gly Lys Lys Lys Glu Gln Arg Arg Glu Ile Gly Ser Arg Asn Ala Glu
    130                 135                 140

Cys Arg Gly Lys Lys Gly Lys
145                 150

<210> SEQ ID NO 48
<211> LENGTH: 101
<212> TYPE: PRT
<213> ORGANISM: Homo sapiens
<220> FEATURE:
<221> NAME/KEY: PEPTIDE
<222> LOCATION: (1)...(101)
<223> OTHER INFORMATION: HIGF-1-EA:  P2, E3; R37A; R71, S72

<400> SEQUENCE: 48

Gly Thr Leu Cys Gly Ala Glu Leu Val Asp Ala Leu Gln Phe Val Cys
 1               5                  10                  15

Gly Asp Arg Gly Phe Tyr Phe Asn Lys Pro Thr Gly Tyr Gly Ser Ser
            20                  25                  30

Ser Arg Ala Ala Pro Gln Thr Gly Ile Val Asp Glu Cys Cys Phe Arg
        35                  40                  45

Ser Cys Asp Leu Arg Arg Leu Glu Met Tyr Cys Ala Pro Leu Lys Pro
    50                  55                  60

Ala Lys Ser Ala Val Arg Ala Gln Arg His Thr Asp Met Pro Lys Thr
65                  70                  75                  80
```

```
Gln Lys Glu Val His Leu Lys Asn Ala Ser Arg Gly Ser Ala Gly Asn
            85                  90                  95

Lys Asn Tyr Arg Met
            100
```

<210> SEQ ID NO 49
<211> LENGTH: 143
<212> TYPE: PRT
<213> ORGANISM: Homo sapiens
<220> FEATURE:
<221> NAME/KEY: PEPTIDE
<222> LOCATION: (1)...(143)
<223> OTHER INFORMATION: HIGF-1-EB: P2, E3; R37A; R71, S72

<400> SEQUENCE: 49

```
Gly Thr Leu Cys Gly Ala Glu Leu Val Asp Ala Leu Gln Phe Val Cys
 1               5                  10                  15

Gly Asp Arg Gly Phe Tyr Phe Asn Lys Pro Thr Gly Tyr Gly Ser Ser
            20                  25                  30

Ser Arg Ala Ala Pro Gln Thr Gly Ile Val Asp Glu Cys Cys Phe Arg
        35                  40                  45

Ser Cys Asp Leu Arg Arg Leu Glu Met Tyr Cys Ala Pro Leu Lys Pro
 50                  55                  60

Ala Lys Ser Ala Val Arg Ala Gln Arg His Thr Asp Met Pro Lys Thr
65                  70                  75                  80

Gln Lys Tyr Gln Pro Pro Ser Thr Asn Lys Asn Thr Lys Ser Gln Arg
                85                  90                  95

Arg Lys Gly Trp Pro Lys Thr His Pro Gly Gly Glu Gln Lys Glu Gly
            100                 105                 110

Thr Glu Ala Ser Leu Gln Ile Arg Gly Lys Lys Lys Glu Gln Arg Arg
        115                 120                 125

Glu Ile Gly Ser Arg Asn Ala Glu Cys Arg Gly Lys Lys Gly Lys
    130                 135                 140
```

<210> SEQ ID NO 50
<211> LENGTH: 346
<212> TYPE: PRT
<213> ORGANISM: Homo sapiens
<220> FEATURE:
<221> NAME/KEY: PEPTIDE
<222> LOCATION: (1)...(346)
<223> OTHER INFORMATION: HIGF-1-EB MULTIMER: (G1, P2, E3; R37A)-
    3XEB(R71, S72, C-TERM 7 AA)-EB(R71, S72)

<400> SEQUENCE: 50

```
Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala Val Arg Ala Gln Arg His Thr Asp Met Pro Lys Thr Gln
65                  70                  75                  80

Lys Tyr Gln Pro Pro Ser Thr Asn Lys Asn Thr Lys Ser Gln Arg Arg
                85                  90                  95

Lys Gly Trp Pro Lys Thr His Pro Gly Gly Glu Gln Lys Glu Gly Thr
            100                 105                 110

Glu Ala Ser Leu Gln Ile Arg Gly Lys Lys Lys Glu Gln Arg Arg Glu
```

```
                    115                 120                 125
Ile Gly Ser Arg Asn Ala Glu Val Arg Ala Gln Arg His Thr Asp Met
    130                 135                 140

Pro Lys Thr Gln Lys Tyr Gln Pro Pro Ser Thr Asn Lys Asn Thr Lys
145                 150                 155                 160

Ser Gln Arg Arg Lys Gly Trp Pro Lys Thr His Pro Gly Gly Glu Gln
                165                 170                 175

Lys Glu Gly Thr Glu Ala Ser Leu Gln Ile Arg Gly Lys Lys Glu
            180                 185                 190

Gln Arg Arg Glu Ile Gly Ser Arg Asn Ala Glu Val Arg Ala Gln Arg
        195                 200                 205

His Thr Asp Met Pro Lys Thr Gln Lys Tyr Gln Pro Pro Ser Thr Asn
    210                 215                 220

Lys Asn Thr Lys Ser Gln Arg Arg Lys Gly Trp Pro Lys Thr His Pro
225                 230                 235                 240

Gly Gly Glu Gln Lys Glu Gly Thr Glu Ala Ser Leu Gln Ile Arg Gly
                245                 250                 255

Lys Lys Lys Glu Gln Arg Arg Glu Ile Gly Ser Arg Asn Ala Glu Val
            260                 265                 270

Arg Ala Gln Arg His Thr Asp Met Pro Lys Thr Gln Lys Tyr Gln Pro
        275                 280                 285

Pro Ser Thr Asn Lys Asn Thr Lys Ser Gln Arg Arg Lys Gly Trp Pro
    290                 295                 300

Lys Thr His Pro Gly Gly Glu Gln Lys Glu Gly Thr Glu Ala Ser Leu
305                 310                 315                 320

Gln Ile Arg Gly Lys Lys Lys Glu Gln Arg Arg Glu Ile Gly Ser Arg
                325                 330                 335

Asn Ala Glu Cys Arg Gly Lys Lys Gly Lys
            340                 345

<210> SEQ ID NO 51
<211> LENGTH: 347
<212> TYPE: PRT
<213> ORGANISM: Homo sapiens
<220> FEATURE:
<221> NAME/KEY: PEPTIDE
<222> LOCATION: (1)...(347)
<223> OTHER INFORMATION: HIGF-1-EB MULTIMER: (P2, E3; R37A)-3XEB(R71,
      S72, C-TERM 7 AA)-EB R71, S72)

<400> SEQUENCE: 51

Gly Thr Leu Cys Gly Ala Glu Leu Val Asp Ala Leu Gln Phe Val Cys
  1               5                  10                  15

Gly Asp Arg Gly Phe Tyr Phe Asn Lys Pro Thr Gly Tyr Gly Ser Ser
                20                  25                  30

Ser Arg Ala Ala Pro Gln Thr Gly Ile Val Asp Glu Cys Cys Phe Arg
            35                  40                  45

Ser Cys Asp Leu Arg Arg Leu Glu Met Tyr Cys Ala Pro Leu Lys Pro
    50                  55                  60

Ala Lys Ser Ala Val Arg Ala Gln Arg His Thr Asp Met Pro Lys Thr
65                  70                  75                  80

Gln Lys Tyr Gln Pro Pro Ser Thr Asn Lys Asn Thr Lys Ser Gln Arg
                85                  90                  95

Arg Lys Gly Trp Pro Lys Thr His Pro Gly Gly Glu Gln Lys Glu Gly
            100                 105                 110

Thr Glu Ala Ser Leu Gln Ile Arg Gly Lys Lys Lys Glu Gln Arg Arg
    115                 120                 125
```

-continued

```
Glu Ile Gly Ser Arg Asn Ala Glu Val Arg Ala Gln Arg His Thr Asp
    130                 135                 140

Met Pro Lys Thr Gln Lys Tyr Gln Pro Pro Ser Thr Asn Lys Asn Thr
145                 150                 155                 160

Lys Ser Gln Arg Arg Lys Gly Trp Pro Lys Thr His Pro Gly Gly Glu
                165                 170                 175

Gln Lys Glu Gly Thr Glu Ala Ser Leu Gln Ile Arg Gly Lys Lys Lys
            180                 185                 190

Glu Gln Arg Arg Glu Ile Gly Ser Arg Asn Ala Glu Val Arg Ala Gln
        195                 200                 205

Arg His Thr Asp Met Pro Lys Thr Gln Lys Tyr Gln Pro Pro Ser Thr
    210                 215                 220

Asn Lys Asn Thr Lys Ser Gln Arg Arg Lys Gly Trp Pro Lys Thr His
225                 230                 235                 240

Pro Gly Gly Glu Gln Lys Glu Gly Thr Glu Ala Ser Leu Gln Ile Arg
                245                 250                 255

Gly Lys Lys Lys Glu Gln Arg Arg Glu Ile Gly Ser Arg Asn Ala Glu
            260                 265                 270

Val Arg Ala Gln Arg His Thr Asp Met Pro Lys Thr Gln Lys Tyr Gln
        275                 280                 285

Pro Pro Ser Thr Asn Lys Asn Thr Lys Ser Gln Arg Arg Lys Gly Trp
    290                 295                 300

Pro Lys Thr His Pro Gly Gly Glu Gln Lys Glu Gly Thr Glu Ala Ser
305                 310                 315                 320

Leu Gln Ile Arg Gly Lys Lys Lys Glu Gln Arg Arg Glu Ile Gly Ser
                325                 330                 335

Arg Asn Ala Glu Cys Arg Gly Lys Lys Gly Lys
            340                 345
```

<210> SEQ ID NO 52
<211> LENGTH: 106
<212> TYPE: PRT
<213> ORGANISM: Homo sapiens
<220> FEATURE:
<221> NAME/KEY: PEPTIDE
<222> LOCATION: (1)...(106)
<223> OTHER INFORMATION: HIGF-1-EC:  P2, E3; R37A; R71, S72

<400> SEQUENCE: 52

```
Gly Thr Leu Cys Gly Ala Glu Leu Val Asp Ala Leu Gln Phe Val Cys
  1               5                  10                  15

Gly Asp Arg Gly Phe Tyr Phe Asn Lys Pro Thr Gly Tyr Gly Ser Ser
            20                  25                  30

Ser Arg Ala Ala Pro Gln Thr Gly Ile Val Asp Glu Cys Cys Phe Arg
        35                  40                  45

Ser Cys Asp Leu Arg Arg Leu Glu Met Tyr Cys Ala Pro Leu Lys Pro
    50                  55                  60

Ala Lys Ser Ala Val Arg Ala Gln Arg His Thr Asp Met Pro Lys Thr
65                  70                  75                  80

Gln Lys Tyr Gln Pro Pro Ser Thr Asn Lys Asn Thr Lys Ser Gln Arg
                85                  90                  95

Arg Lys Gly Ser Thr Phe Glu Glu Arg Lys
            100                 105
```

<210> SEQ ID NO 53
<211> LENGTH: 102
<212> TYPE: PRT

```
<213> ORGANISM: Homo sapiens
<220> FEATURE:
<221> NAME/KEY: PEPTIDE
<222> LOCATION: (1)...(102)
<223> OTHER INFORMATION: HIGF-1-EA:  E3; R37A; R71, S72

<400> SEQUENCE: 53

Gly Pro Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
                20                  25                  30

Ser Ser Arg Ala Ala Pro Gln Thr Gly Ile Val Asp Glu Cys Cys Phe
            35                  40                  45

Arg Ser Cys Asp Leu Arg Arg Leu Glu Met Tyr Cys Ala Pro Leu Lys
50                  55                  60

Pro Ala Lys Ser Ala Val Arg Ala Gln Arg His Thr Asp Met Pro Lys
65                  70                  75                  80

Thr Gln Lys Glu Val His Leu Lys Asn Ala Ser Arg Gly Ser Ala Gly
                85                  90                  95

Asn Lys Asn Tyr Arg Met
                100

<210> SEQ ID NO 54
<211> LENGTH: 144
<212> TYPE: PRT
<213> ORGANISM: Homo sapiens
<220> FEATURE:
<221> NAME/KEY: PEPTIDE
<222> LOCATION: (1)...(144)
<223> OTHER INFORMATION: HIGF-1-EB:  E3; R37A; R71, S72

<400> SEQUENCE: 54

Gly Pro Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
                20                  25                  30

Ser Ser Arg Ala Ala Pro Gln Thr Gly Ile Val Asp Glu Cys Cys Phe
            35                  40                  45

Arg Ser Cys Asp Leu Arg Arg Leu Glu Met Tyr Cys Ala Pro Leu Lys
50                  55                  60

Pro Ala Lys Ser Ala Val Arg Ala Gln Arg His Thr Asp Met Pro Lys
65                  70                  75                  80

Thr Gln Lys Tyr Gln Pro Pro Ser Thr Asn Lys Asn Thr Lys Ser Gln
                85                  90                  95

Arg Arg Lys Gly Trp Pro Lys Thr His Pro Gly Gly Glu Gln Lys Glu
            100                 105                 110

Gly Thr Glu Ala Ser Leu Gln Ile Arg Gly Lys Lys Lys Glu Gln Arg
        115                 120                 125

Arg Glu Ile Gly Ser Arg Asn Ala Glu Cys Arg Gly Lys Lys Gly Lys
    130                 135                 140

<210> SEQ ID NO 55
<211> LENGTH: 346
<212> TYPE: PRT
<213> ORGANISM: Homo sapiens
<220> FEATURE:
<221> NAME/KEY: PEPTIDE
<222> LOCATION: (1)...(346)
<223> OTHER INFORMATION: HIGF-1-EB MULTIMER:  (G1, P2, E3; R37A)-
    3XEB(R71, S72, C-TERM 7 AA)-EB(R71,S72)

<400> SEQUENCE: 55
```

```
Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
             20                  25                  30

Arg Ala Ala Pro Gln Thr Gly Ile Val Asp Glu Cys Cys Phe Arg Ser
         35                  40                  45

Cys Asp Leu Arg Arg Leu Glu Met Tyr Cys Ala Pro Leu Lys Pro Ala
     50                  55                  60

Lys Ser Ala Val Arg Ala Gln Arg His Thr Asp Met Pro Lys Thr Gln
 65                  70                  75                  80

Lys Tyr Gln Pro Pro Ser Thr Asn Lys Asn Thr Lys Ser Gln Arg Arg
                 85                  90                  95

Lys Gly Trp Pro Lys Thr His Pro Gly Gly Glu Gln Lys Glu Gly Thr
                100                 105                 110

Glu Ala Ser Leu Gln Ile Arg Gly Lys Lys Glu Gln Arg Arg Glu
            115                 120                 125

Ile Gly Ser Arg Asn Ala Glu Val Arg Ala Gln Arg His Thr Asp Met
        130                 135                 140

Pro Lys Thr Gln Lys Tyr Gln Pro Pro Ser Thr Asn Lys Asn Thr Lys
145                 150                 155                 160

Ser Gln Arg Arg Lys Gly Trp Pro Lys Thr His Pro Gly Gly Glu Gln
                165                 170                 175

Lys Glu Gly Thr Glu Ala Ser Leu Gln Ile Arg Gly Lys Lys Glu
            180                 185                 190

Gln Arg Arg Glu Ile Gly Ser Arg Asn Ala Glu Val Arg Ala Gln Arg
        195                 200                 205

His Thr Asp Met Pro Lys Thr Gln Lys Tyr Gln Pro Pro Ser Thr Asn
        210                 215                 220

Lys Asn Thr Lys Ser Gln Arg Arg Lys Gly Trp Pro Lys Thr His Pro
225                 230                 235                 240

Gly Gly Glu Gln Lys Glu Gly Thr Glu Ala Ser Leu Gln Ile Arg Gly
                245                 250                 255

Lys Lys Glu Gln Arg Arg Glu Ile Gly Ser Arg Asn Ala Glu Val
            260                 265                 270

Arg Ala Gln Arg His Thr Asp Met Pro Lys Thr Gln Lys Tyr Gln Pro
        275                 280                 285

Pro Ser Thr Asn Lys Asn Thr Lys Ser Gln Arg Arg Lys Gly Trp Pro
290                 295                 300

Lys Thr His Pro Gly Gly Glu Gln Lys Glu Gly Thr Glu Ala Ser Leu
305                 310                 315                 320

Gln Ile Arg Gly Lys Lys Glu Gln Arg Arg Glu Ile Gly Ser Arg
            325                 330                 335

Asn Ala Glu Cys Arg Gly Lys Lys Gly Lys
            340                 345

<210> SEQ ID NO 56
<211> LENGTH: 348
<212> TYPE: PRT
<213> ORGANISM: Homo sapiens
<220> FEATURE:
<221> NAME/KEY: PEPTIDE
<222> LOCATION: (1)...(346)
<223> OTHER INFORMATION: HIGF-1-EB MULTIMER:  (E3; R37A)-3XEB(R71, S72,
      C-TERM 7 AA)-EB(R71, S72

<400> SEQUENCE: 56
```

```
Gly Pro Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
            20                  25                  30

Ser Ser Arg Ala Ala Pro Gln Thr Gly Ile Val Asp Glu Cys Cys Phe
        35                  40                  45

Arg Ser Cys Asp Leu Arg Arg Leu Glu Met Tyr Cys Ala Pro Leu Lys
    50                  55                  60

Pro Ala Lys Ser Ala Val Arg Ala Gln Arg His Thr Asp Met Pro Lys
65                  70                  75                  80

Thr Gln Lys Tyr Gln Pro Pro Ser Thr Asn Lys Asn Thr Lys Ser Gln
                85                  90                  95

Arg Arg Lys Gly Trp Pro Lys Thr His Pro Gly Gly Glu Gln Lys Glu
            100                 105                 110

Gly Thr Glu Ala Ser Leu Gln Ile Arg Gly Lys Lys Glu Gln Arg
        115                 120                 125

Arg Glu Ile Gly Ser Arg Asn Ala Glu Val Arg Ala Gln Arg His Thr
    130                 135                 140

Asp Met Pro Lys Thr Gln Lys Tyr Gln Pro Pro Ser Thr Asn Lys Asn
145                 150                 155                 160

Thr Lys Ser Gln Arg Arg Lys Gly Trp Pro Lys Thr His Pro Gly Gly
                165                 170                 175

Glu Gln Lys Glu Gly Thr Glu Ala Ser Leu Gln Ile Arg Gly Lys Lys
            180                 185                 190

Lys Glu Gln Arg Arg Glu Ile Gly Ser Arg Asn Ala Glu Val Arg Ala
        195                 200                 205

Gln Arg His Thr Asp Met Pro Lys Thr Gln Lys Tyr Gln Pro Pro Ser
    210                 215                 220

Thr Asn Lys Asn Thr Lys Ser Gln Arg Arg Lys Gly Trp Pro Lys Thr
225                 230                 235                 240

His Pro Gly Gly Glu Gln Lys Glu Gly Thr Glu Ala Ser Leu Gln Ile
                245                 250                 255

Arg Gly Lys Lys Lys Glu Gln Arg Glu Ile Gly Ser Arg Asn Ala
            260                 265                 270

Glu Val Arg Ala Gln Arg His Thr Asp Met Pro Lys Thr Gln Lys Tyr
        275                 280                 285

Gln Pro Pro Ser Thr Asn Lys Asn Thr Lys Ser Gln Arg Arg Lys Gly
    290                 295                 300

Trp Pro Lys Thr His Pro Gly Gly Glu Gln Lys Glu Gly Thr Glu Ala
305                 310                 315                 320

Ser Leu Gln Ile Arg Gly Lys Lys Lys Glu Gln Arg Arg Glu Ile Gly
                325                 330                 335

Ser Arg Asn Ala Glu Cys Arg Gly Lys Lys Gly Lys
            340                 345

<210> SEQ ID NO 57
<211> LENGTH: 107
<212> TYPE: PRT
<213> ORGANISM: Homo sapiens
<220> FEATURE:
<221> NAME/KEY: PEPTIDE
<222> LOCATION: (1)...(107)
<223> OTHER INFORMATION: HIGF-1-EC:  E3; R37A; R71, S72

<400> SEQUENCE: 57

Gly Pro Thr Leu Cys Gly Ala Glu Leu Val Asp Ala Leu Gln Phe Val
1               5                   10                  15
```

Cys Gly Asp Arg Gly Phe Tyr Phe Asn Lys Pro Thr Gly Tyr Gly Ser
            20                  25                  30

Ser Ser Arg Ala Ala Pro Gln Thr Gly Ile Val Asp Glu Cys Cys Phe
            35                  40                  45

Arg Ser Cys Asp Leu Arg Arg Leu Glu Met Tyr Cys Ala Pro Leu Lys
            50                  55                  60

Pro Ala Lys Ser Ala Val Arg Ala Gln Arg His Thr Asp Met Pro Lys
65                  70                  75                  80

Thr Gln Lys Tyr Gln Pro Pro Ser Thr Asn Lys Asn Thr Lys Ser Gln
            85                  90                  95

Arg Arg Lys Gly Ser Thr Phe Glu Glu Arg Lys
            100                 105

<210> SEQ ID NO 58
<211> LENGTH: 102
<212> TYPE: PRT
<213> ORGANISM: Homo sapiens
<220> FEATURE:
<221> NAME/KEY: PEPTIDE
<222> LOCATION: (1)...(102)
<223> OTHER INFORMATION: HIGF-1-EA:  E3; R37A; R71, S72

<400> SEQUENCE: 58

Gly Pro Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
            20                  25                  30

Ser Ser Arg Ala Ala Pro Gln Thr Gly Ile Val Asp Glu Cys Cys Phe
            35                  40                  45

Arg Ser Cys Asp Leu Arg Arg Leu Glu Met Tyr Cys Ala Pro Leu Lys
            50                  55                  60

Pro Ala Lys Ser Ala Val Arg Ala Gln Arg His Thr Asp Met Pro Lys
65                  70                  75                  80

Thr Gln Lys Glu Val His Leu Lys Asn Ala Ser Arg Gly Ser Ala Gly
            85                  90                  95

Asn Lys Asn Tyr Arg Met
            100

<210> SEQ ID NO 59
<211> LENGTH: 144
<212> TYPE: PRT
<213> ORGANISM: Homo sapiens
<220> FEATURE:
<221> NAME/KEY: PEPTIDE
<222> LOCATION: (1)...(144)
<223> OTHER INFORMATION: HIGF-1-EB:  E3; R37A; R71, S72

<400> SEQUENCE: 59

Gly Pro Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
            20                  25                  30

Ser Ser Arg Ala Ala Pro Gln Thr Gly Ile Val Asp Glu Cys Cys Phe
            35                  40                  45

Arg Ser Cys Asp Leu Arg Arg Leu Glu Met Tyr Cys Ala Pro Leu Lys
            50                  55                  60

Pro Ala Lys Ser Ala Val Arg Ala Gln Arg His Thr Asp Met Pro Lys
65                  70                  75                  80

Thr Gln Lys Tyr Gln Pro Pro Ser Thr Asn Lys Asn Thr Lys Ser Gln

```
                    85                  90                  95

Arg Arg Lys Gly Trp Pro Lys Thr His Pro Gly Gly Glu Gln Lys Glu
            100                 105                 110

Gly Thr Glu Ala Ser Leu Gln Ile Arg Gly Lys Lys Lys Glu Gln Arg
        115                 120                 125

Arg Glu Ile Gly Ser Arg Asn Ala Glu Cys Arg Gly Lys Lys Gly Lys
    130                 135                 140

<210> SEQ ID NO 60
<211> LENGTH: 107
<212> TYPE: PRT
<213> ORGANISM: Homo sapiens
<220> FEATURE:
<221> NAME/KEY: PEPTIDE
<222> LOCATION: (1)...(107)
<223> OTHER INFORMATION: HIGF-1-EC:  E3; R37A; R71, S72

<400> SEQUENCE: 60

Gly Pro Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
            20                  25                  30

Ser Ser Arg Ala Ala Pro Gln Thr Gly Ile Val Asp Glu Cys Cys Phe
        35                  40                  45

Arg Ser Cys Asp Leu Arg Arg Leu Glu Met Tyr Cys Ala Pro Leu Lys
    50                  55                  60

Pro Ala Lys Ser Ala Val Arg Ala Gln Arg His Thr Asp Met Pro Lys
65                  70                  75                  80

Thr Gln Lys Tyr Gln Pro Pro Ser Thr Asn Lys Asn Thr Lys Ser Gln
                85                  90                  95

Arg Arg Lys Gly Ser Thr Phe Glu Glu Arg Lys
            100                 105

<210> SEQ ID NO 61
<211> LENGTH: 154
<212> TYPE: PRT
<213> ORGANISM: Homo sapiens
<220> FEATURE:
<221> NAME/KEY: PEPTIDE
<222> LOCATION: (1)...(154)
<223> OTHER INFORMATION: HIGF-1-EAB:  E3; R37A;  R71, S72

<400> SEQUENCE: 61

Gly Pro Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
            20                  25                  30

Ser Ser Arg Ala Ala Pro Gln Thr Gly Ile Val Asp Glu Cys Cys Phe
        35                  40                  45

Arg Ser Cys Asp Leu Arg Arg Leu Glu Met Tyr Cys Ala Pro Leu Lys
    50                  55                  60

Pro Ala Lys Ser Ala Val Arg Ala Gln Arg His Thr Asp Met Pro Lys
65                  70                  75                  80

Thr Gln Lys Tyr Gln Pro Pro Ser Thr Asn Lys Asn Ala Ser Arg Gly
                85                  90                  95

Ser Ala Gly Asn Lys Asn Thr Lys Ser Gln Arg Arg Lys Gly Trp Pro
            100                 105                 110

Lys Thr His Pro Gly Gly Glu Gln Lys Glu Gly Thr Glu Ala Ser Leu
        115                 120                 125
```

Gln Ile Arg Gly Lys Lys Glu Gln Arg Glu Ile Gly Ser Arg
                130             135             140

Asn Ala Glu Cys Arg Gly Lys Lys Gly Lys
145                 150

<210> SEQ ID NO 62
<211> LENGTH: 348
<212> TYPE: PRT
<213> ORGANISM: Homo sapiens
<220> FEATURE:
<221> NAME/KEY: PEPTIDE
<222> LOCATION: (1)...(0)
<223> OTHER INFORMATION: HIGF-1-EB MULTIMER: (E3; R37A)-3XEB(R71, S72,
      C-TERM 7 AA)-EB(R71, S72)

<400> SEQUENCE: 62

Gly Pro Thr Leu Cys Gly Ala Glu Leu Val Asp Ala Leu Gln Phe Val
 1               5                  10                  15

Cys Gly Asp Arg Gly Phe Tyr Phe Asn Lys Pro Thr Gly Tyr Gly Ser
                20                  25                  30

Ser Ser Arg Ala Ala Pro Gln Thr Gly Ile Val Asp Glu Cys Cys Phe
            35                  40                  45

Arg Ser Cys Asp Leu Arg Arg Leu Glu Met Tyr Cys Ala Pro Leu Lys
50                  55                  60

Pro Ala Lys Ser Ala Val Arg Ala Gln Arg His Thr Asp Met Pro Lys
65                  70                  75                  80

Thr Gln Lys Tyr Gln Pro Pro Ser Thr Asn Lys Asn Thr Lys Ser Gln
                85                  90                  95

Arg Arg Lys Gly Trp Pro Lys Thr His Pro Gly Gly Glu Gln Lys Glu
            100                 105                 110

Gly Thr Glu Ala Ser Leu Gln Ile Arg Gly Lys Lys Glu Gln Arg
        115                 120                 125

Arg Glu Ile Gly Ser Arg Asn Ala Glu Val Arg Ala Gln Arg His Thr
130                 135                 140

Asp Met Pro Lys Thr Gln Lys Tyr Gln Pro Pro Ser Thr Asn Lys Asn
145                 150                 155                 160

Thr Lys Ser Gln Arg Arg Lys Gly Trp Pro Lys Thr His Pro Gly Gly
                165                 170                 175

Glu Gln Lys Glu Gly Thr Glu Ala Ser Leu Gln Ile Arg Gly Lys Lys
            180                 185                 190

Lys Glu Gln Arg Arg Glu Ile Gly Ser Arg Asn Ala Glu Val Arg Ala
        195                 200                 205

Gln Arg His Thr Asp Met Pro Lys Thr Gln Lys Tyr Gln Pro Pro Ser
210                 215                 220

Thr Asn Lys Asn Thr Lys Ser Gln Arg Arg Lys Gly Trp Pro Lys Thr
225                 230                 235                 240

His Pro Gly Gly Glu Gln Lys Glu Gly Thr Glu Ala Ser Leu Gln Ile
                245                 250                 255

Arg Gly Lys Lys Lys Glu Gln Arg Arg Glu Ile Gly Ser Arg Asn Ala
            260                 265                 270

Glu Val Arg Ala Gln Arg His Thr Asp Met Pro Lys Thr Gln Lys Tyr
        275                 280                 285

Gln Pro Pro Ser Thr Asn Lys Asn Thr Lys Ser Gln Arg Arg Lys Gly
290                 295                 300

Trp Pro Lys Thr His Pro Gly Gly Glu Gln Lys Glu Gly Thr Glu Ala
305                 310                 315                 320

Ser Leu Gln Ile Arg Gly Lys Lys Lys Glu Gln Arg Arg Glu Ile Gly

```
                    325                 330                 335
Ser Arg Asn Ala Glu Cys Arg Gly Lys Lys Gly Lys
                340                 345
```

<210> SEQ ID NO 63
<211> LENGTH: 103
<212> TYPE: PRT
<213> ORGANISM: Homo sapiens
<220> FEATURE:
<221> NAME/KEY: PEPTIDE
<222> LOCATION: (1)...(348)
<223> OTHER INFORMATION: HIGF-1-EA:  E3A; R37A; R71, S72

<400> SEQUENCE: 63

```
Gly Pro Ala Thr Leu Cys Gly Ala Glu Leu Val Asp Ala Leu Gln Phe
 1               5                   10                  15

Val Cys Gly Asp Arg Gly Phe Tyr Phe Asn Lys Pro Thr Gly Tyr Gly
                20                  25                  30

Ser Ser Ser Arg Ala Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
 50                  55                  60

Lys Pro Ala Lys Ser Ala Val Arg Ala Gln Arg His Thr Asp Met Pro
65                  70                  75                  80

Lys Thr Gln Lys Glu Val His Leu Lys Asn Ala Ser Arg Gly Ser Ala
                85                  90                  95

Gly Asn Lys Asn Tyr Arg Met
                100
```

<210> SEQ ID NO 64
<211> LENGTH: 145
<212> TYPE: PRT
<213> ORGANISM: Homo sapiens
<220> FEATURE:
<221> NAME/KEY: PEPTIDE
<222> LOCATION: (1)...(145)
<223> OTHER INFORMATION: HIGF-1-EB:  E3A; R37A; R71, S72

<400> SEQUENCE: 64

```
Gly Pro Ala Thr Leu Cys Gly Ala Glu Leu Val Asp Ala Leu Gln Phe
 1               5                   10                  15

Val Cys Gly Asp Arg Gly Phe Tyr Phe Asn Lys Pro Thr Gly Tyr Gly
                20                  25                  30

Ser Ser Ser Arg Ala Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
 50                  55                  60

Lys Pro Ala Lys Ser Ala Val Arg Ala Gln Arg His Thr Asp Met Pro
65                  70                  75                  80

Lys Thr Gln Lys Tyr Gln Pro Pro Ser Thr Asn Lys Asn Thr Lys Ser
                85                  90                  95

Gln Arg Arg Lys Gly Trp Pro Lys Thr His Pro Gly Gly Glu Gln Lys
                100                 105                 110

Glu Gly Thr Glu Ala Ser Leu Gln Ile Arg Gly Lys Lys Lys Glu Gln
        115                 120                 125

Arg Arg Glu Ile Gly Ser Arg Asn Ala Glu Cys Arg Gly Lys Lys Gly
    130                 135                 140

Lys
145
```

```
<210> SEQ ID NO 65
<211> LENGTH: 108
<212> TYPE: PRT
<213> ORGANISM: Homo sapiens
<220> FEATURE:
<221> NAME/KEY: PEPTIDE
<222> LOCATION: (1)...(108)
<223> OTHER INFORMATION: HIGF-1-EC:  E3A; R37A; R71, S72

<400> SEQUENCE: 65

Gly Pro Ala Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Ala Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala Val Arg Ala Gln Arg His Thr Asp Met Pro
65                  70                  75                  80

Lys Thr Gln Lys Tyr Gln Pro Pro Ser Thr Asn Lys Asn Thr Lys Ser
                85                  90                  95

Gln Arg Arg Lys Gly Ser Thr Phe Glu Glu Arg Lys
                100                 105

<210> SEQ ID NO 66
<211> LENGTH: 155
<212> TYPE: PRT
<213> ORGANISM: Homo sapiens
<220> FEATURE:
<221> NAME/KEY: PEPTIDE
<222> LOCATION: (1)...(155)
<223> OTHER INFORMATION: HIGF-1-EAB:  E3A; R37A; R71, S72

<400> SEQUENCE: 66

Gly Pro Ala Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Ala Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala Val Arg Ala Gln Arg His Thr Asp Met Pro
65                  70                  75                  80

Lys Thr Gln Lys Tyr Gln Pro Pro Ser Thr Asn Lys Asn Ala Ser Arg
                85                  90                  95

Gly Ser Ala Gly Asn Lys Asn Thr Lys Ser Gln Arg Arg Lys Gly Trp
                100                 105                 110

Pro Lys Thr His Pro Gly Gly Glu Gln Lys Glu Gly Thr Glu Ala Ser
            115                 120                 125

Leu Gln Ile Arg Gly Lys Lys Glu Gln Arg Glu Ile Gly Ser
    130                 135                 140

Arg Asn Ala Glu Cys Arg Gly Lys Lys Gly Lys
145                 150                 155

<210> SEQ ID NO 67
<211> LENGTH: 348
<212> TYPE: PRT
<213> ORGANISM: Homo sapiens
```

```
<220> FEATURE:
<221> NAME/KEY: PEPTIDE
<222> LOCATION: (1)...(348)
<223> OTHER INFORMATION: HIGF-1-EB MULTIMER: (E3A; R37A)-3XEB(R71, S72,
      C-TERM 7 AA)-EB(R71, S72

<400> SEQUENCE: 67
```

| | | | | | | | | | | | | | | |
|---|---|---|---|---|---|---|---|---|---|---|---|---|---|---|
| Gly | Pro | Ala | Thr | Leu | Cys | Gly | Ala | Glu | Leu | Val | Asp | Ala | Leu | Gln | Phe |
| 1 | | | | 5 | | | | | 10 | | | | | 15 | |
| Val | Cys | Gly | Asp | Arg | Gly | Phe | Tyr | Phe | Asn | Lys | Pro | Thr | Gly | Tyr | Gly |
| | | | 20 | | | | | 25 | | | | | 30 | | |
| Ser | Ser | Ser | Arg | Ala | Ala | Pro | Gln | Thr | Gly | Ile | Val | Asp | Glu | Cys | Cys |
| | | 35 | | | | | 40 | | | | | 45 | | | |
| Phe | Arg | Ser | Cys | Asp | Leu | Arg | Arg | Leu | Glu | Met | Tyr | Cys | Ala | Pro | Leu |
| 50 | | | | | 55 | | | | | 60 | | | | | |
| Lys | Pro | Ala | Lys | Ser | Ala | Val | Arg | Ala | Gln | Arg | His | Thr | Asp | Met | Pro |
| 65 | | | | | 70 | | | | | 75 | | | | | 80 |
| Lys | Thr | Gln | Lys | Tyr | Gln | Pro | Pro | Ser | Thr | Asn | Lys | Asn | Thr | Lys | Ser |
| | | | | 85 | | | | | 90 | | | | | 95 | |
| Gln | Arg | Arg | Lys | Gly | Trp | Pro | Lys | Thr | His | Pro | Gly | Gly | Glu | Gln | Lys |
| | | | 100 | | | | | 105 | | | | | 110 | | |
| Glu | Gly | Thr | Glu | Ala | Ser | Leu | Gln | Ile | Arg | Gly | Lys | Lys | Lys | Glu | Gln |
| | | | 115 | | | | | 120 | | | | | 125 | | |
| Arg | Arg | Glu | Ile | Gly | Ser | Arg | Asn | Ala | Glu | Val | Arg | Ala | Gln | Arg | His |
| | 130 | | | | | 135 | | | | | 140 | | | | |
| Thr | Asp | Met | Pro | Lys | Thr | Gln | Lys | Tyr | Gln | Pro | Pro | Ser | Thr | Asn | Lys |
| 145 | | | | | 150 | | | | | 155 | | | | | 160 |
| Asn | Thr | Lys | Ser | Gln | Arg | Arg | Lys | Gly | Trp | Pro | Lys | Thr | His | Pro | Gly |
| | | | 165 | | | | | 170 | | | | | 175 | | |
| Gly | Glu | Gln | Lys | Glu | Gly | Thr | Glu | Ala | Ser | Leu | Gln | Ile | Arg | Gly | Lys |
| | | | 180 | | | | | 185 | | | | | 190 | | |
| Lys | Lys | Glu | Gln | Arg | Arg | Glu | Ile | Gly | Ser | Arg | Asn | Ala | Glu | Val | Arg |
| | | 195 | | | | | 200 | | | | | 205 | | | |
| Ala | Gln | Arg | His | Thr | Asp | Met | Pro | Lys | Thr | Gln | Lys | Tyr | Gln | Pro | Pro |
| 210 | | | | | 215 | | | | | 220 | | | | | |
| Ser | Thr | Asn | Lys | Asn | Thr | Lys | Ser | Gln | Arg | Arg | Lys | Gly | Trp | Pro | Lys |
| 225 | | | | | 230 | | | | | 235 | | | | | 240 |
| Thr | His | Pro | Gly | Gly | Glu | Gln | Lys | Glu | Gly | Thr | Glu | Ala | Ser | Leu | Gln |
| | | | | 245 | | | | | 250 | | | | | 255 | |
| Ile | Arg | Gly | Lys | Lys | Lys | Glu | Gln | Arg | Arg | Glu | Ile | Gly | Ser | Arg | Asn |
| | | | 260 | | | | | 265 | | | | | 270 | | |
| Ala | Glu | Val | Arg | Ala | Gln | Arg | His | Thr | Asp | Met | Pro | Lys | Thr | Gln | Lys |
| | | 275 | | | | | 280 | | | | | 285 | | | |
| Tyr | Gln | Pro | Pro | Ser | Thr | Asn | Lys | Asn | Thr | Lys | Ser | Gln | Arg | Arg | Lys |
| | 290 | | | | | 295 | | | | | 300 | | | | |
| Gly | Trp | Pro | Lys | Thr | His | Pro | Gly | Gly | Glu | Gln | Lys | Glu | Gly | Thr | Glu |
| 305 | | | | | 310 | | | | | 315 | | | | | 320 |
| Ala | Ser | Leu | Gln | Ile | Arg | Gly | Lys | Lys | Lys | Glu | Gln | Arg | Arg | Glu | Ile |
| | | | | 325 | | | | | 330 | | | | | 335 | |
| Gly | Ser | Arg | Asn | Ala | Glu | Cys | Arg | Gly | Lys | Lys | Gly | | | | |
| | | | 340 | | | | | 345 | | | | | | | |

```
<210> SEQ ID NO 68
<211> LENGTH: 101
<212> TYPE: PRT
<213> ORGANISM: Homo sapiens
<220> FEATURE:
```

```
<221> NAME/KEY: PEPTIDE
<222> LOCATION: (1)...(101)
<223> OTHER INFORMATION: HIGF-1-EA: P2, E3; R37A; R71, S72

<400> SEQUENCE: 68
```

Gly Thr Leu Cys Gly Ala Glu Leu Val Asp Ala Leu Gln Phe Val Cys
1               5                   10                  15

Gly Asp Arg Gly Phe Tyr Phe Asn Lys Pro Thr Gly Tyr Gly Ser Ser
            20                  25                  30

Ser Arg Ala Ala Pro Gln Thr Gly Ile Val Asp Glu Cys Cys Phe Arg
        35                  40                  45

Ser Cys Asp Leu Arg Arg Leu Glu Met Tyr Cys Ala Pro Leu Lys Pro
    50                  55                  60

Ala Lys Ser Ala Val Arg Ala Gln Arg His Thr Asp Met Pro Lys Thr
65                  70                  75                  80

Gln Lys Glu Val His Leu Lys Asn Ala Ser Arg Gly Ser Ala Gly Asn
                85                  90                  95

Lys Asn Tyr Arg Met
            100

```
<210> SEQ ID NO 69
<211> LENGTH: 143
<212> TYPE: PRT
<213> ORGANISM: Homo sapiens
<220> FEATURE:
<221> NAME/KEY: PEPTIDE
<222> LOCATION: (1)...(143)
<223> OTHER INFORMATION: HIGF-1-EB: P2, E3; R37A; R71, S72

<400> SEQUENCE: 69
```

Gly Thr Leu Cys Gly Ala Glu Leu Val Asp Ala Leu Gln Phe Val Cys
1               5                   10                  15

Gly Asp Arg Gly Phe Tyr Phe Asn Lys Pro Thr Gly Tyr Gly Ser Ser
            20                  25                  30

Ser Arg Ala Ala Pro Gln Thr Gly Ile Val Asp Glu Cys Cys Phe Arg
        35                  40                  45

Ser Cys Asp Leu Arg Arg Leu Glu Met Tyr Cys Ala Pro Leu Lys Pro
    50                  55                  60

Ala Lys Ser Ala Val Arg Ala Gln Arg His Thr Asp Met Pro Lys Thr
65                  70                  75                  80

Gln Lys Tyr Gln Pro Pro Ser Thr Asn Lys Asn Thr Lys Ser Gln Arg
                85                  90                  95

Arg Lys Gly Trp Pro Lys Thr His Pro Gly Gly Glu Gln Lys Glu Gly
            100                 105                 110

Thr Glu Ala Ser Leu Gln Ile Arg Gly Lys Lys Lys Glu Gln Arg Arg
            115                 120                 125

Glu Ile Gly Ser Arg Asn Ala Glu Cys Arg Gly Lys Lys Gly Lys
            130                 135                 140

```
<210> SEQ ID NO 70
<211> LENGTH: 153
<212> TYPE: PRT
<213> ORGANISM: Homo sapiens
<220> FEATURE:
<221> NAME/KEY: PEPTIDE
<222> LOCATION: (1)...(153)
<223> OTHER INFORMATION: HIGF-1-EAB: P2, E3; R37A; R71, S72

<400> SEQUENCE: 70
```

Gly Thr Leu Cys Gly Ala Glu Leu Val Asp Ala Leu Gln Phe Val Cys
1               5                   10                  15

```
Gly Asp Arg Gly Phe Tyr Phe Asn Lys Pro Thr Gly Tyr Gly Ser Ser
            20                  25                  30

Ser Arg Ala Ala Pro Gln Thr Gly Ile Val Asp Glu Cys Cys Phe Arg
        35                  40                  45

Ser Cys Asp Leu Arg Arg Leu Glu Met Tyr Cys Ala Pro Leu Lys Pro
    50                  55                  60

Ala Lys Ser Ala Val Arg Ala Gln Arg His Thr Asp Met Pro Lys Thr
65                  70                  75                  80

Gln Lys Tyr Gln Pro Pro Ser Thr Asn Lys Asn Ala Ser Arg Gly Ser
                85                  90                  95

Ala Gly Asn Lys Asn Thr Lys Ser Gln Arg Arg Lys Gly Trp Pro Lys
            100                 105                 110

Thr His Pro Gly Gly Glu Gln Lys Glu Gly Thr Glu Ala Ser Leu Gln
            115                 120                 125

Ile Arg Gly Lys Lys Lys Glu Gln Arg Glu Ile Gly Ser Arg Asn
    130                 135                 140

Ala Glu Cys Arg Gly Lys Lys Gly Lys
145                 150
```

```
<210> SEQ ID NO 71
<211> LENGTH: 347
<212> TYPE: PRT
<213> ORGANISM: Homo sapiens
<220> FEATURE:
<221> NAME/KEY: PEPTIDE
<222> LOCATION: (1)...(347)
<223> OTHER INFORMATION: HIGF-1-EB MULTIMER: (P2, E3; R37A)-3XEB(R71,
      S72, C-TERM 7 AA)-EB(R71, S72)

<400> SEQUENCE: 71

Gly Thr Leu Cys Gly Ala Glu Leu Val Asp Ala Leu Gln Phe Val Cys
1               5                   10                  15

Gly Asp Arg Gly Phe Tyr Phe Asn Lys Pro Thr Gly Tyr Gly Ser Ser
            20                  25                  30

Ser Arg Ala Ala Pro Gln Thr Gly Ile Val Asp Glu Cys Cys Phe Arg
        35                  40                  45

Ser Cys Asp Leu Arg Arg Leu Glu Met Tyr Cys Ala Pro Leu Lys Pro
    50                  55                  60

Ala Lys Ser Ala Val Arg Ala Gln Arg His Thr Asp Met Pro Lys Thr
65                  70                  75                  80

Gln Lys Tyr Gln Pro Pro Ser Thr Asn Lys Asn Thr Lys Ser Gln Arg
                85                  90                  95

Arg Lys Gly Trp Pro Lys Thr His Pro Gly Gly Glu Gln Lys Glu Gly
            100                 105                 110

Thr Glu Ala Ser Leu Gln Ile Arg Gly Lys Lys Lys Glu Gln Arg Arg
            115                 120                 125

Glu Ile Gly Ser Arg Asn Ala Glu Val Arg Ala Gln Arg His Thr Asp
            130                 135                 140

Met Pro Lys Thr Gln Lys Tyr Gln Pro Pro Ser Thr Asn Lys Asn Thr
145                 150                 155                 160

Lys Ser Gln Arg Arg Lys Gly Trp Pro Lys Thr His Pro Gly Gly Glu
                165                 170                 175

Gln Lys Glu Gly Thr Glu Ala Ser Leu Gln Ile Arg Gly Lys Lys Lys
            180                 185                 190

Glu Gln Arg Arg Glu Ile Gly Ser Arg Asn Ala Glu Val Arg Ala Gln
            195                 200                 205
```

```
Arg His Thr Asp Met Pro Lys Thr Gln Lys Tyr Gln Pro Pro Ser Thr
    210                 215                 220

Asn Lys Asn Thr Lys Ser Gln Arg Arg Lys Gly Trp Pro Lys Thr His
225                 230                 235                 240

Pro Gly Gly Glu Gln Lys Glu Gly Thr Glu Ala Ser Leu Gln Ile Arg
                245                 250                 255

Gly Lys Lys Lys Glu Gln Arg Arg Glu Ile Gly Ser Arg Asn Ala Glu
                260                 265                 270

Val Arg Ala Gln Arg His Thr Asp Met Pro Lys Thr Gln Lys Tyr Gln
                275                 280                 285

Pro Pro Ser Thr Asn Lys Asn Thr Lys Ser Gln Arg Arg Lys Gly Trp
                290                 295                 300

Pro Lys Thr His Pro Gly Gly Glu Gln Lys Glu Gly Thr Glu Ala Ser
305                 310                 315                 320

Leu Gln Ile Arg Gly Lys Lys Lys Glu Gln Arg Arg Glu Ile Gly Ser
                325                 330                 335

Arg Asn Ala Glu Cys Arg Gly Lys Lys Gly Lys
                340                 345
```

```
<210> SEQ ID NO 72
<211> LENGTH: 143
<212> TYPE: PRT
<213> ORGANISM: Homo sapiens
<220> FEATURE:
<221> NAME/KEY: PEPTIDE
<222> LOCATION: (1)...(143)
<221> NAME/KEY: VARIANT
<222> LOCATION: 1
<223> OTHER INFORMATION: Xaa is non-natural amino acid that is
      pegylated

<400> SEQUENCE: 72
```

```
Xaa Thr Leu Cys Gly Ala Glu Leu Val Asp Ala Leu Gln Phe Val Cys
1               5                   10                  15

Gly Asp Arg Gly Phe Tyr Phe Asn Lys Pro Thr Gly Tyr Gly Ser Ser
                20                  25                  30

Ser Arg Ala Ala Pro Gln Thr Gly Ile Val Asp Glu Cys Cys Phe Arg
                35                  40                  45

Ser Cys Asp Leu Arg Arg Leu Glu Met Tyr Cys Ala Pro Leu Lys Pro
50                  55                  60

Ala Lys Ser Ala Val Arg Ala Gln Arg His Thr Asp Met Pro Lys Thr
65                  70                  75                  80

Gln Lys Tyr Gln Pro Pro Ser Thr Asn Lys Asn Thr Lys Ser Gln Arg
                85                  90                  95

Arg Lys Gly Trp Pro Lys Thr His Pro Gly Gly Glu Gln Lys Glu Gly
                100                 105                 110

Thr Glu Ala Ser Leu Gln Ile Arg Gly Lys Lys Lys Glu Gln Arg Arg
                115                 120                 125

Glu Ile Gly Ser Arg Asn Ala Glu Cys Arg Gly Lys Lys Gly Lys
                130                 135                 140
```

```
<210> SEQ ID NO 73
<211> LENGTH: 106
<212> TYPE: PRT
<213> ORGANISM: Homo sapiens
<220> FEATURE:
<221> NAME/KEY: PEPTIDE
<222> LOCATION: (1)...(106)
<221> NAME/KEY: VARIANT
<222> LOCATION: 1
<223> OTHER INFORMATION: Xaa is non-naturaly amino acid that is
```

-continued pegylated.

<400> SEQUENCE: 73

Xaa Thr Leu Cys Gly Ala Glu Leu Val Asp Ala Leu Gln Phe Val Cys
1               5                   10                  15

Gly Asp Arg Gly Phe Tyr Phe Asn Lys Pro Thr Gly Tyr Gly Ser Ser
            20                  25                  30

Ser Arg Ala Ala Pro Gln Thr Gly Ile Val Asp Glu Cys Cys Phe Arg
        35                  40                  45

Ser Cys Asp Leu Arg Arg Leu Glu Met Tyr Cys Ala Pro Leu Lys Pro
    50                  55                  60

Ala Lys Ser Ala Val Arg Ala Gln Arg His Thr Asp Met Pro Lys Thr
65                  70                  75                  80

Gln Lys Tyr Gln Pro Pro Ser Thr Asn Lys Asn Thr Lys Ser Gln Arg
                85                  90                  95

Arg Lys Gly Ser Thr Phe Glu Glu Arg Lys
            100                 105

<210> SEQ ID NO 74
<211> LENGTH: 153
<212> TYPE: PRT
<213> ORGANISM: Homo sapiens
<220> FEATURE:
<221> NAME/KEY: PEPTIDE
<222> LOCATION: (1)...(153)
<221> NAME/KEY: VARIANT
<222> LOCATION: 1
<223> OTHER INFORMATION: Xaa is non-natural amino acid that is
      pegylated.

<400> SEQUENCE: 74

Xaa Thr Leu Cys Gly Ala Glu Leu Val Asp Ala Leu Gln Phe Val Cys
1               5                   10                  15

Gly Asp Arg Gly Phe Tyr Phe Asn Lys Pro Thr Gly Tyr Gly Ser Ser
            20                  25                  30

Ser Arg Ala Ala Pro Gln Thr Gly Ile Val Asp Glu Cys Cys Phe Arg
        35                  40                  45

Ser Cys Asp Leu Arg Arg Leu Glu Met Tyr Cys Ala Pro Leu Lys Pro
    50                  55                  60

Ala Lys Ser Ala Val Arg Ala Gln Arg His Thr Asp Met Pro Lys Thr
65                  70                  75                  80

Gln Lys Tyr Gln Pro Pro Ser Thr Asn Lys Asn Ala Ser Arg Gly Ser
                85                  90                  95

Ala Gly Asn Lys Asn Thr Lys Ser Gln Arg Arg Lys Gly Trp Pro Lys
            100                 105                 110

Thr His Pro Gly Gly Glu Gln Lys Glu Gly Thr Glu Ala Ser Leu Gln
            115                 120                 125

Ile Arg Gly Lys Lys Lys Glu Gln Arg Arg Glu Ile Gly Ser Arg Asn
        130                 135                 140

Ala Glu Cys Arg Gly Lys Lys Gly Lys
145                 150

<210> SEQ ID NO 75
<211> LENGTH: 347
<212> TYPE: PRT
<213> ORGANISM: Homo sapiens
<220> FEATURE:
<221> NAME/KEY: PEPTIDE
<222> LOCATION: (1)...(347)
<221> NAME/KEY: VARIANT
<222> LOCATION: 1

<223> OTHER INFORMATION: Xaa is non-natural amino acid that is
      pegylated.

<400> SEQUENCE: 75

Xaa Thr Leu Cys Gly Ala Glu Leu Val Asp Ala Leu Gln Phe Val Cys
1               5                   10                  15

Gly Asp Arg Gly Phe Tyr Phe Asn Lys Pro Thr Gly Tyr Gly Ser Ser
            20                  25                  30

Ser Arg Ala Ala Pro Gln Thr Gly Ile Val Asp Glu Cys Cys Phe Arg
        35                  40                  45

Ser Cys Asp Leu Arg Arg Leu Glu Met Tyr Cys Ala Pro Leu Lys Pro
    50                  55                  60

Ala Lys Ser Ala Val Arg Ala Gln Arg His Thr Asp Met Pro Lys Thr
65                  70                  75                  80

Gln Lys Tyr Gln Pro Pro Ser Thr Asn Lys Asn Thr Lys Ser Gln Arg
                85                  90                  95

Arg Lys Gly Trp Pro Lys Thr His Pro Gly Gly Glu Gln Lys Glu Gly
            100                 105                 110

Thr Glu Ala Ser Leu Gln Ile Arg Gly Lys Lys Lys Glu Gln Arg Arg
        115                 120                 125

Glu Ile Gly Ser Arg Asn Ala Glu Val Arg Ala Gln Arg His Thr Asp
    130                 135                 140

Met Pro Lys Thr Gln Lys Tyr Gln Pro Pro Ser Thr Asn Lys Asn Thr
145                 150                 155                 160

Lys Ser Gln Arg Arg Lys Gly Trp Pro Lys Thr His Pro Gly Gly Glu
                165                 170                 175

Gln Lys Glu Gly Thr Glu Ala Ser Leu Gln Ile Arg Gly Lys Lys Lys
            180                 185                 190

Glu Gln Arg Arg Glu Ile Gly Ser Arg Asn Ala Glu Val Arg Ala Gln
        195                 200                 205

Arg His Thr Asp Met Pro Lys Thr Gln Lys Tyr Gln Pro Pro Ser Thr
    210                 215                 220

Asn Lys Asn Thr Lys Ser Gln Arg Arg Lys Gly Trp Pro Lys Thr His
225                 230                 235                 240

Pro Gly Gly Glu Gln Lys Glu Gly Thr Glu Ala Ser Leu Gln Ile Arg
                245                 250                 255

Gly Lys Lys Lys Glu Gln Arg Arg Glu Ile Gly Ser Arg Asn Ala Glu
            260                 265                 270

Val Arg Ala Gln Arg His Thr Asp Met Pro Lys Thr Gln Lys Tyr Gln
        275                 280                 285

Pro Pro Ser Thr Asn Lys Asn Thr Lys Ser Gln Arg Arg Lys Gly Trp
    290                 295                 300

Pro Lys Thr His Pro Gly Gly Glu Gln Lys Glu Gly Thr Glu Ala Ser
305                 310                 315                 320

Leu Gln Ile Arg Gly Lys Lys Lys Glu Gln Arg Arg Glu Ile Gly Ser
                325                 330                 335

Arg Asn Ala Glu Cys Arg Gly Lys Lys Gly Lys
            340                 345

<210> SEQ ID NO 76
<211> LENGTH: 101
<212> TYPE: PRT
<213> ORGANISM: Homo sapiens
<220> FEATURE:
<221> NAME/KEY: PEPTIDE
<222> LOCATION: (1)...(101)
<221> NAME/KEY: VARIANT

```
<222> LOCATION: 68
<223> OTHER INFORMATION: Xaa is non-natural amino acid that is pegylated

<400> SEQUENCE: 76

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala Xaa Val Arg Ala Gln Arg His Thr Asp Met Pro Lys Thr
 65                  70                  75                  80

Gln Lys Glu Val His Leu Lys Asn Ala Ser Arg Gly Ser Ala Gly Asn
                 85                  90                  95

Lys Asn Tyr Arg Met
            100

<210> SEQ ID NO 77
<211> LENGTH: 143
<212> TYPE: PRT
<213> ORGANISM: Homo sapiens
<220> FEATURE:
<221> NAME/KEY: PEPTIDE
<222> LOCATION: (1)...(143)
<221> NAME/KEY: VARIANT
<222> LOCATION: 68
<223> OTHER INFORMATION: Xaa is non-natural amino acid that is pegylated

<400> SEQUENCE: 77

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
 50                  55                  60

Lys Ser Ala Xaa Val Arg Ala Gln Arg His Thr Asp Met Pro Lys Thr
 65                  70                  75                  80

Gln Lys Tyr Gln Pro Pro Ser Thr Asn Lys Asn Thr Lys Ser Gln Arg
                 85                  90                  95

Arg Lys Gly Trp Pro Lys Thr His Pro Gly Gly Glu Gln Lys Glu Gly
            100                 105                 110

Thr Glu Ala Ser Leu Gln Ile Arg Gly Lys Lys Gly Gln Arg Arg
        115                 120                 125

Glu Ile Gly Ser Arg Asn Ala Glu Cys Arg Gly Lys Lys Gly Lys
    130                 135                 140

<210> SEQ ID NO 78
<211> LENGTH: 106
<212> TYPE: PRT
<213> ORGANISM: Homo sapiens
<220> FEATURE:
<221> NAME/KEY: PEPTIDE
<222> LOCATION: (1)...(106)
<221> NAME/KEY: VARIANT
<222> LOCATION: 68
<223> OTHER INFORMATION: Xaa is non-natural amino acid that is
      pegylated.
```

-continued

```
<400> SEQUENCE: 78

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
50                  55                  60

Lys Ser Ala Xaa Val Arg Ala Gln Arg His Thr Asp Met Pro Lys Thr
65                  70                  75                  80

Gln Lys Tyr Gln Pro Pro Ser Thr Asn Lys Asn Thr Lys Ser Gln Arg
            85                  90                  95

Arg Lys Gly Ser Thr Phe Glu Glu Arg Lys
            100                 105

<210> SEQ ID NO 79
<211> LENGTH: 153
<212> TYPE: PRT
<213> ORGANISM: Homo sapiens
<220> FEATURE:
<221> NAME/KEY: PEPTIDE
<222> LOCATION: (1)...(153)
<221> NAME/KEY: VARIANT
<222> LOCATION: 68
<223> OTHER INFORMATION: Xaa is non-natural amino acid that is pegylated

<400> SEQUENCE: 79

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
50                  55                  60

Lys Ser Ala Xaa Val Arg Ala Gln Arg His Thr Asp Met Pro Lys Thr
65                  70                  75                  80

Gln Lys Tyr Gln Pro Pro Ser Thr Asn Lys Asn Ala Ser Arg Gly Ser
            85                  90                  95

Ala Gly Asn Lys Asn Thr Lys Ser Gln Arg Arg Lys Gly Trp Pro Lys
            100                 105                 110

Thr His Pro Gly Gly Glu Gln Lys Glu Gly Thr Glu Ala Ser Leu Gln
        115                 120                 125

Ile Arg Gly Lys Lys Glu Gln Arg Glu Ile Gly Ser Arg Asn
    130                 135                 140

Ala Glu Cys Arg Gly Lys Lys Gly Lys
145                 150

<210> SEQ ID NO 80
<211> LENGTH: 347
<212> TYPE: PRT
<213> ORGANISM: Homo sapiens
<220> FEATURE:
<221> NAME/KEY: PEPTIDE
<222> LOCATION: (1)...(347)
<223> OTHER INFORMATION: HIGF-1-EB MULTIMER: (G1, P2, E3; R37A)-EB(R71;
      S72X; C-TERM 7 AA)-2XEB(R71, Xaa is non-natural
      amino acid that is pegylated.
<221> NAME/KEY: VARIANT
<222> LOCATION: 66
```

<223> OTHER INFORMATION: Xaa is a non-naturaly amino acid pegylated

<400> SEQUENCE: 80

```
Thr Leu Cys Gly Ala Glu Leu Val Asp Ala Leu Gln Phe Val Cys Gly
1               5                   10                  15
Asp Arg Gly Phe Tyr Phe Asn Lys Pro Thr Gly Tyr Gly Ser Ser Ser
            20                  25                  30
Arg Ala Ala Pro Gln Thr Gly Ile Val Asp Glu Cys Cys Phe Arg Ser
        35                  40                  45
Cys Asp Leu Arg Arg Leu Glu Met Tyr Cys Ala Pro Leu Lys Pro Ala
50                  55                  60
Lys Xaa Ser Ala Val Arg Ala Gln Arg His Thr Asp Met Pro Lys Thr
65                  70                  75                  80
Gln Lys Tyr Gln Pro Pro Ser Thr Asn Lys Asn Thr Lys Ser Gln Arg
                85                  90                  95
Arg Lys Gly Trp Pro Lys Thr His Pro Gly Gly Glu Gln Lys Glu Gly
            100                 105                 110
Thr Glu Ala Ser Leu Gln Ile Arg Gly Lys Lys Glu Gln Arg Arg
        115                 120                 125
Glu Ile Gly Ser Arg Asn Ala Glu Val Arg Ala Gln Arg His Thr Asp
130                 135                 140
Met Pro Lys Thr Gln Lys Tyr Gln Pro Pro Ser Thr Asn Lys Asn Thr
145                 150                 155                 160
Lys Ser Gln Arg Arg Lys Gly Trp Pro Lys Thr His Pro Gly Gly Glu
                165                 170                 175
Gln Lys Glu Gly Thr Glu Ala Ser Leu Gln Ile Arg Gly Lys Lys
            180                 185                 190
Glu Gln Arg Arg Glu Ile Gly Ser Arg Asn Ala Glu Val Arg Ala Gln
        195                 200                 205
Arg His Thr Asp Met Pro Lys Thr Gln Lys Tyr Gln Pro Pro Ser Thr
210                 215                 220
Asn Lys Asn Thr Lys Ser Gln Arg Arg Lys Gly Trp Pro Lys Thr His
225                 230                 235                 240
Pro Gly Gly Glu Gln Lys Glu Gly Thr Glu Ala Ser Leu Gln Ile Arg
                245                 250                 255
Gly Lys Lys Lys Glu Gln Arg Arg Glu Ile Gly Ser Arg Asn Ala Glu
            260                 265                 270
Val Arg Ala Gln Arg His Thr Asp Met Pro Lys Thr Gln Lys Tyr Gln
        275                 280                 285
Pro Pro Ser Thr Asn Lys Asn Thr Lys Ser Gln Arg Arg Lys Gly Trp
290                 295                 300
Pro Lys Thr His Pro Gly Gly Glu Gln Lys Glu Gly Thr Glu Ala Ser
305                 310                 315                 320
Leu Gln Ile Arg Gly Lys Lys Glu Gln Arg Arg Glu Ile Gly Ser
                325                 330                 335
Arg Asn Ala Glu Cys Arg Gly Lys Lys Gly Lys
            340                 345
```

<210> SEQ ID NO 81
<211> LENGTH: 100
<212> TYPE: PRT
<213> ORGANISM: Homo sapiens
<220> FEATURE:
<221> NAME/KEY: PEPTIDE
<222> LOCATION: (1)...(100)
<221> NAME/KEY: VARIANT
<222> LOCATION: 87

<223> OTHER INFORMATION: Xaa is non-natural amino acid that is pegylated

<400> SEQUENCE: 81

```
Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Arg Ala Gln Arg His Thr Asp Met Pro Lys Thr Gln
65                  70                  75                  80

Lys Glu Val His Leu Lys Xaa Ala Ser Arg Gly Ser Ala Gly Asn Lys
                85                  90                  95

Asn Tyr Arg Met
            100
```

<210> SEQ ID NO 82
<211> LENGTH: 142
<212> TYPE: PRT
<213> ORGANISM: Homo sapiens
<220> FEATURE:
<221> NAME/KEY: PEPTIDE
<222> LOCATION: (1)...(142)
<221> NAME/KEY: VARIANT
<222> LOCATION: 136
<223> OTHER INFORMATION: Xaa is non-natural amino acid that is pegylated.

<400> SEQUENCE: 82

```
Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Arg Ala Gln Arg His Thr Asp Met Pro Lys Thr Gln
65                  70                  75                  80

Lys Tyr Gln Pro Pro Ser Thr Asn Lys Asn Thr Lys Ser Gln Arg Arg
                85                  90                  95

Lys Gly Trp Pro Lys Thr His Pro Gly Gly Glu Gln Lys Glu Gly Thr
            100                 105                 110

Glu Ala Ser Leu Gln Ile Arg Gly Lys Lys Glu Gln Arg Arg Glu
        115                 120                 125

Ile Gly Ser Arg Asn Ala Glu Xaa Arg Gly Lys Lys Gly Lys
    130                 135                 140
```

<210> SEQ ID NO 83
<211> LENGTH: 152
<212> TYPE: PRT
<213> ORGANISM: Homo sapiens
<220> FEATURE:
<221> NAME/KEY: PEPTIDE
<222> LOCATION: (1)...(152)
<221> NAME/KEY: VARIANT
<222> LOCATION: 146
<223> OTHER INFORMATION: Xaa is non natural amino acid that is pegylated.

-continued

<400> SEQUENCE: 83

```
Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
             20                  25                  30

Arg Ala Ala Pro Gln Thr Gly Ile Val Asp Glu Cys Cys Phe Arg Ser
         35                  40                  45

Cys Asp Leu Arg Arg Leu Glu Met Tyr Cys Ala Pro Leu Lys Pro Ala
 50                  55                  60

Lys Ser Ala Val Arg Ala Gln Arg His Thr Asp Met Pro Lys Thr Gln
 65                  70                  75                  80

Lys Tyr Gln Pro Pro Ser Thr Asn Lys Asn Ala Ser Arg Gly Ser Ala
             85                  90                  95

Gly Asn Lys Asn Thr Lys Ser Gln Arg Arg Lys Gly Trp Pro Lys Thr
            100                 105                 110

His Pro Gly Gly Glu Gln Lys Glu Gly Thr Glu Ala Ser Leu Gln Ile
        115                 120                 125

Arg Gly Lys Lys Lys Glu Gln Arg Arg Glu Ile Gly Ser Arg Asn Ala
    130                 135                 140

Glu Xaa Arg Gly Lys Lys Gly Lys
145                 150
```

<210> SEQ ID NO 84
<211> LENGTH: 346
<212> TYPE: PRT
<213> ORGANISM: Homo sapiens
<220> FEATURE:
<221> NAME/KEY: PEPTIDE
<222> LOCATION: (1)...(346)
<223> OTHER INFORMATION: HIGF-1-EB MULTIMER (G1, P2, E3; R37A)-3XEB(R71, S72, Xaa is non-natural amino acid that is pegylated.
<221> NAME/KEY: VARIANT
<222> LOCATION: 340
<223> OTHER INFORMATION: Xaa is a non-naturaly amino acid pegylated

<400> SEQUENCE: 84

```
Thr Leu Cys Gly Ala Glu Leu Val Asp Ala Leu Gln Phe Val Cys Gly
  1               5                  10                  15

Asp Arg Gly Phe Tyr Phe Asn Lys Pro Thr Gly Tyr Gly Ser Ser Ser
             20                  25                  30

Arg Ala Ala Pro Gln Thr Gly Ile Val Asp Glu Cys Cys Phe Arg Ser
         35                  40                  45

Cys Asp Leu Arg Arg Leu Glu Met Tyr Cys Ala Pro Leu Lys Pro Ala
 50                  55                  60

Lys Ser Ala Val Arg Ala Gln Arg His Thr Asp Met Pro Lys Thr Gln
 65                  70                  75                  80

Lys Tyr Gln Pro Pro Ser Thr Asn Lys Asn Thr Lys Ser Gln Arg Arg
             85                  90                  95

Lys Gly Trp Pro Lys Thr His Pro Gly Gly Glu Gln Lys Glu Gly Thr
            100                 105                 110

Glu Ala Ser Leu Gln Ile Arg Gly Lys Lys Lys Glu Gln Arg Arg Glu
        115                 120                 125

Ile Gly Ser Arg Asn Ala Glu Val Arg Ala Gln Arg His Thr Asp Met
    130                 135                 140

Pro Lys Thr Gln Lys Tyr Gln Pro Pro Ser Thr Asn Lys Asn Thr Lys
145                 150                 155                 160

Ser Gln Arg Arg Lys Gly Trp Pro Lys Thr His Pro Gly Gly Glu Gln
```

```
                       165                 170                 175
Lys Glu Gly Thr Glu Ala Ser Leu Gln Ile Arg Gly Lys Lys Glu
            180                 185                 190

Gln Arg Arg Glu Ile Gly Ser Arg Asn Ala Glu Val Arg Ala Gln Arg
        195                 200                 205

His Thr Asp Met Pro Lys Thr Gln Lys Tyr Gln Pro Ser Thr Asn
    210                 215                 220

Lys Asn Thr Lys Ser Gln Arg Lys Gly Trp Pro Lys Thr His Pro
225                 230                 235                 240

Gly Gly Glu Gln Lys Glu Gly Thr Glu Ala Ser Leu Gln Ile Arg Gly
                245                 250                 255

Lys Lys Lys Glu Gln Arg Arg Glu Ile Gly Ser Arg Asn Ala Glu Val
            260                 265                 270

Arg Ala Gln Arg His Thr Asp Met Pro Lys Thr Gln Lys Tyr Gln Pro
        275                 280                 285

Pro Ser Thr Asn Lys Asn Thr Lys Ser Gln Arg Arg Lys Gly Trp Pro
    290                 295                 300

Lys Thr His Pro Gly Gly Glu Gln Lys Glu Gly Thr Glu Ala Ser Leu
305                 310                 315                 320

Gln Ile Arg Gly Lys Lys Lys Glu Gln Arg Arg Glu Ile Gly Ser Arg
                325                 330                 335

Asn Ala Glu Xaa Arg Gly Lys Lys Gly Lys
            340                 345

<210> SEQ ID NO 85
<211> LENGTH: 70
<212> TYPE: PRT
<213> ORGANISM: Ovis aries
<220> FEATURE:
<221> NAME/KEY: PEPTIDE
<222> LOCATION: (1)...(70)
<223> OTHER INFORMATION: SHEEP REF NP_001009774.1

<400> SEQUENCE: 85

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Ala Ala Lys Ser Ala
65                  70

<210> SEQ ID NO 86
<211> LENGTH: 61
<212> TYPE: PRT
<213> ORGANISM: Ovis aries
<220> FEATURE:
<221> NAME/KEY: PEPTIDE
<222> LOCATION: (1)...(61)
<223> OTHER INFORMATION: ABB02295.1

<400> SEQUENCE: 86

Leu Val Asp Ala Leu Gln Phe Val Cys Gly Asp Arg Gly Phe Tyr Phe
1               5                   10                  15

Asn Lys Pro Thr Gly Tyr Gly Ser Ser Ser Arg Arg Ala Pro Gln Thr
            20                  25                  30
```

```
Gly Ile Val Asp Glu Cys Cys Phe Arg Ser Cys Asp Leu Arg Arg Leu
            35                  40                  45

Glu Met Tyr Cys Ala Pro Leu Lys Ala Ala Lys Ser Ala
 50                  55                  60
```

<210> SEQ ID NO 87
<211> LENGTH: 70
<212> TYPE: PRT
<213> ORGANISM: Capra hircus
<220> FEATURE:
<221> NAME/KEY: PEPTIDE
<222> LOCATION: (1)...(60)
<223> OTHER INFORMATION: P51457

<400> SEQUENCE: 87

```
Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
 50                  55                  60

Lys Pro Thr Lys Ser Ala
 65                  70
```

<210> SEQ ID NO 88
<211> LENGTH: 70
<212> TYPE: PRT
<213> ORGANISM: Ailuropoda melanoleuca
<220> FEATURE:
<221> NAME/KEY: PEPTIDE
<222> LOCATION: (1)...(70)
<223> OTHER INFORMATION: Q6JLX1

<400> SEQUENCE: 88

```
Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
 50                  55                  60

Lys Pro Ala Lys Ser Ala
 65                  70
```

<210> SEQ ID NO 89
<211> LENGTH: 70
<212> TYPE: PRT
<213> ORGANISM: Cervus elaphus
<220> FEATURE:
<221> NAME/KEY: PEPTIDE
<222> LOCATION: (1)...(70)
<223> OTHER INFORMATION: ABL98032.1

<400> SEQUENCE: 89

```
Gly Pro Glu Thr Leu Cys Gly Ala Glu Leu Val Asp Ala Leu Gln Phe
 1               5                  10                  15

Val Cys Gly Asp Arg Gly Ser Tyr Phe Asn Lys Pro Thr Gly Tyr Gly
            20                  25                  30

Ser Ser Ser Arg Arg Ala Pro Gln Thr Gly Ile Val Asp Glu Cys Cys
            35                  40                  45
```

Phe Arg Ser Cys Asp Leu Arg Arg Leu Glu Met Tyr Cys Ala Pro Leu
        50                  55                  60

Lys Pro Thr Lys Ala Ala
 65              70

<210> SEQ ID NO 90
<211> LENGTH: 70
<212> TYPE: PRT
<213> ORGANISM: Oryctolagus cuniculus
<220> FEATURE:
<221> NAME/KEY: PEPTIDE
<222> LOCATION: (1)...(70)
<223> OTHER INFORMATION: AAB48032.1

<400> SEQUENCE: 90

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
        50                  55                  60

Lys Pro Ala Lys Ala Ala
 65              70

<210> SEQ ID NO 91
<211> LENGTH: 70
<212> TYPE: PRT
<213> ORGANISM: Rattus norvegicus
<220> FEATURE:
<221> NAME/KEY: PEPTIDE
<222> LOCATION: (1)...(70)
<223> OTHER INFORMATION: REF NP_849197.1

<400> SEQUENCE: 91

Gly Pro Glu Thr Leu Cys Gly Ala Glu Leu Val Asp Ala Leu Gln Phe
 1               5                  10                  15

Val Cys Gly Pro Arg Gly Phe Tyr Phe Asn Lys Pro Thr Gly Tyr Gly
                20                  25                  30

Ser Ser Ile Arg Arg Ala Pro Gln Thr Gly Ile Val Asp Glu Cys Cys
        35                  40                  45

Phe Arg Ser Cys Asp Leu Arg Arg Leu Glu Met Tyr Cys Val Arg Cys
        50                  55                  60

Lys Pro Thr Lys Ser Ala
 65              70

<210> SEQ ID NO 92
<211> LENGTH: 70
<212> TYPE: PRT
<213> ORGANISM: Rattus norvegicus
<220> FEATURE:
<221> NAME/KEY: PEPTIDE
<222> LOCATION: (1)...(70)
<223> OTHER INFORMATION: RAT CAA29436.1

<400> SEQUENCE: 92

Gly Pro Glu Thr Leu Cys Gly Ala Glu Leu Val Asp Ala Leu Gln Phe
 1               5                  10                  15

Val Cys Gly Pro Arg Gly Phe Tyr Phe Asn Lys Pro Thr Gly Tyr Gly
                20                  25                  30

Ser Ser Ile Arg Arg Ala Pro Gln Thr Gly Ile Val Asp Glu Cys Cys

```
                35                  40                  45
Phe Arg Ser Cys Asp Leu Arg Arg Leu Glu Met Tyr Cys Ala Pro Leu
 50                  55                  60

Lys Pro Thr Lys Ser Ala
 65                  70

<210> SEQ ID NO 93
<211> LENGTH: 70
<212> TYPE: PRT
<213> ORGANISM: Mus musculus
<220> FEATURE:
<221> NAME/KEY: PEPTIDE
<222> LOCATION: (1)...(70)
<223> OTHER INFORMATION: MOUSE ISO1 REF NP_034642.1

<400> SEQUENCE: 93

Gly Pro Glu Thr Leu Cys Gly Ala Glu Leu Val Asp Ala Leu Gln Phe
  1               5                  10                  15

Val Cys Gly Pro Arg Gly Phe Tyr Phe Asn Lys Pro Thr Gly Tyr Gly
                 20                  25                  30

Ser Ser Ile Arg Arg Ala Pro Gln Thr Gly Ile Val Asp Glu Cys Cys
                35                  40                  45

Phe Arg Ser Cys Asp Leu Arg Arg Leu Glu Met Tyr Cys Ala Pro Leu
 50                  55                  60

Lys Pro Thr Lys Ala Ala
 65                  70

<210> SEQ ID NO 94
<211> LENGTH: 70
<212> TYPE: PRT
<213> ORGANISM: Anser anser
<220> FEATURE:
<221> NAME/KEY: PEPTIDE
<222> LOCATION: (1)...(70)
<223> OTHER INFORMATION: Goose ABF 57993.1

<400> SEQUENCE: 94

Gly Pro Glu Thr Leu Cys Gly Ala Glu Leu Val Asp Ala Leu Gln Phe
  1               5                  10                  15

Val Cys Gly Asp Arg Gly Phe Tyr Phe Ser Lys Pro Thr Gly Tyr Gly
                 20                  25                  30

Ser Ser Ser Arg Arg Leu His His Lys Gly Ile Val Asp Glu Cys Cys
                35                  40                  45

Phe Gln Ser Cys Asp Leu Arg Arg Leu Glu Met Tyr Cys Ala Pro Ile
 50                  55                  60

Lys Pro Pro Lys Ser Ala
 65                  70

<210> SEQ ID NO 95
<211> LENGTH: 70
<212> TYPE: PRT
<213> ORGANISM: Oncorhynchus tshawytscha
<220> FEATURE:
<221> NAME/KEY: PEPTIDE
<222> LOCATION: (1)...(70)
<223> OTHER INFORMATION: CHINOOK SALMON AAA67268.1

<400> SEQUENCE: 95

Gly Pro Glu Thr Leu Cys Gly Ala Glu Leu Val Asp Thr Leu Gln Phe
  1               5                  10                  15

Val Cys Gly Glu Arg Gly Phe Tyr Phe Ser Lys Pro Thr Gly Tyr Gly
                 20                  25                  30
```

Pro Ser Ser Arg Arg Ser His Asn Arg Gly Ile Val Asp Glu Cys Cys
            35                  40                  45

Phe Gln Ser Cys Glu Leu Arg Arg Leu Glu Met Tyr Cys Ala Pro Val
        50                  55                  60

Lys Ser Gly Lys Ala Ala
65                  70

<210> SEQ ID NO 96
<211> LENGTH: 70
<212> TYPE: PRT
<213> ORGANISM: Acipenser ruthenus
<220> FEATURE:
<221> NAME/KEY: PEPTIDE
<222> LOCATION: (1)...(70)
<223> OTHER INFORMATION: STERLET ABC54785.1

<400> SEQUENCE: 96

Gly Ser Glu Thr Leu Cys Gly Ala Glu Leu Val Asp Thr Leu Gln Phe
1               5                   10                  15

Val Cys Gly Glu Arg Gly Phe Tyr Phe Asn Lys Pro Thr Gly Tyr Gly
                20                  25                  30

Ala Ser Ser Arg Arg Pro His His Arg Gly Ile Val Asn Glu Cys Cys
            35                  40                  45

Phe Gln Ser Cys Asp Leu Arg Arg Leu Glu Met Tyr Cys Ala Pro Val
        50                  55                  60

Lys Pro Ala Lys Ala Ser
65                  70

<210> SEQ ID NO 97
<211> LENGTH: 68
<212> TYPE: PRT
<213> ORGANISM: Paralichthys olivaceus
<220> FEATURE:
<221> NAME/KEY: PEPTIDE
<222> LOCATION: (1)...(68)
<223> OTHER INFORMATION: HALIBUT CAA09267.1

<400> SEQUENCE: 97

Gly Pro Glu Thr Leu Cys Gly Ala Glu Leu Val Asp Thr Leu Gln Phe
1               5                   10                  15

Val Cys Gly Glu Arg Gly Phe Tyr Phe Ser Lys Pro Thr Gly Tyr Gly
                20                  25                  30

Pro Asn Ala Arg Arg Ser Arg Gly Ile Val Asp Glu Cys Cys Phe Gln
            35                  40                  45

Ser Cys Glu Leu Arg Arg Leu Glu Met Tyr Cys Ala Pro Ala Lys Thr
        50                  55                  60

Ser Lys Ala Ala
65

<210> SEQ ID NO 98
<211> LENGTH: 70
<212> TYPE: PRT
<213> ORGANISM: Oncorhynchus mykiss
<220> FEATURE:
<221> NAME/KEY: PEPTIDE
<222> LOCATION: (1)...(70)
<223> OTHER INFORMATION: RAINBOW TROUT Q02815

<400> SEQUENCE: 98

Gly Pro Glu Thr Leu Cys Gly Ala Glu Leu Val Asp Thr Leu Gln Phe
1               5                   10                  15

Val Cys Gly Glu Arg Gly Phe Tyr Phe Ser Lys Pro Thr Gly Tyr Gly
                20                  25                  30

```
Pro Ser Ser Arg Arg Ser His Asn Arg Gly Ile Val Asp Glu Cys Cys
            35                  40                  45

Phe Gln Ser Cys Glu Leu Arg Arg Leu Glu Met Tyr Cys Ala Pro Val
        50                  55                  60

Lys Ser Gly Lys Ala Ala
65                  70

<210> SEQ ID NO 99
<211> LENGTH: 70
<212> TYPE: PRT
<213> ORGANISM: Ictalurus punctatus
<220> FEATURE:
<221> NAME/KEY: PEPTIDE
<222> LOCATION: (1)...(70)
<223> OTHER INFORMATION: CHANNEL CATFISH AAQ56592.1

<400> SEQUENCE: 99

Gly Pro Glu Thr Leu Cys Gly Ala Glu Leu Val Asp Thr Leu Gln Phe
1               5                   10                  15

Val Cys Gly Asp Arg Gly Phe Tyr Phe Ser Lys Pro Thr Gly Tyr Gly
            20                  25                  30

Pro Asn Ser Arg Arg Leu His Asn Arg Gly Ile Val Asp Glu Cys Cys
            35                  40                  45

Phe Gln Ser Cys Glu Leu Lys Arg Leu Glu Met Tyr Cys Ala Pro Val
        50                  55                  60

Lys Ser Gly Lys Ala Pro
65                  70

<210> SEQ ID NO 100
<211> LENGTH: 70
<212> TYPE: PRT
<213> ORGANISM: Cyprinus carpio
<220> FEATURE:
<221> NAME/KEY: PEPTIDE
<222> LOCATION: (1)...(70)
<223> OTHER INFORMATION: CARP AAY21902.1

<400> SEQUENCE: 100

Gly Pro Glu Thr Leu Cys Gly Ala Glu Leu Val Asp Thr Leu Gln Phe
1               5                   10                  15

Val Cys Gly Asp Arg Gly Phe Tyr Phe Ser Lys Pro Thr Gly Tyr Gly
            20                  25                  30

Pro Ser Ser Arg Arg Ser His Asn Arg Gly Ile Val Asp Glu Cys Cys
            35                  40                  45

Phe Gln Ser Cys Glu Leu Arg Arg Leu Glu Met Tyr Cys Ala Pro Val
        50                  55                  60

Lys Pro Gly Lys Thr Pro
65                  70

<210> SEQ ID NO 101
<211> LENGTH: 70
<212> TYPE: PRT
<213> ORGANISM: Cyprinus carpio
<220> FEATURE:
<221> NAME/KEY: PEPTIDE
<222> LOCATION: (1)...(70)
<223> OTHER INFORMATION: CARP AAP78926.1

<400> SEQUENCE: 101

Gly Pro Glu Thr Leu Cys Gly Ala Glu Leu Val Asp Thr Leu Gln Phe
1               5                   10                  15

Val Cys Gly Asp Arg Gly Phe Tyr Phe Ser Lys Pro Thr Gly Tyr Gly
```

```
                        20                  25                  30

Pro Ser Ser Arg Arg Ser His Asn Arg Gly Ile Val Asp Glu Cys Cys
            35                  40                  45

Phe Gln Ser Cys Glu Leu Arg Arg Leu Glu Met Tyr Cys Ala Pro Val
        50                  55                  60

Lys Pro Gly Lys Thr Pro
65                  70
```

<210> SEQ ID NO 102
<211> LENGTH: 70
<212> TYPE: PRT
<213> ORGANISM: Danio rerio
<220> FEATURE:
<221> NAME/KEY: PEPTIDE
<222> LOCATION: (1)...(70)
<223> OTHER INFORMATION: ZEBRAFISH NP_571900.1

<400> SEQUENCE: 102

```
Gly Pro Glu Thr Leu Cys Gly Ala Glu Leu Val Asp Thr Leu Gln Phe
1               5                   10                  15

Val Cys Gly Asp Arg Gly Phe Tyr Phe Ser Lys Pro Thr Gly Tyr Gly
                20                  25                  30

Pro Ser Ser Arg Arg Ser His Asn Arg Gly Ile Val Asp Glu Cys Cys
            35                  40                  45

Phe Gln Ser Cys Glu Leu Arg Arg Leu Glu Met Tyr Cys Ala Pro Val
        50                  55                  60

Lys Thr Gly Lys Ser Pro
65                  70
```

<210> SEQ ID NO 103
<211> LENGTH: 70
<212> TYPE: PRT
<213> ORGANISM: Myxocyprinus asiaticus
<220> FEATURE:
<221> NAME/KEY: PEPTIDE
<222> LOCATION: (1)...(70)
<223> OTHER INFORMATION: CHINESE SUCKER ABH12114.1

<400> SEQUENCE: 103

```
Gly Pro Glu Thr Leu Cys Gly Ala Glu Leu Val Asp Thr Leu Gln Phe
1               5                   10                  15

Val Cys Gly Asp Arg Gly Phe Tyr Phe Ser Lys Pro Thr Gly Tyr Gly
                20                  25                  30

Pro Ser Ser Arg Arg Ser His Asn Arg Gly Ile Val Asp Glu Cys Cys
            35                  40                  45

Phe Gln Ser Cys Glu Leu Arg Arg Leu Glu Met Tyr Cys Ala Pro Val
        50                  55                  60

Lys Pro Gly Lys Ala Pro
65                  70
```

<210> SEQ ID NO 104
<211> LENGTH: 70
<212> TYPE: PRT
<213> ORGANISM: Pimephales promelas
<220> FEATURE:
<221> NAME/KEY: PEPTIDE
<222> LOCATION: (1)...(70)
<223> OTHER INFORMATION: FATHEADMINNOW AAT02176.1

<400> SEQUENCE: 104

```
Gly Pro Glu Thr Leu Cys Gly Ala Glu Leu Val Asp Thr Leu Gln Phe
1               5                   10                  15
```

Val Cys Gly Asp Arg Gly Phe Tyr Phe Asn Lys Pro Ala Gly Tyr Gly
            20                  25                  30

Ser Asn Ser Arg Arg Ser Asn Tyr Gly Ile Val Asp Glu Cys Cys
        35                  40                  45

Phe Gln Ser Cys Glu Leu Arg Arg Leu Glu Met Tyr Cys Ala Pro Val
    50                  55                  60

Lys Thr Gly Lys Thr Pro
65                  70

<210> SEQ ID NO 105
<211> LENGTH: 70
<212> TYPE: PRT
<213> ORGANISM: Carassius auratus
<220> FEATURE:
<221> NAME/KEY: PEPTIDE
<222> LOCATION: (1)...(70)
<223> OTHER INFORMATION: GOLDFISH AAC83443.1

<400> SEQUENCE: 105

Gly Pro Glu Thr Leu Cys Gly Ala Glu Leu Val Asp Thr Leu Gln Phe
1               5                   10                  15

Val Cys Gly Asp Arg Gly Phe Tyr Phe Ser Lys Pro Thr Gly Tyr Gly
            20                  25                  30

Pro Asn Ser Arg Arg Ser His Asn Arg Gly Ile Val Asp Glu Cys Cys
        35                  40                  45

Phe Gln Ser Cys Glu Leu Arg Arg Leu Glu Met Tyr Cys Ala Pro Val
    50                  55                  60

Lys Pro Gly Lys Thr Pro
65                  70

<210> SEQ ID NO 106
<211> LENGTH: 70
<212> TYPE: PRT
<213> ORGANISM: Xenopus laevis
<220> FEATURE:
<221> NAME/KEY: PEPTIDE
<222> LOCATION: (1)...(70)
<223> OTHER INFORMATION: African clawed frog AAA70330.1

<400> SEQUENCE: 106

Gly Pro Glu Thr Leu Cys Gly Ala Glu Leu Val Asp Thr Leu Gln Phe
1               5                   10                  15

Val Cys Gly Asp Arg Gly Phe Tyr Phe Ser Lys Pro Thr Gly Tyr Gly
            20                  25                  30

Ser Asn Asn Arg Arg Ser His His Arg Gly Ile Val Asp Glu Cys Cys
        35                  40                  45

Phe Gln Ser Cys Asp Phe Arg Arg Leu Glu Met Tyr Cys Ala Pro Ala
    50                  55                  60

Lys Pro Ala Lys Ser Ala
65                  70

<210> SEQ ID NO 107
<211> LENGTH: 70
<212> TYPE: PRT
<213> ORGANISM: Xenopus laevis
<220> FEATURE:
<221> NAME/KEY: PEPTIDE
<222> LOCATION: (1)...(70)
<223> OTHER INFORMATION: African clawed frog 1A P16501

<400> SEQUENCE: 107

Gly Pro Glu Thr Leu Cys Gly Ala Glu Leu Val Asp Thr Leu Gln Phe
1               5                   10                  15

```
Val Cys Gly Asp Arg Gly Phe Tyr Phe Ser Lys Pro Thr Gly Tyr Gly
             20                  25                  30

Ser Asn Asn Arg Arg Ser His His Arg Gly Ile Val Asp Glu Cys Cys
         35                  40                  45

Phe Gln Ser Cys Asp Phe Arg Arg Leu Glu Met Tyr Cys Ala Pro Ala
     50                  55                  60

Lys Gln Ala Lys Ser Ala
 65                  70
```

<210> SEQ ID NO 108
<211> LENGTH: 70
<212> TYPE: PRT
<213> ORGANISM: Monodelphis domestica
<220> FEATURE:
<221> NAME/KEY: PEPTIDE
<222> LOCATION: (1)...(70)
<223> OTHER INFORMATION: Gray short-tailed opossum XP_001373491.1

<400> SEQUENCE: 108

```
Gly Pro Glu Thr Leu Cys Gly Ala Glu Leu Val Asp Ala Leu Gln Phe
 1               5                  10                  15

Val Cys Gly Glu Arg Gly Phe Tyr Phe Ser Lys Pro Thr Gly Tyr Gly
             20                  25                  30

Ser Ser Ser Arg Arg Leu His His Thr Gly Ile Val Asp Glu Cys Cys
         35                  40                  45

Phe Arg Ser Cys Asp Leu Arg Arg Leu Glu Met Tyr Cys Ala Pro Ile
     50                  55                  60

Lys Pro Ala Lys Ser Ala
 65                  70
```

<210> SEQ ID NO 109
<211> LENGTH: 35
<212> TYPE: PRT
<213> ORGANISM: Sus scrofa
<220> FEATURE:
<221> NAME/KEY: PEPTIDE
<222> LOCATION: (1)...(35)
<223> OTHER INFORMATION: PIG REF NP_999421.1

<400> SEQUENCE: 109

```
Arg Ser Val Arg Ala Gln Arg His Thr Asp Met Pro Lys Ala Gln Lys
 1               5                  10                  15

Glu Val His Leu Lys Asn Thr Ser Arg Gly Ser Ser Gly Asn Lys Asn
             20                  25                  30

Tyr Arg Met
     35
```

<210> SEQ ID NO 110
<211> LENGTH: 35
<212> TYPE: PRT
<213> ORGANISM: Sus scrofa
<220> FEATURE:
<221> NAME/KEY: PEPTIDE
<222> LOCATION: (1)...(35)
<223> OTHER INFORMATION: PIG CLASS1 ABG88023.1

<400> SEQUENCE: 110

```
Arg Ser Val Arg Ala Gln Arg His Thr Asp Met Pro Lys Ala Arg Lys
 1               5                  10                  15

Glu Val His Leu Lys Asn Thr Ser Arg Gly Ser Ser Gly Asn Lys Asn
             20                  25                  30

Tyr Arg Met
```

-continued

```
                35

<210> SEQ ID NO 111
<211> LENGTH: 35
<212> TYPE: PRT
<213> ORGANISM: Bos taurus
<220> FEATURE:
<221> NAME/KEY: PEPTIDE
<222> LOCATION: (1)...(35)
<223> OTHER INFORMATION: COW CAA33746.1

<400> SEQUENCE: 111

Arg Ser Val Arg Ala Gln Arg His Thr Asp Met Pro Lys Ala Gln Lys
1               5                   10                  15

Glu Val His Leu Lys Asn Thr Ser Arg Gly Ser Ala Gly Asn Lys Asn
            20                  25                  30

Tyr Arg Met
        35

<210> SEQ ID NO 112
<211> LENGTH: 33
<212> TYPE: PRT
<213> ORGANISM: Canis familiaris
<220> FEATURE:
<221> NAME/KEY: PEPTIDE
<222> LOCATION: (1)...(33)
<223> OTHER INFORMATION: DOG P33712

<400> SEQUENCE: 112

Arg Ser Val Arg Ala Gln Arg His Thr Asp Met Pro Lys Ala Gln Lys
1               5                   10                  15

Glu Val His Leu Lys Asn Ala Ser Arg Gly Ser Ala Gly Asn Lys Thr
            20                  25                  30

Tyr

<210> SEQ ID NO 113
<211> LENGTH: 35
<212> TYPE: PRT
<213> ORGANISM: Canis familiaris
<220> FEATURE:
<221> NAME/KEY: PEPTIDE
<222> LOCATION: (1)...(35)
<223> OTHER INFORMATION: DOG ISO2 XP_853117.1

<400> SEQUENCE: 113

Arg Ser Val Arg Ala Gln Arg His Thr Asp Met Pro Lys Ala Gln Lys
1               5                   10                  15

Glu Val His Leu Lys Asn Ala Ser Arg Gly Ser Ala Gly Asn Lys Asn
            20                  25                  30

Tyr Arg Met
        35

<210> SEQ ID NO 114
<211> LENGTH: 35
<212> TYPE: PRT
<213> ORGANISM: Oryctolagus cuniculus
<220> FEATURE:
<221> NAME/KEY: PEPTIDE
<222> LOCATION: (1)...(35)
<223> OTHER INFORMATION: RABBIT AAB48032.1

<400> SEQUENCE: 114

Arg Ser Val Arg Ala Gln Arg His Thr Asp Met Pro Lys Thr Gln Lys
1               5                   10                  15

Glu Val His Leu Lys Asn Thr Ser Arg Gly Ser Ala Gly Asn Lys Asn
```

Tyr Arg Met
        35

<210> SEQ ID NO 115
<211> LENGTH: 35
<212> TYPE: PRT
<213> ORGANISM: Rattus norvegicus
<220> FEATURE:
<221> NAME/KEY: PEPTIDE
<222> LOCATION: (1)...(35)
<223> OTHER INFORMATION: RAT REF NP_849197.1

<400> SEQUENCE: 115

Arg Ser Ile Arg Ala Gln Arg His Thr Asp Met Pro Lys Thr Gln Lys
 1               5                  10                  15

Glu Val His Leu Lys Asn Thr Ser Arg Gly Ser Ala Gly Asn Lys Thr
            20                  25                  30

Tyr Arg Met
        35

<210> SEQ ID NO 116
<211> LENGTH: 35
<212> TYPE: PRT
<213> ORGANISM: Gallus gallus
<220> FEATURE:
<221> NAME/KEY: PEPTIDE
<222> LOCATION: (1)...(35)
<223> OTHER INFORMATION: CHICKEN NP_001004384.1

<400> SEQUENCE: 116

Arg Ser Val Arg Ala Gln Arg His Thr Asp Met Pro Lys Ala Gln Lys
 1               5                  10                  15

Glu Val His Leu Lys Asn Thr Ser Arg Gly Asn Thr Gly Asn Arg Asn
            20                  25                  30

Tyr Arg Met
        35

<210> SEQ ID NO 117
<211> LENGTH: 35
<212> TYPE: PRT
<213> ORGANISM: Meleagris gallopavo
<220> FEATURE:
<221> NAME/KEY: PEPTIDE
<222> LOCATION: (1)...(35)
<223> OTHER INFORMATION: TURKEY AAC26006.1

<400> SEQUENCE: 117

Arg Ser Val Arg Ala Gln Arg His Thr Asp Met Pro Lys Ala Gln Lys
 1               5                  10                  15

Glu Leu His Leu Lys Asn Thr Ser Arg Gly Asn Thr Gly Asn Arg Asn
            20                  25                  30

Tyr Arg Met
        35

<210> SEQ ID NO 118
<211> LENGTH: 30
<212> TYPE: PRT
<213> ORGANISM: Anser anser
<220> FEATURE:
<221> NAME/KEY: PEPTIDE
<222> LOCATION: (1)...(30)
<223> OTHER INFORMATION: GOOSE ABF57993.1

<400> SEQUENCE: 118

-continued

Arg Ser Val Arg Ala Gln Arg His Thr Asp Met Pro Lys Ala Gln Lys
1               5                   10                  15

Glu Val His Leu Lys Asn Thr Ser Arg Gly Asn Thr Glu Asn
            20                  25                  30

<210> SEQ ID NO 119
<211> LENGTH: 35
<212> TYPE: PRT
<213> ORGANISM: Oncorhynchus tshawytscha
<220> FEATURE:
<221> NAME/KEY: PEPTIDE
<222> LOCATION: (1)...(35)
<223> OTHER INFORMATION: CHINOOK SALMON AAA67268.1

<400> SEQUENCE: 119

Arg Ser Val Arg Ala Gln Arg His Thr Asp Met Pro Arg Thr Pro Lys
1               5                   10                  15

Glu Val His Gln Lys Asn Ser Ser Arg Gly Asn Thr Gly Gly Arg Asn
            20                  25                  30

Tyr Arg Met
        35

<210> SEQ ID NO 120
<211> LENGTH: 35
<212> TYPE: PRT
<213> ORGANISM: Acipenser ruthenus
<220> FEATURE:
<221> NAME/KEY: PEPTIDE
<222> LOCATION: (1)...(35)
<223> OTHER INFORMATION: STERLET ABC54785.1

<400> SEQUENCE: 120

Arg Ser Val Arg Ala Gln Arg His Thr Asp Met Pro Lys Ala Gln Lys
1               5                   10                  15

Glu Val His Ser Lys Asn Ser Ser Arg Gly Asn Thr Gly Asn Arg Asn
            20                  25                  30

Tyr Arg Ile
        35

<210> SEQ ID NO 121
<211> LENGTH: 35
<212> TYPE: PRT
<213> ORGANISM: Perca fluviatilis
<220> FEATURE:
<221> NAME/KEY: PEPTIDE
<222> LOCATION: (1)...(35)
<223> OTHER INFORMATION: PERCH CAE52916.2

<400> SEQUENCE: 121

Arg Ser Val Arg Ala Gln Arg His Thr Asp Met Pro Arg Ala Pro Lys
1               5                   10                  15

Glu Val His Gln Lys Asn Ser Ser Arg Gly Asn Thr Gly Gly Arg Asn
            20                  25                  30

Tyr Arg Met
        35

<210> SEQ ID NO 122
<211> LENGTH: 35
<212> TYPE: PRT
<213> ORGANISM: Paralichthys olivaceus
<220> FEATURE:
<221> NAME/KEY: PEPTIDE
<222> LOCATION: (1)...(35)
<223> OTHER INFORMATION: HALIBUT CAA09267.1

<400> SEQUENCE: 122

-continued

Arg Ser Val Arg Ala Gln Arg His Thr Asp Met Pro Arg Ala Pro Lys
1               5                   10                  15

Glu Val His Gln Lys Asn Ser Ser Arg Gly Thr Thr Gly Gly Arg Asn
                20                  25                  30

Tyr Arg Met
        35

<210> SEQ ID NO 123
<211> LENGTH: 35
<212> TYPE: PRT
<213> ORGANISM: Ictalurus punctatus
<220> FEATURE:
<221> NAME/KEY: PEPTIDE
<222> LOCATION: (1)...(35)
<223> OTHER INFORMATION: CHANNEL CATFISH AAQ56592.1

<400> SEQUENCE: 123

Arg Ser Val Arg Glu Gln Arg His Thr Asp Thr Pro Lys Thr Pro Lys
1               5                   10                  15

Glu Val His Gln Lys Asn Ser Ser Arg Gly Asn Thr Gly Gly Arg Asn
                20                  25                  30

Tyr Arg Met
        35

<210> SEQ ID NO 124
<211> LENGTH: 35
<212> TYPE: PRT
<213> ORGANISM: Cirrhinus molitorella
<220> FEATURE:
<221> NAME/KEY: PEPTIDE
<222> LOCATION: (1)...(35)
<223> OTHER INFORMATION: MUD CARP AAY21902.1

<400> SEQUENCE: 124

Arg Ser Ile Arg Ala Gln Arg His Thr Asp Ser Pro Lys Thr Ala Lys
1               5                   10                  15

Glu Val His Gln Lys Asn Ser Ser Arg Gly Asn Thr Gly Gly Arg Asn
                20                  25                  30

Tyr Arg Met
        35

<210> SEQ ID NO 125
<211> LENGTH: 35
<212> TYPE: PRT
<213> ORGANISM: Cirrhinus molitorella
<220> FEATURE:
<221> NAME/KEY: PEPTIDE
<222> LOCATION: (1)...(35)
<223> OTHER INFORMATION: MUD CARP AAP78926.1

<400> SEQUENCE: 125

Arg Ser Val Arg Ala Gln Arg His Thr Asp Ser Pro Arg Thr Ala Lys
1               5                   10                  15

Glu Val His Gln Lys Asn Ser Ser Arg Gly Asn Thr Gly Gly Arg Asn
                20                  25                  30

Tyr Arg Ile
        35

<210> SEQ ID NO 126
<211> LENGTH: 35
<212> TYPE: PRT
<213> ORGANISM: Danio aequipinnatus
<220> FEATURE:
<221> NAME/KEY: PEPTIDE

```
<222> LOCATION: (1)...(35)
<223> OTHER INFORMATION: GIANT DANIO ABB05519.1

<400> SEQUENCE: 126
```

Arg Ser Leu Arg Ala Gln Arg His Thr Asp Ile Pro Arg Thr Ala Lys
1               5                   10                  15

Glu Val His Gln Lys Asn Ser Ser Arg Gly Asn Thr Gly Gly Arg Asn
            20                  25                  30

Tyr Arg Met
        35

```
<210> SEQ ID NO 127
<211> LENGTH: 35
<212> TYPE: PRT
<213> ORGANISM: Danio rerio
<220> FEATURE:
<221> NAME/KEY: PEPTIDE
<222> LOCATION: (1)...(35)
<223> OTHER INFORMATION: ZEBRAFISH NP_571900.1

<400> SEQUENCE: 127
```

Arg Ser Leu Arg Ala Gln Arg His Thr Asp Ile Pro Arg Thr Pro Lys
1               5                   10                  15

Glu Val His Gln Lys Asn Ser Ser Arg Gly Asn Thr Gly Gly Arg Asn
            20                  25                  30

Tyr Arg Met
        35

```
<210> SEQ ID NO 128
<211> LENGTH: 35
<212> TYPE: PRT
<213> ORGANISM: Myxocyprinus asiaticus
<220> FEATURE:
<221> NAME/KEY: PEPTIDE
<222> LOCATION: (1)...(35)
<223> OTHER INFORMATION: CHINESE SUCKER ABH12114.1

<400> SEQUENCE: 128
```

Arg Ser Leu Arg Ala Gln Arg His Thr Asp Ile Pro Arg Thr Pro Lys
1               5                   10                  15

Asp Val His Gln Lys Asn Ser Ser Arg Gly Asn Thr Gly Gly Arg Asn
            20                  25                  30

Tyr Arg Met
        35

```
<210> SEQ ID NO 129
<211> LENGTH: 35
<212> TYPE: PRT
<213> ORGANISM: Barbus barbus
<220> FEATURE:
<221> NAME/KEY: PEPTIDE
<222> LOCATION: (1)...(35)
<223> OTHER INFORMATION: SPINYBARBUS ABE03747.1

<400> SEQUENCE: 129
```

Arg Ser Leu Arg Ala Gln Arg His Thr Asp Ser Pro Arg Thr Ala Lys
1               5                   10                  15

Glu Val His Gln Lys Asn Ser Ser Arg Gly Asn Thr Gly Gly Arg Asn
            20                  25                  30

Tyr Arg Ile
        35

```
<210> SEQ ID NO 130
<211> LENGTH: 35
```

```
<212> TYPE: PRT
<213> ORGANISM: Pimephales promelas
<220> FEATURE:
<221> NAME/KEY: PEPTIDE
<222> LOCATION: (1)...(35)
<223> OTHER INFORMATION: FATHEADMINNOW AAT02176.1

<400> SEQUENCE: 130

Arg Ser Leu Arg Ala Gln Arg His Thr Asp Ile Thr Arg Thr Ala Lys
 1               5                  10                  15

Glu Val His Gln Lys Asn Ser Ser Arg Gly Ile Thr Gly Gly Arg Asn
            20                  25                  30

Tyr Arg Met
        35

<210> SEQ ID NO 131
<211> LENGTH: 35
<212> TYPE: PRT
<213> ORGANISM: Carassius auratus
<220> FEATURE:
<221> NAME/KEY: PEPTIDE
<222> LOCATION: (1)...(35)
<223> OTHER INFORMATION: GOLDFISH AAC83443.1

<400> SEQUENCE: 131

Arg Ser Leu Arg Ala Gln Arg His Thr Asp Gly Thr Arg Thr Ala Lys
 1               5                  10                  15

Glu Val His Gln Lys Asn Ser Ser Arg Gly Asn Thr Gly Gly Arg Asn
            20                  25                  30

Tyr Arg Met
        35

<210> SEQ ID NO 132
<211> LENGTH: 35
<212> TYPE: PRT
<213> ORGANISM: Xenopus laevis
<220> FEATURE:
<221> NAME/KEY: PEPTIDE
<222> LOCATION: (1)...(35)
<223> OTHER INFORMATION: African clawed frog AAA70330.1

<400> SEQUENCE: 132

Arg Ser Val Arg Ala Gln Arg His Thr Asp Met Pro Lys Ala Gln Lys
 1               5                  10                  15

Glu Val His Pro Lys Asn Thr Ser Arg Gly Asn Thr Gly Ser Arg Gly
            20                  25                  30

Phe Arg Met
        35

<210> SEQ ID NO 133
<211> LENGTH: 35
<212> TYPE: PRT
<213> ORGANISM: Kuhlia rupestris
<220> FEATURE:
<221> NAME/KEY: PEPTIDE
<222> LOCATION: (1)...(35)
<223> OTHER INFORMATION: BREAM AAK16727.1

<400> SEQUENCE: 133

Arg Ser Leu Arg Ala Gln Arg His Thr Asp Ile Thr Arg Thr Ala Lys
 1               5                  10                  15

Glu Val His Gln Lys Asn Ser Ser Arg Gly Asn Thr Gly Gly Arg Asn
            20                  25                  30

Tyr Arg Ile
        35
```

<210> SEQ ID NO 134
<211> LENGTH: 35
<212> TYPE: PRT
<213> ORGANISM: Xenopus laevis
<220> FEATURE:
<221> NAME/KEY: PEPTIDE
<222> LOCATION: (1)...(35)
<223> OTHER INFORMATION: African clawed frog 1A P16501

<400> SEQUENCE: 134

Arg Ser Val Arg Thr Gln Arg His Thr Asp Met Pro Lys Ala Gln Lys
1               5                   10                  15

Glu Val His Pro Lys Asn Thr Ser Arg Gly Asn Thr Gly Ser Arg Gly
            20                  25                  30

Phe Arg Met
        35

<210> SEQ ID NO 135
<211> LENGTH: 46
<212> TYPE: PRT
<213> ORGANISM: Artificial Sequence
<220> FEATURE:
<223> OTHER INFORMATION: Majority consensus sequence for Seq. ID. Nos.
      16-147

<400> SEQUENCE: 135

Arg Ser Val Arg Ala Gln Arg His Thr Asp Met Pro Lys Thr Gln Lys
1               5                   10                  15

Tyr Gln Pro Pro Ser Thr Asn Lys Lys Thr Lys Ser Gln Arg Arg Arg
            20                  25                  30

Lys Gly Gly Pro Lys Thr His Pro Gly Gly Glu Gln Lys Glu
        35                  40                  45

<210> SEQ ID NO 136
<211> LENGTH: 41
<212> TYPE: PRT
<213> ORGANISM: Sus scrofa
<220> FEATURE:
<221> NAME/KEY: PEPTIDE
<222> LOCATION: (1)...(35)
<223> OTHER INFORMATION: PIG AAT47735.1

<400> SEQUENCE: 136

Arg Ser Val Arg Ala Gln Arg His Thr Asp Met Pro Lys Ala Gln Lys
1               5                   10                  15

Tyr Gln Pro Pro Ser Thr Asn Lys Lys Thr Lys Ser Gln Arg Arg Arg
            20                  25                  30

Lys Gly Ser Thr Phe Glu Glu His Lys
        35                  40

<210> SEQ ID NO 137
<211> LENGTH: 30
<212> TYPE: PRT
<213> ORGANISM: Bos indicus
<220> FEATURE:
<221> NAME/KEY: PEPTIDE
<222> LOCATION: (1)...(30)
<223> OTHER INFORMATION: COW INDIA AAU93628.1

<400> SEQUENCE: 137

Tyr Gln Pro Pro Ser Thr Asn Lys Lys Met Lys Ser Gln Arg Arg Arg
1               5                   10                  15

Lys Gly Gly Pro Lys Lys Arg Pro Gly Gly Glu Gln Lys Glu
            20                  25                  30

<210> SEQ ID NO 138
<211> LENGTH: 50
<212> TYPE: PRT
<213> ORGANISM: Bos taurus
<220> FEATURE:
<221> NAME/KEY: PEPTIDE
<222> LOCATION: (1)...(50)
<223> OTHER INFORMATION: CATTLE AAA03497.1

<400> SEQUENCE: 138

His Ala Gln Gly Ser Glu Gly Lys Pro Ala Arg Gly Gly Glu Gly
1               5                   10                  15

Arg Pro Ser Ser Tyr Gln Pro Pro Ser Thr Asn Lys Lys Met Lys Ser
            20                  25                  30

Gln Arg Arg Arg Lys Gly Gly Pro Lys Lys Arg Pro Gly Gly Glu Gln
        35                  40                  45

Lys Glu
    50

<210> SEQ ID NO 139
<211> LENGTH: 30
<212> TYPE: PRT
<213> ORGANISM: Bubalus bubalis
<220> FEATURE:
<221> NAME/KEY: PEPTIDE
<222> LOCATION: (1)...(30)
<223> OTHER INFORMATION: WATER BUFFALO AAU93630.1

<400> SEQUENCE: 139

Tyr Gln Pro Pro Ser Thr Asn Lys Lys Met Lys Ser Gln Arg Arg Arg
1               5                   10                  15

Lys Gly Gly Pro Lys Lys His Pro Gly Gly Glu Gln Lys Glu
            20                  25                  30

<210> SEQ ID NO 140
<211> LENGTH: 30
<212> TYPE: PRT
<213> ORGANISM: Ovis aries
<220> FEATURE:
<221> NAME/KEY: PEPTIDE
<222> LOCATION: (1)...(30)
<223> OTHER INFORMATION: SHEEP AAU93626.1

<400> SEQUENCE: 140

Tyr Gln Leu Pro Ser Thr Asn Lys Lys Met Lys Ser Gln Arg Arg Arg
1               5                   10                  15

Lys Gly Gly Pro Lys Lys His Pro Gly Gly Glu Gln Lys Glu
            20                  25                  30

<210> SEQ ID NO 141
<211> LENGTH: 41
<212> TYPE: PRT
<213> ORGANISM: Canis familiaris
<220> FEATURE:
<221> NAME/KEY: PEPTIDE
<222> LOCATION: (1)...(41)
<223> OTHER INFORMATION: DOG XP_866946

<400> SEQUENCE: 141

Arg Ser Val Arg Ala Gln Arg His Thr Asp Met Pro Lys Ala Gln Lys
1               5                   10                  15

Tyr His Pro Pro Ser Thr Thr Lys Arg Met Lys Ser Gln Arg Arg Arg
            20                  25                  30

Lys Gly Ser Thr Phe Glu Glu Cys Lys

-continued

```
              35                  40

<210> SEQ ID NO 142
<211> LENGTH: 41
<212> TYPE: PRT
<213> ORGANISM: Oryctolagus cuniculus
<220> FEATURE:
<221> NAME/KEY: PEPTIDE
<222> LOCATION: (1)...(41)
<223> OTHER INFORMATION: RABBIT Q95222

<400> SEQUENCE: 142

Arg Ser Val Arg Ala Gln Arg His Thr Asp Met Pro Lys Thr Gln Lys
 1               5                  10                  15

Tyr Gln Pro Pro Ser Thr Asn Lys Lys Met Lys Ser Gln Arg Arg Arg
             20                  25                  30

Lys Gly Ser Thr Phe Glu Glu His Lys
         35                  40

<210> SEQ ID NO 143
<211> LENGTH: 76
<212> TYPE: PRT
<213> ORGANISM: Pan troglodytes
<220> FEATURE:
<221> NAME/KEY: PEPTIDE
<222> LOCATION: (1)...(76)
<223> OTHER INFORMATION: CHIMPANZEE XP_001156459.1

<400> SEQUENCE: 143

Arg Ser Val Arg Ala Gln Arg His Thr Asp Met Pro Lys Thr Gln Lys
 1               5                  10                  15

Tyr Gln Pro Pro Ser Thr Asn Lys Asn Thr Lys Ser Gln Arg Arg Arg
             20                  25                  30

Lys Gly Gly Pro Lys Thr His Pro Gly Gly Glu Gln Lys Glu Gly Thr
         35                  40                  45

Glu Ala Ser Leu Gln Ile Arg Gly Lys Lys Glu Gln Arg Arg Glu
     50                  55                  60

Ile Gly Ser Arg Asn Ala Glu Cys Arg Gly Lys Lys
65                  70                  75

<210> SEQ ID NO 144
<211> LENGTH: 90
<212> TYPE: PRT
<213> ORGANISM: Macaca mulatta
<220> FEATURE:
<221> NAME/KEY: PEPTIDE
<222> LOCATION: (1)...(90)
<223> OTHER INFORMATION: RHESUS MONKEY XP_001094129.1

<400> SEQUENCE: 144

Arg Ser Val Arg Ala Gln Arg His Thr Asp Met Pro Lys Thr Gln Lys
 1               5                  10                  15

Tyr Gln Pro Pro Ser Thr Asn Lys Asn Thr Lys Ser Gln Arg Arg Arg
             20                  25                  30

Lys Gly Gly Pro Lys Thr His Pro Gly Gly Glu Gln Lys Glu Gly Thr
         35                  40                  45

Glu Ala Ser Leu Gln Ile Arg Gly Lys Lys Glu Gln Arg Arg Glu
     50                  55                  60

Ile Gly Ser Arg Asn Ala Glu Cys Arg Gly Lys Lys Gly Lys Trp Arg
65                  70                  75                  80

Thr Gly Gly Leu Ser Arg Gln Arg Gln Gly
             85                  90
```

<210> SEQ ID NO 145
<211> LENGTH: 63
<212> TYPE: PRT
<213> ORGANISM: Mus musculus
<220> FEATURE:
<221> NAME/KEY: PEPTIDE
<222> LOCATION: (1)...(60)
<223> OTHER INFORMATION: MOUSE NP_908941.1

<400> SEQUENCE: 145

Arg Ser Ile Arg Ala Gln Arg His Thr Asp Met Pro Lys Thr Gln Lys
 1               5                  10                  15

Ser Pro Ser Leu Ser Thr Asn Lys Lys Thr Lys Leu Gln Arg Arg Arg
            20                  25                  30

Lys Gly Glu Pro Lys Thr His Pro Glu Gly Glu Gln Glu Glu Val Thr
        35                  40                  45

Glu Ala Thr Arg Lys Ile Arg Gly Pro Arg Glu Lys Arg Leu Gly
    50                  55                  60

<210> SEQ ID NO 146
<211> LENGTH: 63
<212> TYPE: PRT
<213> ORGANISM: Rattus norvegicus
<220> FEATURE:
<221> NAME/KEY: PEPTIDE
<222> LOCATION: (1)...(63)
<223> OTHER INFORMATION: RAT AAA41214

<400> SEQUENCE: 146

Arg Ser Ile Arg Ala Gln Arg His Thr Asp Met Pro Lys Thr Gln Lys
 1               5                  10                  15

Ser Gln Pro Leu Ser Thr His Lys Lys Arg Lys Leu Gln Arg Arg Arg
            20                  25                  30

Lys Gly Glu Ser Lys Ala His Pro Gly Gly Glu Gln Glu Glu Gly Ala
        35                  40                  45

Glu Ala Thr Gln Lys Ile Arg Gly Asp Arg Glu Arg Arg Pro Ser
    50                  55                  60

<210> SEQ ID NO 147
<211> LENGTH: 41
<212> TYPE: PRT
<213> ORGANISM: Mus musculus
<220> FEATURE:
<221> NAME/KEY: PEPTIDE
<222> LOCATION: (1)...(41)
<223> OTHER INFORMATION: MOUSE AAX61180

<400> SEQUENCE: 147

Arg Ser Ile Arg Ala Gln Arg His Thr Asp Met Pro Lys Thr Gln Lys
 1               5                  10                  15

Ser Pro Ser Leu Ser Thr Asn Lys Lys Thr Lys Leu Gln Arg Arg Arg
            20                  25                  30

Lys Gly Ser Thr Phe Glu Glu His Lys
        35                  40

<210> SEQ ID NO 148
<211> LENGTH: 40
<212> TYPE: PRT
<213> ORGANISM: Artificial Sequence
<220> FEATURE:
<223> OTHER INFORMATION: Majority consensus sequence for Seq. ID Nos.
      149-155

<400> SEQUENCE: 148

Arg Ser Val Arg Ala Gln Arg His Thr Asp Met Pro Lys Thr Gln Lys
1               5                   10                  15

Tyr Gln Pro Pro Ser Thr Asn Lys Lys Thr Lys Ser Gln Arg Arg Arg
                20                  25                  30

Lys Gly Ser Thr Phe Glu Glu His
            35                  40

<210> SEQ ID NO 149
<211> LENGTH: 39
<212> TYPE: PRT
<213> ORGANISM: Homo sapiens
<220> FEATURE:
<221> NAME/KEY: PEPTIDE
<222> LOCATION: (1)...(39)
<223> OTHER INFORMATION: HUMAN EAW97695.1

<400> SEQUENCE: 149

Arg Ser Val Arg Ala Gln Arg His Thr Asp Met Pro Lys Thr Gln Lys
1               5                   10                  15

Tyr Gln Pro Pro Ser Thr Asn Lys Asn Thr Lys Ser Gln Arg Arg Lys
                20                  25                  30

Gly Ser Thr Phe Glu Glu Arg
            35

<210> SEQ ID NO 150
<211> LENGTH: 40
<212> TYPE: PRT
<213> ORGANISM: Sus scrofa
<220> FEATURE:
<221> NAME/KEY: PEPTIDE
<222> LOCATION: (1)...(40)
<223> OTHER INFORMATION: PIG AAT47735.1

<400> SEQUENCE: 150

Arg Ser Val Arg Ala Gln Arg His Thr Asp Met Pro Lys Ala Gln Lys
1               5                   10                  15

Tyr Gln Pro Pro Ser Thr Asn Lys Lys Thr Lys Ser Gln Arg Arg Arg
                20                  25                  30

Lys Gly Ser Thr Phe Glu Glu His
            35                  40

<210> SEQ ID NO 151
<211> LENGTH: 40
<212> TYPE: PRT
<213> ORGANISM: Canis familiaris
<220> FEATURE:
<221> NAME/KEY: PEPTIDE
<222> LOCATION: (1)...(40)
<223> OTHER INFORMATION: DOG IB XP_866946.1

<400> SEQUENCE: 151

Arg Ser Val Arg Ala Gln Arg His Thr Asp Met Pro Lys Ala Gln Lys
1               5                   10                  15

Tyr His Pro Pro Ser Thr Thr Lys Arg Met Lys Ser Gln Arg Arg Arg
                20                  25                  30

Lys Gly Ser Thr Phe Glu Glu Cys
            35                  40

<210> SEQ ID NO 152
<211> LENGTH: 40
<212> TYPE: PRT
<213> ORGANISM: Oryctolagus cuniculus
<220> FEATURE:
<221> NAME/KEY: PEPTIDE
<222> LOCATION: (1)...(40)

-continued

<223> OTHER INFORMATION: RABBIT Q95222

<400> SEQUENCE: 152

Arg Ser Val Arg Ala Gln Arg His Thr Asp Met Pro Lys Thr Gln Lys
1               5                   10                  15

Tyr Gln Pro Pro Ser Thr Asn Lys Lys Met Lys Ser Gln Arg Arg
            20                  25                  30

Lys Gly Ser Thr Phe Glu Glu His
        35                  40

<210> SEQ ID NO 153
<211> LENGTH: 40
<212> TYPE: PRT
<213> ORGANISM: Macaca mulatta
<220> FEATURE:
<221> NAME/KEY: PEPTIDE
<222> LOCATION: (1)...(40)
<223> OTHER INFORMATION: RHESUS MONKEY XP_001094016.1

<400> SEQUENCE: 153

Arg Ser Val Arg Ala Gln Arg His Thr Asp Met Pro Lys Thr Gln Lys
1               5                   10                  15

Tyr Gln Pro Pro Ser Thr Asn Lys Asn Thr Lys Ser Gln Arg Arg Arg
            20                  25                  30

Lys Gly Ser Thr Phe Glu Glu Arg
        35                  40

<210> SEQ ID NO 154
<211> LENGTH: 40
<212> TYPE: PRT
<213> ORGANISM: Mus musculus
<220> FEATURE:
<221> NAME/KEY: PEPTIDE
<222> LOCATION: (1)...(40)
<223> OTHER INFORMATION: MOUSE IB AAX61180.1

<400> SEQUENCE: 154

Arg Ser Ile Arg Ala Gln Arg His Thr Asp Met Pro Lys Thr Gln Lys
1               5                   10                  15

Ser Pro Ser Leu Ser Thr Asn Lys Lys Thr Lys Leu Gln Arg Arg Arg
            20                  25                  30

Lys Gly Ser Thr Phe Glu Glu His
        35                  40

<210> SEQ ID NO 155
<211> LENGTH: 40
<212> TYPE: PRT
<213> ORGANISM: Rattus norvegicus
<220> FEATURE:
<221> NAME/KEY: PEPTIDE
<222> LOCATION: (1)...(40)
<223> OTHER INFORMATION: RAT IB A40912

<400> SEQUENCE: 155

Arg Ser Ile Arg Ala Gln Arg His Thr Asp Met Pro Lys Thr Gln Lys
1               5                   10                  15

Ser Gln Pro Leu Ser Thr His Lys Lys Arg Lys Leu Gln Arg Arg Arg
            20                  25                  30

Lys Gly Ser Thr Leu Glu Glu His
        35                  40

<210> SEQ ID NO 156
<211> LENGTH: 156
<212> TYPE: PRT

```
<213> ORGANISM: Artificial Sequence
<220> FEATURE:
<223> OTHER INFORMATION: Majority consensus sequence for Seq. ID Nos.
      157-169

<400> SEQUENCE: 156

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
                20                  25                  30

Ser Arg Val Asn Arg Arg Ser Arg Gly Ile Val Glu Glu Cys Cys Phe
            35                  40                  45

Arg Ser Cys Asp Leu Ala Leu Leu Glu Thr Tyr Cys Ala Thr Pro Ala
        50                  55                  60

Lys Ser Glu Arg Asp Val Ser Thr Pro Thr Val Leu Pro Asp Asn
65                  70                  75                  80

Phe Pro Arg Tyr Pro Val Gly Lys Phe Phe Gln Tyr Asp Thr Trp Lys
                85                  90                  95

Gln Ser Ala Gln Arg Leu Arg Arg Gly Leu Pro Ala Leu Leu Arg Ala
                100                 105                 110

Arg Arg Gly Arg Met Leu Ala Lys Glu Leu Glu Ala Phe Arg Glu Ala
            115                 120                 125

Lys Arg His Arg Pro Leu Ile Ala Leu Pro Thr Gln Asp Pro Ala His
        130                 135                 140

Gly Gly Ala Ser Pro Glu Ala Ser Ser Asn Arg Lys
145                 150                 155

<210> SEQ ID NO 157
<211> LENGTH: 156
<212> TYPE: PRT
<213> ORGANISM: Homo sapiens
<220> FEATURE:
<221> NAME/KEY: PEPTIDE
<222> LOCATION: (1)...(156)
<223> OTHER INFORMATION: HUMAN NP_000603.1

<400> SEQUENCE: 157

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
                20                  25                  30

Ser Arg Val Ser Arg Arg Ser Arg Gly Ile Val Glu Glu Cys Cys Phe
            35                  40                  45

Arg Ser Cys Asp Leu Ala Leu Leu Glu Thr Tyr Cys Ala Thr Pro Ala
        50                  55                  60

Lys Ser Glu Arg Asp Val Ser Thr Pro Pro Thr Val Leu Pro Asp Asn
65                  70                  75                  80

Phe Pro Arg Tyr Pro Val Gly Lys Phe Phe Gln Tyr Asp Thr Trp Lys
                85                  90                  95

Gln Ser Thr Gln Arg Leu Arg Arg Gly Leu Pro Ala Leu Leu Arg Ala
                100                 105                 110

Arg Arg Gly His Val Leu Ala Lys Glu Leu Glu Ala Phe Arg Glu Ala
            115                 120                 125

Lys Arg His Arg Pro Leu Ile Ala Leu Pro Thr Gln Asp Pro Ala His
        130                 135                 140

Gly Gly Ala Pro Pro Glu Met Ala Ser Asn Arg Lys
145                 150                 155
```

```
<210> SEQ ID NO 158
<211> LENGTH: 157
<212> TYPE: PRT
<213> ORGANISM: Sus scrofa
<220> FEATURE:
<221> NAME/KEY: PEPTIDE
<222> LOCATION: (1)...(157)
<223> OTHER INFORMATION: PIG NP_999048.1

<400> SEQUENCE: 158
```

Ala Tyr Arg Pro Ser Glu Thr Leu Cys Gly Gly Glu Leu Val Asp Thr
 1               5                  10                  15

Leu Gln Phe Val Cys Gly Asp Arg Gly Phe Tyr Phe Ser Arg Pro Ala
             20                  25                  30

Ser Arg Val Asn Arg Arg Ser Arg Gly Ile Val Glu Glu Cys Cys Phe
         35                  40                  45

Arg Ser Cys Asp Leu Ala Leu Leu Glu Thr Tyr Cys Ala Thr Pro Ala
     50                  55                  60

Lys Ser Glu Arg Asp Val Ser Thr Pro Pro Thr Val Leu Pro Asp Asn
 65                  70                  75                  80

Phe Pro Arg Tyr Pro Val Gly Lys Phe Phe Arg Tyr Asp Thr Trp Lys
                 85                  90                  95

Gln Ser Ala Gln Arg Leu Arg Arg Gly Leu Pro Ala Leu Leu Arg Ala
            100                 105                 110

Arg Arg Gly Arg Thr Leu Ala Lys Glu Leu Glu Ala Val Arg Glu Ala
        115                 120                 125

Lys Arg His Arg Pro Leu Thr Ala Arg Pro Thr Arg Asp Pro Ala Ala
    130                 135                 140

His Gly Gly Ala Ser Pro Glu Ala Ser Gly His Arg Lys
145                 150                 155

```
<210> SEQ ID NO 159
<211> LENGTH: 155
<212> TYPE: PRT
<213> ORGANISM: Bos taurus
<220> FEATURE:
<221> NAME/KEY: PEPTIDE
<222> LOCATION: (1)...(155)
<223> OTHER INFORMATION: CATTLE NP_776512.2

<400> SEQUENCE: 159
```

Ala Tyr Arg Pro Ser Glu Thr Leu Cys Gly Gly Glu Leu Val Asp Thr
 1               5                  10                  15

Leu Gln Phe Val Cys Gly Asp Arg Gly Phe Tyr Phe Ser Arg Pro Ser
             20                  25                  30

Ser Arg Ile Asn Arg Arg Ser Arg Gly Ile Val Glu Glu Cys Cys Phe
         35                  40                  45

Arg Ser Cys Asp Leu Ala Leu Leu Glu Thr Tyr Cys Ala Thr Pro Ala
     50                  55                  60

Lys Ser Glu Arg Asp Val Ser Ala Ser Thr Thr Val Leu Pro Asp Asp
 65                  70                  75                  80

Val Thr Ala Tyr Pro Val Gly Lys Phe Phe Gln Tyr Asp Ile Trp Lys
                 85                  90                  95

Gln Ser Thr Gln Arg Leu Arg Arg Gly Leu Pro Ala Phe Leu Arg Ala
            100                 105                 110

Arg Arg Gly Arg Thr Leu Ala Lys Glu Leu Glu Ala Leu Arg Glu Ala
        115                 120                 125

Lys Ser His Arg Pro Leu Ile Ala Leu Pro Thr Gln Asp Pro Ala Thr
    130                 135                 140

His Gly Gly Ala Ser Ser Lys Ala Ser Ser Asp
145                 150                 155

<210> SEQ ID NO 160
<211> LENGTH: 155
<212> TYPE: PRT
<213> ORGANISM: Ovis aries
<220> FEATURE:
<221> NAME/KEY: PEPTIDE
<222> LOCATION: (1)...(155)
<223> OTHER INFORMATION: SHEEP NP_001009311.1

<400> SEQUENCE: 160

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ser
            20                  25                  30

Ser Arg Ile Asn Arg Arg Ser Arg Gly Ile Val Glu Glu Cys Cys Phe
        35                  40                  45

Arg Ser Cys Asp Leu Ala Leu Leu Glu Thr Tyr Cys Ala Ala Pro Ala
    50                  55                  60

Lys Ser Glu Arg Asp Val Ser Ala Ser Thr Thr Val Leu Pro Asp Asp
65                  70                  75                  80

Phe Thr Ala Tyr Pro Val Gly Lys Phe Phe Gln Ser Asp Thr Trp Lys
                85                  90                  95

Gln Ser Thr Gln Arg Leu Arg Arg Gly Leu Pro Ala Phe Leu Arg Ala
            100                 105                 110

Arg Arg Gly Arg Thr Leu Ala Lys Glu Leu Glu Ala Leu Arg Glu Ala
        115                 120                 125

Lys Ser His Arg Pro Leu Ile Ala Leu Pro Thr Gln Asp Pro Ala Thr
    130                 135                 140

His Gly Gly Ala Ser Ser Glu Ala Ser Ser Asp
145                 150                 155

<210> SEQ ID NO 161
<211> LENGTH: 158
<212> TYPE: PRT
<213> ORGANISM: Canis familiaris
<220> FEATURE:
<221> NAME/KEY: PEPTIDE
<222> LOCATION: (1)...(158)
<223> OTHER INFORMATION: DOG ISO1 XP_540785.2

<400> SEQUENCE: 161

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Thr Arg Arg Ser Arg Gly Ile Val Glu Glu Cys Cys
        35                  40                  45

Phe Arg Ser Cys Asp Leu Ala Leu Leu Glu Thr Tyr Cys Ala Thr Pro
    50                  55                  60

Ala Lys Ser Glu Arg Asp Val Ser Thr Pro Pro Thr Val Leu Pro Asp
65                  70                  75                  80

Asn Phe Pro Arg Tyr Pro Val Gly Lys Phe Phe Gln Tyr Asp Thr Trp
                85                  90                  95

Lys Gln Ser Ala Gln Arg Leu Arg Arg Gly Leu Pro Ala Leu Leu Arg
            100                 105                 110

Ala Arg Arg Gly Arg Met Leu Ala Lys Glu Leu Glu Ala Phe Arg Glu
        115                 120                 125

Ala Lys Arg His Arg Pro Leu Ile Ala Leu Pro Thr His Asp Pro Ala
    130                 135                 140

Thr His Gly Gly Ala Ser Pro Glu Ala Ser Gly Asn Gln Lys
145                 150                 155

<210> SEQ ID NO 162
<211> LENGTH: 161
<212> TYPE: PRT
<213> ORGANISM: Canis familiaris
<220> FEATURE:
<221> NAME/KEY: PEPTIDE
<222> LOCATION: (1)...(161)
<223> OTHER INFORMATION: DOG ISO2 XP_851137.1

<400> SEQUENCE: 162

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Asp Leu Ser
            20                  25                  30

Arg Pro Ala Ser Arg Val Thr Arg Arg Ser Ser Arg Gly Ile Val Glu
        35                  40                  45

Glu Cys Cys Phe Arg Ser Cys Asp Leu Ala Leu Leu Glu Thr Tyr Cys
    50                  55                  60

Ala Thr Pro Ala Lys Ser Glu Arg Asp Val Ser Thr Pro Pro Thr Val
65                  70                  75                  80

Leu Pro Asp Asn Phe Pro Arg Tyr Pro Val Gly Lys Phe Phe Gln Tyr
                85                  90                  95

Asp Thr Trp Lys Gln Ser Ala Gln Arg Leu Arg Arg Gly Leu Pro Ala
            100                 105                 110

Leu Leu Arg Ala Arg Arg Gly Arg Met Leu Ala Lys Glu Leu Glu Ala
        115                 120                 125

Phe Arg Glu Ala Lys Arg His Arg Pro Leu Ile Ala Leu Pro Thr His
    130                 135                 140

Asp Pro Ala Thr His Gly Gly Ala Ser Pro Glu Ala Ser Gly Asn Gln
145                 150                 155                 160

Lys

<210> SEQ ID NO 163
<211> LENGTH: 170
<212> TYPE: PRT
<213> ORGANISM: Canis familiaris
<220> FEATURE:
<221> NAME/KEY: PEPTIDE
<222> LOCATION: (1)...(170)
<223> OTHER INFORMATION: DOG ISO3 XP_863200.1

<400> SEQUENCE: 163

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Asp Ala Ala
            20                  25                  30

Leu Leu Pro Pro Val Gly Leu Pro Gly Arg Pro Ala Ser Arg Val Thr
        35                  40                  45

Arg Arg Ser Ser Arg Gly Ile Val Glu Glu Cys Cys Phe Arg Ser Cys
    50                  55                  60

Asp Leu Ala Leu Leu Glu Thr Tyr Cys Ala Thr Pro Ala Lys Ser Glu
65                  70                  75                  80

Arg Asp Val Ser Thr Pro Pro Thr Val Leu Pro Asp Asn Phe Pro Arg
                85                  90                  95

```
Tyr Pro Val Gly Lys Phe Phe Gln Tyr Asp Thr Trp Lys Gln Ser Ala
            100                 105                 110

Gln Arg Leu Arg Arg Gly Leu Pro Ala Leu Leu Arg Ala Arg Arg Gly
        115                 120                 125

Arg Met Leu Ala Lys Glu Leu Glu Ala Phe Arg Glu Ala Lys Arg His
    130                 135                 140

Arg Pro Leu Ile Ala Leu Pro Thr His Asp Pro Ala Thr His Gly Gly
145                 150                 155                 160

Ala Ser Pro Glu Ala Ser Gly Asn Gln Lys
                165                 170

<210> SEQ ID NO 164
<211> LENGTH: 164
<212> TYPE: PRT
<213> ORGANISM: Gallus gallus
<220> FEATURE:
<221> NAME/KEY: PEPTIDE
<222> LOCATION: (1)...(164)
<223> OTHER INFORMATION: RED JUNGLE FOWL XP_421026.2

<400> SEQUENCE: 164

Ala Tyr Gly Thr Ala Glu Thr Leu Cys Gly Gly Glu Leu Val Asp Thr
1               5                   10                  15

Leu Gln Phe Val Cys Gly Asp Arg Gly Phe Tyr Phe Ser Arg Pro Val
            20                  25                  30

Gly Arg Asn Asn Arg Arg Ile Asn Arg Gly Ile Val Glu Glu Cys Cys
        35                  40                  45

Phe Arg Ser Cys Asp Leu Ala Leu Leu Glu Thr Tyr Cys Ala Lys Ser
    50                  55                  60

Val Lys Ser Glu Arg Asp Leu Ser Ala Thr Ser Leu Ala Gly Leu Pro
65                  70                  75                  80

Ala Leu Asn Lys Glu Ser Phe Gln Lys Pro Ser His Ala Lys Tyr Ser
                85                  90                  95

Lys Tyr Asn Val Trp Gln Lys Lys Ser Ser Gln Arg Leu Gln Arg Glu
            100                 105                 110

Val Pro Gly Ile Leu Arg Ala Arg Arg Tyr Arg Trp Gln Ala Glu Gly
        115                 120                 125

Leu Gln Ala Ala Glu Glu Ala Arg Ala Met His Arg Pro Leu Ile Ser
    130                 135                 140

Leu Pro Ser Gln Arg Pro Pro Ala Pro Arg Ala Ser Pro Glu Ala Thr
145                 150                 155                 160

Gly Pro Gln Glu

<210> SEQ ID NO 165
<211> LENGTH: 156
<212> TYPE: PRT
<213> ORGANISM: Rattus norvegicus
<220> FEATURE:
<221> NAME/KEY: PEPTIDE
<222> LOCATION: (1)...(156)
<223> OTHER INFORMATION: RAT NP_113699.1

<400> SEQUENCE: 165

Ala Tyr Arg Pro Ser Glu Thr Leu Cys Gly Gly Glu Leu Val Asp Thr
1               5                   10                  15

Leu Gln Phe Val Cys Ser Asp Arg Gly Phe Tyr Phe Ser Arg Pro Ser
            20                  25                  30

Ser Arg Ala Asn Arg Arg Ser Arg Gly Ile Val Glu Glu Cys Cys Phe
        35                  40                  45
```

```
Arg Ser Cys Asp Leu Ala Leu Leu Glu Thr Tyr Cys Ala Thr Pro Ala
        50                  55                  60

Lys Ser Glu Arg Asp Val Ser Thr Ser Gln Ala Val Leu Pro Asp Asp
 65                  70                  75                  80

Phe Pro Arg Tyr Pro Val Gly Lys Phe Lys Phe Asp Thr Trp Arg
                 85                  90                  95

Gln Ser Ala Gly Arg Leu Arg Arg Gly Leu Pro Ala Leu Leu Arg Ala
                100                 105                 110

Arg Arg Gly Arg Met Leu Ala Lys Glu Leu Glu Ala Phe Arg Glu Ala
            115                 120                 125

Lys Arg His Arg Pro Leu Ile Val Leu Pro Pro Lys Asp Pro Ala His
            130                 135                 140

Gly Gly Ala Ser Ser Glu Met Ser Ser Asn His Gln
145                 150                 155

<210> SEQ ID NO 166
<211> LENGTH: 140
<212> TYPE: PRT
<213> ORGANISM: Mus musculus
<220> FEATURE:
<221> NAME/KEY: PEPTIDE
<222> LOCATION: (1)...(156)
<223> OTHER INFORMATION: MOUSE NP_034644.1

<400> SEQUENCE: 166

Leu Gln Phe Val Cys Ser Asp Arg Gly Phe Tyr Phe Ser Arg Pro Ser
  1               5                  10                  15

Ser Arg Ala Asn Arg Arg Ser Arg Gly Ile Val Glu Glu Cys Cys Phe
                 20                  25                  30

Arg Ser Cys Asp Leu Ala Leu Leu Glu Thr Tyr Cys Ala Thr Pro Ala
                 35                  40                  45

Lys Ser Glu Arg Asp Val Ser Thr Ser Gln Ala Val Leu Pro Asp Asp
 50                  55                  60

Phe Pro Arg Tyr Pro Val Gly Lys Phe Phe Gln Tyr Asp Thr Trp Arg
 65                  70                  75                  80

Gln Ser Ala Gly Arg Leu Arg Arg Gly Leu Pro Ala Leu Leu Arg Ala
                 85                  90                  95

Arg Arg Gly Arg Met Leu Ala Lys Glu Leu Lys Glu Phe Arg Glu Ala
                100                 105                 110

Lys Arg His Arg Pro Leu Ile Val Leu Pro Pro Lys Asp Pro Ala His
            115                 120                 125

Gly Gly Ala Ser Ser Glu Met Ser Ser Asn His Gln
130                 135                 140

<210> SEQ ID NO 167
<211> LENGTH: 160
<212> TYPE: PRT
<213> ORGANISM: Pan troglodytes
<220> FEATURE:
<221> NAME/KEY: PEPTIDE
<222> LOCATION: (1)...(160)
<223> OTHER INFORMATION: CHIMPANZEE XP_001153640.1

<400> SEQUENCE: 167

Ala Tyr Arg Pro Ser Glu Thr Leu Cys Gly Gly Glu Leu Val Asp Thr
  1               5                  10                  15

Leu Gln Phe Val Cys Gly Asp Arg Gly Phe Tyr Phe Ser Lys Ala Ser
                 20                  25                  30

Thr Pro Ala Ala Phe Pro Ile Thr Arg Pro Leu Arg Arg Val Gly Gln
```

```
                35                  40                  45
Arg Cys Cys Arg Gly Cys Pro Ala Asp Leu Arg Asp Ala Ser
 50                  55                  60

Ala Phe Pro Arg Arg Glu Ser Arg His Leu Leu Thr Ser Pro Phe Pro
 65                  70                  75                  80

Ser Gln Asp Asn Phe Pro Arg Tyr Pro Val Gly Lys Phe Phe Gln Tyr
                 85                  90                  95

Asp Thr Trp Lys Gln Ser Thr Gln Arg Leu Arg Arg Gly Leu Pro Ala
                100                 105                 110

Leu Leu Arg Ala Arg Arg Gly His Met Leu Ala Lys Glu Leu Glu Ala
                115                 120                 125

Phe Arg Glu Ala Lys Arg His Arg Pro Leu Ile Ala Leu Pro Thr Gln
                130                 135                 140

Asp Pro Ala His Gly Gly Ala Pro Pro Glu Met Ala Ser Asn Arg Lys
145                 150                 155                 160

<210> SEQ ID NO 168
<211> LENGTH: 167
<212> TYPE: PRT
<213> ORGANISM: Danio rerio
<220> FEATURE:
<221> NAME/KEY: PEPTIDE
<222> LOCATION: (1)...(166)
<223> OTHER INFORMATION: ZEBRAFISH ISO1 XP_001338042.1

<400> SEQUENCE: 168

Glu Val Ala Ser Ala Glu Thr Leu Cys Gly Gly Glu Leu Val Asp Ala
 1               5                  10                  15

Leu Gln Phe Val Cys Glu Asp Arg Gly Phe Tyr Phe Ser Arg Pro Thr
                20                  25                  30

Ser Arg Ser Asn Ser Arg Arg Ser Gln Asn Arg Gly Ile Val Glu Glu
                35                  40                  45

Cys Cys Phe Ser Ser Cys Asn Leu Ala Leu Leu Glu Gln Tyr Cys Ala
 50                  55                  60

Lys Pro Ala Lys Ser Glu Arg Asp Val Ser Ala Thr Ser Leu Gln Val
 65                  70                  75                  80

Ile Pro Val Met Pro Ala Leu Lys Gln Glu Val Pro Arg Lys His Val
                 85                  90                  95

Thr Val Lys Tyr Ser Lys Tyr Asp Val Trp Gln Arg Lys Ala Ala Gln
                100                 105                 110

Arg Leu Arg Arg Gly Ile Pro Ala Ile Leu Arg Ala Lys Lys Phe Arg
                115                 120                 125

Arg Gln Ala Glu Arg Ile Lys Ala Gln Glu Gln Leu Leu His His Arg
                130                 135                 140

Pro Leu Ile Thr Leu Pro Ser Lys Leu Pro Pro Ile Leu Leu Pro Thr
145                 150                 155                 160

Glu Asn Tyr Val Ser His Lys
                165

<210> SEQ ID NO 169
<211> LENGTH: 161
<212> TYPE: PRT
<213> ORGANISM: Danio rerio
<220> FEATURE:
<221> NAME/KEY: PEPTIDE
<222> LOCATION: (1)...(167)
<223> OTHER INFORMATION: ZEBRAFISH ISO2B NP_571508.1

<400> SEQUENCE: 169
```

```
Asn Val Thr Ala Gly Glu Thr Leu Cys Gly Gly Glu Leu Val Asp Thr
 1               5                  10                  15

Leu Gln Phe Val Cys Gly Glu Asp Gly Phe Tyr Ile Ser Arg Pro Asn
                20                  25                  30

Arg Ser Asn Ser Arg Arg Pro Gln Arg Gly Ile Val Glu Glu Cys Cys
            35                  40                  45

Phe Arg Ser Cys Glu Leu His Leu Leu Gln Gln Tyr Cys Ala Lys Pro
        50                  55                  60

Val Lys Ser Glu Arg Asp Val Ser Ser Thr Ser Leu Gln Val Phe Pro
65                  70                  75                  80

Val Ser Gln Ala Leu His Lys Asp Thr Ile Asn Val Lys Tyr Ser Lys
                85                  90                  95

Tyr Glu Val Trp Gln Gln Lys Ala Ala Gln Arg Leu Arg Arg Gly Val
                100                 105                 110

Pro Ser Ile Leu Leu Ala Arg Lys Phe Arg Arg Gln Met Glu Lys Ile
            115                 120                 125

Gln Asp Glu Glu Gln Thr Ser Phe His Arg Pro Leu Met Thr Leu Pro
    130                 135                 140

Asn Arg Gln Pro Ala Ile Val Pro His Val Gln Ile Ser Thr Ser Arg
145                 150                 155                 160

Lys
```

```
<210> SEQ ID NO 170
<211> LENGTH: 89
<212> TYPE: PRT
<213> ORGANISM: Artificial Sequence
<220> FEATURE:
<223> OTHER INFORMATION: Majority consensus sequence for Seq. ID Nos.
      171-180

<400> SEQUENCE: 170
```

```
Arg Asp Val Ser Thr Pro Pro Thr Val Leu Pro Asp Asn Phe Pro Arg
 1               5                  10                  15

Tyr Pro Val Gly Lys Phe Phe Gln Tyr Asp Thr Trp Lys Gln Ser Ala
                20                  25                  30

Gln Arg Leu Arg Arg Gly Leu Pro Ala Leu Leu Arg Ala Arg Arg Gly
            35                  40                  45

Arg Met Leu Ala Lys Glu Leu Gly Ala Phe Arg Glu Ala Lys Arg His
        50                  55                  60

Arg Pro Leu Ile Ala Leu Pro Thr Gln Asp Pro Ala His Gly Gly Ala
65                  70                  75                  80

Ser Pro Glu Ala Ser Ser Asn Arg Lys
                85
```

```
<210> SEQ ID NO 171
<211> LENGTH: 90
<212> TYPE: PRT
<213> ORGANISM: Sus scrofa
<220> FEATURE:
<221> NAME/KEY: PEPTIDE
<222> LOCATION: (1)...(90)
<223> OTHER INFORMATION: PIG NP_999048.1

<400> SEQUENCE: 171
```

```
Arg Asp Val Ser Thr Pro Pro Thr Val Leu Pro Asp Asn Phe Pro Arg
 1               5                  10                  15

Tyr Pro Val Gly Lys Phe Phe Gln Tyr Asp Thr Trp Lys Gln Ser Ala
                20                  25                  30

Gln Arg Leu Arg Arg Gly Leu Pro Ala Leu Leu Arg Ala Arg Arg Gly
```

```
                35                  40                  45
Arg Thr Leu Ala Lys Glu Leu Glu Ala Val Arg Glu Ala Lys Arg His
 50                  55                  60

Arg Pro Leu Thr Ala Arg Pro Thr Arg Asp Pro Ala Ala His Gly Gly
 65                  70                  75                  80

Ala Ser Pro Glu Ala Ser Gly His Arg Lys
                 85                  90

<210> SEQ ID NO 172
<211> LENGTH: 88
<212> TYPE: PRT
<213> ORGANISM: Bos taurus
<220> FEATURE:
<221> NAME/KEY: PEPTIDE
<222> LOCATION: (1)...(88)
<223> OTHER INFORMATION: CATTLE NP_776512.2

<400> SEQUENCE: 172

Arg Asp Val Ser Ala Ser Thr Thr Val Leu Pro Asp Asp Val Thr Ala
  1               5                  10                  15

Tyr Pro Val Gly Lys Phe Phe Gln Tyr Asp Ile Trp Lys Gln Ser Thr
                 20                  25                  30

Gln Arg Leu Arg Arg Gly Leu Pro Ala Phe Leu Arg Ala Arg Arg Gly
                 35                  40                  45

Arg Thr Leu Ala Lys Glu Leu Glu Ala Leu Arg Glu Ala Lys Ser His
 50                  55                  60

Arg Pro Leu Ile Ala Leu Pro Thr Gln Asp Pro Ala Thr His Gly Gly
 65                  70                  75                  80

Ala Ser Ser Lys Ala Ser Ser Asp
                 85

<210> SEQ ID NO 173
<211> LENGTH: 88
<212> TYPE: PRT
<213> ORGANISM: Ovis aries
<220> FEATURE:
<221> NAME/KEY: PEPTIDE
<222> LOCATION: (1)...(88)
<223> OTHER INFORMATION: SHEEP NP_001009311.1

<400> SEQUENCE: 173

Arg Asp Val Ser Ala Ser Thr Thr Val Leu Pro Asp Asp Phe Thr Ala
  1               5                  10                  15

Tyr Pro Val Gly Lys Phe Phe Gln Ser Asp Thr Trp Lys Gln Ser Thr
                 20                  25                  30

Gln Arg Leu Arg Arg Gly Leu Pro Ala Phe Leu Arg Ala Arg Arg Gly
                 35                  40                  45

Arg Thr Leu Ala Lys Glu Leu Glu Ala Leu Arg Glu Ala Lys Ser His
 50                  55                  60

Arg Pro Leu Ile Ala Leu Pro Thr Gln Asp Pro Ala Thr His Gly Gly
 65                  70                  75                  80

Ala Ser Ser Glu Ala Ser Ser Asp
                 85

<210> SEQ ID NO 174
<211> LENGTH: 90
<212> TYPE: PRT
<213> ORGANISM: Canis familiaris
<220> FEATURE:
<221> NAME/KEY: PEPTIDE
<222> LOCATION: (1)...(90)
<223> OTHER INFORMATION: DOG ISO1 XP_540785.2
```

<400> SEQUENCE: 174

Arg Asp Val Ser Thr Pro Pro Thr Val Leu Pro Asp Asn Phe Pro Arg
1               5                   10                  15

Tyr Pro Val Gly Lys Phe Phe Gln Tyr Asp Thr Trp Lys Gln Ser Ala
            20                  25                  30

Gln Arg Leu Arg Arg Gly Leu Pro Ala Leu Leu Arg Ala Arg Arg Gly
        35                  40                  45

Arg Met Leu Ala Lys Glu Leu Glu Ala Phe Arg Glu Ala Lys Arg His
    50                  55                  60

Arg Pro Leu Ile Ala Leu Pro Thr His Asp Pro Ala Thr His Gly Gly
65                  70                  75                  80

Ala Ser Pro Glu Ala Ser Gly Asn Gln Lys
                85                  90

<210> SEQ ID NO 175
<211> LENGTH: 96
<212> TYPE: PRT
<213> ORGANISM: Gallus gallus
<220> FEATURE:
<221> NAME/KEY: PEPTIDE
<222> LOCATION: (1)...(96)
<223> OTHER INFORMATION: RED JUNGLE FOWL XP_421026.2

<400> SEQUENCE: 175

Arg Asp Leu Ser Ala Thr Ser Leu Ala Gly Leu Pro Ala Leu Asn Lys
1               5                   10                  15

Glu Ser Phe Gln Lys Pro Ser His Ala Lys Tyr Ser Lys Tyr Asn Val
            20                  25                  30

Trp Gln Lys Lys Ser Ser Gln Arg Leu Gln Arg Glu Val Pro Gly Ile
        35                  40                  45

Leu Arg Ala Arg Arg Tyr Arg Trp Gln Ala Glu Gly Leu Gln Ala Ala
    50                  55                  60

Glu Glu Ala Arg Ala Met His Arg Pro Leu Ile Ser Leu Pro Ser Gln
65                  70                  75                  80

Arg Pro Pro Ala Pro Arg Ala Ser Pro Glu Ala Thr Gly Pro Gln Glu
                85                  90                  95

<210> SEQ ID NO 176
<211> LENGTH: 89
<212> TYPE: PRT
<213> ORGANISM: Rattus norvegicus
<220> FEATURE:
<221> NAME/KEY: PEPTIDE
<222> LOCATION: (1)...(89)
<223> OTHER INFORMATION: RAT NP_113699.1

<400> SEQUENCE: 176

Arg Asp Val Ser Thr Ser Gln Ala Val Leu Pro Asp Asp Phe Pro Arg
1               5                   10                  15

Tyr Pro Val Gly Lys Phe Phe Lys Phe Asp Thr Trp Arg Gln Ser Ala
            20                  25                  30

Gly Arg Leu Arg Arg Gly Leu Pro Ala Leu Leu Arg Ala Arg Arg Gly
        35                  40                  45

Arg Met Leu Ala Lys Glu Leu Glu Ala Phe Arg Glu Ala Lys Arg His
    50                  55                  60

Arg Pro Leu Ile Val Leu Pro Pro Lys Asp Pro Ala His Gly Gly Ala
65                  70                  75                  80

Ser Ser Glu Met Ser Ser Asn His Gln
                85

<210> SEQ ID NO 177
<211> LENGTH: 89
<212> TYPE: PRT
<213> ORGANISM: Mus musculus
<220> FEATURE:
<221> NAME/KEY: PEPTIDE
<222> LOCATION: (1)...(89)
<223> OTHER INFORMATION: MOUSE NP_034644.1

<400> SEQUENCE: 177

Arg Asp Val Ser Thr Ser Gln Ala Val Leu Pro Asp Asp Phe Pro Arg
1               5                   10                  15

Tyr Pro Val Gly Lys Phe Phe Gln Tyr Asp Thr Trp Arg Gln Ser Ala
            20                  25                  30

Gly Arg Leu Arg Arg Gly Leu Pro Ala Leu Leu Arg Ala Arg Arg Gly
        35                  40                  45

Arg Met Leu Ala Lys Glu Leu Lys Glu Phe Arg Glu Ala Lys Arg His
    50                  55                  60

Arg Pro Leu Ile Val Leu Pro Pro Lys Asp Pro Ala His Gly Gly Ala
65                  70                  75                  80

Ser Ser Glu Met Ser Ser Asn His Gln
                85

<210> SEQ ID NO 178
<211> LENGTH: 89
<212> TYPE: PRT
<213> ORGANISM: Pan troglodytes
<220> FEATURE:
<221> NAME/KEY: PEPTIDE
<222> LOCATION: (1)...(89)
<223> OTHER INFORMATION: CHIMPANZEE XP_001153640.1

<400> SEQUENCE: 178

Arg His Leu Leu Thr Ser Pro Phe Pro Ser Gln Asp Asn Phe Pro Arg
1               5                   10                  15

Tyr Pro Val Gly Lys Phe Phe Gln Tyr Asp Thr Trp Lys Gln Ser Thr
            20                  25                  30

Gln Arg Leu Arg Arg Gly Leu Pro Ala Leu Leu Arg Ala Arg Arg Gly
        35                  40                  45

His Met Leu Ala Lys Glu Leu Glu Ala Phe Arg Glu Ala Lys Arg His
    50                  55                  60

Arg Pro Leu Ile Ala Leu Pro Thr Gln Asp Pro Ala His Gly Gly Ala
65                  70                  75                  80

Pro Pro Glu Met Ala Ser Asn Arg Lys
                85

<210> SEQ ID NO 179
<211> LENGTH: 97
<212> TYPE: PRT
<213> ORGANISM: Danio rerio
<220> FEATURE:
<221> NAME/KEY: PEPTIDE
<222> LOCATION: (1)...(97)
<223> OTHER INFORMATION: ZEBRAFISH ISO1 XP_001338042.1

<400> SEQUENCE: 179

Arg Asp Val Ser Ala Thr Ser Leu Gln Val Ile Pro Val Met Pro Ala
1               5                   10                  15

Leu Lys Gln Glu Val Pro Arg Lys His Val Thr Val Lys Tyr Ser Lys
            20                  25                  30

Tyr Asp Val Trp Gln Arg Lys Ala Ala Gln Arg Leu Arg Arg Gly Ile

```
                        35                  40                  45
Pro Ala Ile Leu Arg Ala Lys Lys Phe Arg Arg Gln Ala Glu Arg Ile
 50                  55                  60

Lys Ala Gln Glu Gln Leu Leu His His Arg Pro Leu Ile Thr Leu Pro
 65                  70                  75                  80

Ser Lys Leu Pro Pro Ile Leu Leu Pro Thr Glu Asn Tyr Val Ser His
                 85                  90                  95

Lys

<210> SEQ ID NO 180
<211> LENGTH: 93
<212> TYPE: PRT
<213> ORGANISM: Danio rerio
<220> FEATURE:
<221> NAME/KEY: PEPTIDE
<222> LOCATION: (1)...(93)
<223> OTHER INFORMATION: ZEBRAFISH ISO2B NP_571508.1

<400> SEQUENCE: 180

Arg Asp Val Ser Ser Thr Ser Leu Gln Val Phe Pro Val Ser Gln Ala
 1               5                  10                  15

Leu His Lys Asp Thr Ile Asn Val Lys Tyr Ser Lys Tyr Glu Val Trp
                 20                  25                  30

Gln Gln Lys Ala Ala Gln Arg Leu Arg Arg Gly Val Pro Ser Ile Leu
             35                  40                  45

Leu Ala Arg Lys Phe Arg Arg Gln Met Glu Lys Ile Gln Asp Glu Glu
 50                  55                  60

Gln Thr Ser Phe His Arg Pro Leu Met Thr Leu Pro Asn Arg Gln Pro
 65                  70                  75                  80

Ala Ile Val Pro His Val Gln Ile Ser Thr Ser Arg Lys
                 85                  90

<210> SEQ ID NO 181
<211> LENGTH: 106
<212> TYPE: PRT
<213> ORGANISM: Homo sapiens
<220> FEATURE:
<221> NAME/KEY: PEPTIDE
<222> LOCATION: (1)...(106)
<223> OTHER INFORMATION: HIGF-1-EC:  P2, E3; R37A; R71, S72

<400> SEQUENCE: 181

Gly Thr Leu Cys Gly Ala Glu Leu Val Asp Ala Leu Gln Phe Val Cys
 1               5                  10                  15

Gly Asp Arg Gly Phe Tyr Phe Asn Lys Pro Thr Gly Tyr Gly Ser Ser
                 20                  25                  30

Ser Arg Ala Ala Pro Gln Thr Gly Ile Val Asp Glu Cys Cys Phe Arg
             35                  40                  45

Ser Cys Asp Leu Arg Arg Leu Glu Met Tyr Cys Ala Pro Leu Lys Pro
 50                  55                  60

Ala Lys Ser Ala Val Arg Ala Gln Arg His Thr Asp Met Pro Lys Thr
 65                  70                  75                  80

Gln Lys Tyr Gln Pro Pro Ser Thr Asn Lys Asn Thr Lys Ser Gln Arg
                 85                  90                  95

Arg Lys Gly Ser Thr Phe Glu Glu Arg Lys
            100                 105
```

What is claimed is:

1. A polypeptide comprising the sequence of SEQ ID NO: 53.

2. A polynucleotide encoding a polypeptide comprising the sequence of SEQ ID NO: 53.

3. A polypeptide comprising the sequence of SEQ ID NO: 53, which is pegylated.

4. A polypeptide, wherein the sequence of the polypeptide consists of the sequence of SEQ ID NO: 53.

5. A polypeptide, wherein the sequence of the polypeptide consists of the sequence of SEQ ID NO: 8.

6. A polypeptide wherein the sequence of the polypeptide comprises the sequence of SEQ ID NO: 8.

7. A human IGF-1 precursor protein comprising the polypeptide of SEQ ID NO: 5 wherein amino acid positions 3, 71, and 72 are deleted and amino acid positions 36 and/or 37 are either deleted or substituted with another amino acid such that cleavage between amino acids 36 and 37 is prevented.

8. The human IGF-1 precursor protein of claim 7 wherein amino acid position 36 is deleted.

9. The human IGF-1 precursor protein of claim 7 wherein amino acid position 36 is substituted.

10. The human IGF-1 precursor protein of claim 7 wherein amino acid position 36 is substituted with alanine.

11. The human IGF-1 precursor protein of claim 7 wherein amino acid position 37 is deleted.

12. The human IGF-1 precursor protein of claim 7 wherein amino acid position 37 is substituted.

13. The human IGF-1 precursor protein of claim 7 wherein amino acid position 37 is substituted with alanine.

14. The human IGF-1 precursor protein of claim 7 wherein amino acid positions 1 and 2 are additionally deleted.

15. The human IGF-1 precursor protein of any one of claims 7 to 14 which further comprises a poly(ethylene glycol) moiety covalently attached to the human IGF-1 precursor protein.

16. A polynucleotide encoding the human IGF-1 precursor protein of any one of claims 7 to 14.

* * * * *